United States Patent
Gruber et al.

(12) 
(10) Patent No.: US 6,410,326 B1
(45) Date of Patent: *Jun. 25, 2002

(54) METHOD FOR INHIBITING HUMAN TUMOR CELLS

(75) Inventors: Harry E. Gruber, San Diego; Douglas J. Jolly, La Jolla; James G. Respess, San Diego; Paul K. Laikind, San Diego; Jack R. Barber, San Diego, all of CA (US); Daniel C. St. Louis, Rockville, MD (US); Sunil D. Chada, Vista, CA (US); Stephen M. W. Chang; John F. Warner, both of San Diego, CA (US)

(73) Assignee: Chiron Corporation, Emeryville, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/486,683

(22) Filed: Jun. 7, 1995

Related U.S. Application Data

(60) Division of application No. 08/344,743, filed on Nov. 23, 1994, which is a continuation of application No. 08/139,994, filed on Oct. 20, 1993, now abandoned, which is a continuation of application No. 07/965,084, filed on Oct. 22, 1992, now abandoned, which is a continuation of application No. 07/586,603, filed on Sep. 21, 1990, now abandoned, which is a continuation-in-part of application No. 07/565,606, filed on Aug. 10, 1990, now abandoned, which is a continuation-in-part of application No. 07/395,932, filed on Aug. 18, 1989, now abandoned, which is a continuation-in-part of application No. 07/170,515, filed on Mar. 21, 1988, now abandoned.

(51) Int. Cl.⁷ .................................................. C12N 15/63
(52) U.S. Cl. ...................................................... 435/455
(58) Field of Search .............................. 435/320.1, 440, 435/455, 456, 69.1; 424/184.1, 188.1, 196.11, 199.1, 93.2, 93.21, 93.6; 514/44

(56) References Cited

U.S. PATENT DOCUMENTS

| 4,405,712 A | 9/1983 | Vande Woude et al. |
| 4,650,764 A | 3/1987 | Temin et al. |

(List continued on next page.)

FOREIGN PATENT DOCUMENTS

| AU | B-19201/88 | 1/1989 |
| EP | 0 178 220 A2 | 4/1986 |

(List continued on next page.)

OTHER PUBLICATIONS

Bachmann et al. Curr. Opin. Immunol. 6: 320–326, 1994.*

(List continued on next page.)

*Primary Examiner*—Remy Yucel
(74) *Attorney, Agent, or Firm*—Robert P. Blackburn; Donald Pochopien; Anne S. Dollard

(57) ABSTRACT

Recombinant retroviruses carrying a vector construct capable of preventing, inhibiting, stabilizing or reversing infectious, cancerous or auto-immune diseases are disclosed. More specifically, the recombinant retroviruses of the present invention are useful for (a) stimulating a specific immune response to an antigen or a pathogenic antigen; (b) inhibiting a function of a pathogenic agent, such as a virus; and (c) inhibiting the interaction of an agent with a host cell receptor. In addition, eucaryotic cells infected with, and pharmaceutical compositions containing such a recombinant retrovirus are disclosed. Various methods for producing recombinant retroviruses having unique characteristics, and methods for producing transgenic packaging animals or insects are also disclosed.

10 Claims, 44 Drawing Sheets

U.S. PATENT DOCUMENTS

| | | | |
|---|---|---|---|
| 4,663,281 A | 5/1987 | Gilles et al. | 435/69.1 |
| 4,677,064 A | 6/1987 | Mark et al. | |
| 4,708,818 A | 11/1987 | Montagnier et al. | |
| 4,725,669 A | 2/1988 | Essex et al. | |
| 4,738,922 A | 4/1988 | Haseltine et al. | 435/69.1 |
| 4,752,565 A | 6/1988 | Folks et al. | |
| 4,861,719 A | 8/1989 | Miller | |
| 4,868,116 A | 9/1989 | Morgan et al. | |
| 4,980,286 A | 12/1990 | Morgan et al. | |
| 4,980,289 A | 12/1990 | Temin et al. | |
| 5,026,635 A | 6/1991 | Ferguson et al. | 435/5 |
| 5,081,021 A | 1/1992 | Mizuno et al. | |
| 5,246,924 A | 9/1993 | Fox et al. | 514/50 |
| 5,304,489 A | 4/1994 | Rosen | 435/320.1 |
| 5,306,631 A | 4/1994 | Harrison et al. | 435/172.3 |
| 5,324,655 A | 6/1994 | Kriegler et al. | |
| 5,399,346 A | 3/1995 | Anderson et al. | 424/93.21 |
| 5,529,774 A | 6/1996 | Barba et al. | |
| 5,604,293 A | 2/1997 | Fiddes et al. | |
| 5,635,399 A | 6/1997 | Kriegler et al. | |
| 5,691,177 A | 11/1997 | Gruber et al. | 435/172.3 |
| 5,830,458 A | * 11/1998 | Gruber et al. | 424/93.2 |

FOREIGN PATENT DOCUMENTS

| | | |
|---|---|---|
| EP | 0 243 204 A2 | 10/1987 |
| EP | 0 288 163 A2 | 10/1988 |
| EP | 0 293 181 A1 | 11/1988 |
| EP | 0 334 301 A1 | 9/1989 |
| EP | 0 415 731 A2 | 3/1991 |
| EP | 0 476 953 A2 | 3/1992 |
| FR | 2 606 030 | 6/1988 |
| FR | 0 273 782 A1 | 7/1988 |
| WO | WO 85/05629 | 12/1985 |
| WO | WO 86/00922 | 2/1986 |
| WO | WO 86/00930 * | 2/1986 |
| WO | WO 89/01972 | 3/1989 |
| WO | WO 89/02468 | 3/1989 |
| WO | WO 89/05345 | 6/1989 |
| WO | WO 89/05349 | 6/1989 |
| WO | WO 89/07150 | 8/1989 |
| WO | WO 90/02806 | 3/1990 |
| WO | WO 90/07936 | 7/1990 |
| WO | WO 90/11092 | 10/1990 |
| WO | WO 91/02805 | 3/1991 |
| WO | WO 92/15693 | 9/1992 |
| WO | WO 93/02556 | 2/1993 |
| WO | WO 93/04167 | 3/1993 |
| WO | WO 93/07906 | 4/1993 |
| WO | WO 93/08844 | 5/1993 |
| WO | WO 93/10218 | 5/1993 |
| WO | WO 93/21959 | 11/1993 |
| WO | WO 94/21792 | 9/1994 |

OTHER PUBLICATIONS

Marshall, E.M. Science. vol. 269, pp. 1050–1055, Aug. 1995.*

Barinaga, M. Science. vol. 266, p. 1326, Nov. 1994.*

Crystal, R. Science. vol. 270, pp. 404–410, 1995.*

Jolly, D. Cancer Gene Therapy. vol. 1, No. 1, pp. 51–64, 1994.*

Orkin et al. NIH Report on Gene Therapy, Dec. 1995.*

Freidman, T. Scientific American. Jun. 1997, pp. 96–101.*

Verma et al. Nature. vol. 389, pp. 239–242, 1997.*

Nature Biotechnology, editorial, vol. 15, 1997.*

Ballay, et al., In vitro and in vivo synthesis of the hepatitis B virus surface antigen and of the receptor for polymerized human serum albumin from recombinant human adenoviruses, EMBO J., 4:3861–3865 (1985).

Hariharan, A vector for inducible production of retrovirus, Nucleic Acids Research, 16(19):9345 (1988).

Thummel, et al., Construction of Adenovirus Expression Vectors by Site–Directed In Vivo Recombination, J. Mol. Appl. Genet., 1(5):435–446 (1982).

Caruso et al., "Regression of established macroscopic liver metastases after in situ transduction of a suicide gene," Proc. Natl. Acad. Sci. USA, 90: 7024–7028 (Aug. 1993).

Chen et al., "Combination Suicide and Cytokine Gene Therapy for Hepatic Metastases of Colon Carcinoma: Sustained Antitumor Immunity Prolongs Animal Survival," Cancer Research, 56:3758–3762 (Aug. 15, 1996).

DiMaio et al., "Directed enzyme pro–drug gene therapy for pancreatic cancer in vivo," Surgery, 116:205–213 (Aug. 1994).

Hurford et al., "Gene therapy of metastatic cancer by in vivo retroviral gene targeting," Nature Genetics, 10:430–435 (Aug. 1995).

O'Malley et al., "Adenovirus–mediated Gene Therapy for Human Head and Neck Squamous Cell Cancer in a Nude Mouse Model," Cancer Research, 55:1080–1085 (Mar. 1, 1995).

O'Malley et al., "Combination Gene Therapy for Oral Cancer in a Murine Model," Cancer Research, 56:1737–1741 (Apr. 15, 1996).

Tanaka et al., "Adenovirus–mediated Prodrug Gene Therapy for Carcinoembryonic Antigen–producing Human Gastric Carcinoma Cells in Vitro," Cancer Research, 56:1341–1345 (Mar. 15, 1996).

Trinh et al., "Enzyme/Prodrug Gene Therapy: Comparison of Cytosine Deaminase/5–Fluorocytosine Versus Thymidine Kinase/Ganciclovir Enzyme/Prodrug Systems in a Human Colorectal Carcinoa Cell Line," Cancer Research, 55:4808–4812 (Nov. 1, 1995).

Yang et al., "Gene Therapy of Metastatic Pancreas Cancer with Intraperitoneal Injections of Concentrated Retroviral Herpes Simplex Thymidine Kinase Vector Supernatant and Ganciclovir," Annals of Surgery, 224(3):405–417 (Sep. 1996).

International Search Report, International Application No. PCT/US94/13304, International Filing Date Nov. 18, 1994.

Yamamoto et al., "Cloning and sequencing of mouse tyrosinase cDNA," Jpn. J. Genet, 62:271–274 (1987).

Kwon et al., "Sequence Analysis of Mouse Tyrosinase cDNA and the Effect of Melanotropin on its Gene Expression," Biochemical and Biophysical Research Communications, 153(3):1301–1309 (Jun. 30, 1988).

Ruppert et al., "Multiple transcripts of the mouse tyrosinase gene are generated by alternative splicing," The EMBO Journal, 7(9):2715–2722 (1988).

Ram et al., "Summary of Results and Conclusions of the Gene Therapy of Malignant Brain Tumors: Clinical Study," J. Neurosurg., 82:343A, Paper #708, (Feb. 1995).

Brodignon, Claudio, "Transfer of the HSV–TK Gene Into Donor Peripheral Blood Lymphocytes for in vivo Modulation of Donor Anti–Tumor Immunity After ALLO–BMT," Brit. J. of Haematology, 93:306 (Jun. 1996).

Mavilio et al., "Peripheral Blood Lymphocytes as Target Cells of Retroviral Vector–Mediated Gene Transfer," Blood, 83(7):1988–1997 (Apr. 1, 1994).

Bonini et al., "HSV–TK Gene Transfer into Donor Lymphocytes for Control of Allogenic Graft–Versus–Leukemia," *Science*, 276:1719–1724 (Jun. 13, 1997).

Lundwall et al., "Molecular cloning of human prostate specific antigen cDNA," *FEBS Letters*, 214(2):317–322 (Apr. 1987).

Schulz et al., "Sequence of cDNA clone encompassing the complete mature human Prostate Specific Antigen (PSA) and an unspliced leader sequence," *Nucleic Acids Research*, 16(13):6226 (1988).

Riegman et al., "Molecular Cloning and Characterization of Novel Prostate Antigen cDNA's," *Biochemical and Biophysical Research Communications*, 155(1):181–188 (Aug. 30, 1988).

Lundwall, Ake, "Characterization of the gene for Prostate-specific antigen, a human glandular kallikrein," *Biochemical and Biophysical Research Communications*, 161(3):1151–1159 (Jun. 30, 1989).

Calabretta et al., "Altered expression of $G_1$-specific genes in human malignant myeloid cells," *Proc. Natl. Acad. Sci USA*, 83:1495–1498 (Mar. 1986).

Huber et al., "Retroviral–mediated gene therapy for the treatment of hepatocellular carcinoma: An innovative approach for cancer therapy," *Proc. Natl. Acad. Sci. USA*, 48:8039–8043 (Sep. 1991).

Austin et al., "A First Step in the Development of Gene Therapy for Colorectal Carcinoma: Cloning, Sequencing, and Expression of *Escherichia coli* Cytosine Deaminase," *Molecular Pharmacology*, 43:380–387 (1993).

Huber et al., "In Vivo Antitumor Activity of 5–Flurocytosine on Human Colorectal Carcinoma Cells Genetically Modified to Express Cytosine Deaminase," *Cancer Research*, 53:4619–4626 (Oct. 1, 1993).

Huber et al., "Metabolism of 5–fluorocytosine to 5–fluorouracil in human colorectal tumor cells transducted with the cytosine deaminase gene: Significant antitumor effects when only a small percentage of tumor cells express cytosine deaminase," *Proc. Natl. Acad. Sci. USA*, 91:8302–8306 (Aug. 1994).

Sawyer et al., "Mapping of the Varicella Zoster Virus Deoxypyrimidine Kinase Gene and Preliminary Identification of its Transcript," *Virology*, 149:1–9 (1986).

Haj–Ahmad et al., "Development of a Helper–Independent Human Adenovirus Vector and Its Use in the Transfer of the Herpes Simplex Virus Thymidine Kinase Gene," *Journal of Virology*, 57(1)267–274 (Jan. 1986).

Chen et al., "Combination gene therapy liver metastasis of colon carcinoma in Vivo," *Proc. Natl. Acad. Sci. USA*, 92:2577–2581 (Mar. 1995).

Vile et al., "Systemic Gene Therapy of Murine Melanoma Using Tissue Specific Expression of the HSVtk Gene Involves an Immune Component," *Cancer Research*, 54:6228–6232 (1994).

Oldfield et al., "Gene Therapy for the Treatment of Brain Tumors Using Intra–Tumoral Transduction with the Thymidine Kinase Gene and Intravenous Ganciclovir," *Human Gene Therapy*, 4:39–69 (1993).

Hirochika et al., "Functional mapping of the human papillomavirus type 11 transcriptional enhancer and its interaction with the trans–acting E2 proteins," *Genes & Development*, 2:54–67 (1988).

Caruso, Manuel, "Gene therapy against cancer and HIV infection using the gene encoding herpes simplex virus thymidine kinase," *Molecular Medicine Today*, pp. 212–217 (May 1996).

Shibahara et al., "Cloning and expression of cDNA encoding mouse tyrosinase," *Nucleic Acids Research*, 14(6):2413–2427 (1986).

Ledley, Fred D., "Somatic gene therapy for human disease: Background and prospects. Part II," *The Journal of Pediatrics*, 110(2):167–174.

Sorge et al., "Complete correction of the enzymatic defect of type I Gaucher disease fibroblasts by retroviral–mediated gene transfer," *Proc. Natl. Acad. Sci. USA*, 84:906–909 (Feb. 1987).

Palmer et al., "Efficient retrovirus–mediated transfer and expression of a human adenosine deaminase gene in diploid skin fibroblasts from an adenosine deaminase–deficient human," *Proc. Natl. Acad. Sci. USA*, 84:1055–1059 (Feb. 1987).

Hwang et al., "Expression of Genes Introduced into Cells by Retroviral Infection Is More Efficient Than That of Genes Introduced into Cells by DNA Transfection," *Journal of Virology*, 50(2):417–424 (May 1984).

Davison et al., "The Complete DNA Sequence of Varicella–Zoster Virus," *J. Gen. Virol.*, 67:1759–1816 (1986).

Culver et al., "In Vivo Gene Transfer with Retroviral Vector–Producer Cells for Treatment of Experimental Brain Tumors," *Science*, 256:1550–1552 (Jun. 12, 1992).

Ram et al., "In Situ Retroviral–mediated Gene Transfer for the Treatment of Brain Tumors in Rats," *Cancer Research*, 53:83–88 (Jan. 1, 1993).

Cone et al., "High–efficiency gene transfer into mammalian cells: Generation of Helper–free recombinant retrovirus with broad mammalian host range," *Proc. Natl. Acad. Sci. USA*, 81:6349–6353 (Oct. 1984).

Berkner, "Development of Adenovirus Vectors for the Expression of Heterologous Gene," *BioTechniques*, 6(7):616–629 (1988).

Achour, et al., "Induction of Anti–gp160 Cytotoxic T Cells Cross–Reacting with Various V3 Loop P18 Peptides in Human Immunodeficiency Virus Type 1 Envelope–Immunized Individuals," *Journal of Virology*, 70(10):6741–6750 (Oct., 1996).

Miedema et al., "AIDS Pathogenesis: A Finite Immune Response to Blame?," *Science*, 272:505–506 (Apr. 26, 1996).

Rinaldo, et al., "High Levels of Anti–Human Immunodeficiency Virus Type 1 (HIV–1) Memory Cytotoxic T–Lymphocyte Activity and Low Viral Load Are Associated with Lack of Disease in HIV–1–Infected Long–Term Nonprogressors," *Journal of Virology*, 69(9):5838–5842 (Sep. 1995).

Ferbas, et al., "Rapid Evolution of Human Immunodeficiency Virus Strains with Increased Replicative Capacity during the Seronegative Window of Primary Infection," *Journal of Virology*, 70(10):7285–7289 (Oct., 1996).

O'Brien, et al., "Changes in Plasma HIV–1 RNA and CD4+ Lymphocyte Counts and Risk of Progression to Aids," *The New England Journal of Medicine*, 334(7):426–431 (Feb. 15, 1996).

Mellors, et al., "Prognosis in HIV–1 Infection Predicted by the Quantity of Virus in Plasma," *Science*, 272:1167–1170 (May 24, 1996).

Ho, "Viral Counts Count in HIV Infection," *Science,* 272:1124–1125 (May 24, 1996).
Ruiz, et al., "Quantitative HIV–1 RNA as a marker of clinical stability and survival in a cohort of 302 patients with a mean CD4 cell count of 300 x $10^6$/I," *AIDS* *10(11)*:F39–F44 (1996).
Ziegner, et al., "Cytotoxic T–lymphocyte induction in asymptomatic HIV–1–infected patients immunized with Retrovector®–transduced autologous fibroblasts expressing HIV–$1_{111B}$ Env/Rev proteins," AIDS:9(1):43–50 (1995).
Yang, et al., "Efficient Lysis of Human Immunodeficiency Virus Type 1–Infected Cells by Cytotoxic T Lymphocytes," *Journal of Virology,* 70(9):5799–5806 (Sep., 1996).
Joyner et al., "Construction and Transfer of Recombinant Retrovirus Clones Carrying the HSV–1 Thymidine Kinase Gene," The Ontario Cancer Institute, and Department of Medical Biophysics University of Toronto, Toronto, Canada, pp. 535–546 (1981).
Eglitis et al., "Gene Expression in Mice After High Efficiency Retroviral–Mediated Gene Transfer," *Science 230:*1395–1398 (Dec. 20, 1985).
Morin et al., "Recombinant adenovirus induces antibody response to hepatitis B virus surface antigen in hamsters," *Proc. Natl. Acad. Sci. USA 84:* 4626–4630 (Jul., 1987).
Mulligan, "The Basic Science of Gene Therapy," *Science 260:*926–932 (May 14, 1993).
Stratowa et al., "Recombinant retroviral DNA yielding high expression of hepatitis B surface antigen," *The EMBO Journal,* 1(12):1573–1578 (1982).
Davis et al., "Expression of hepatitis B surface antigen with a recombinant adenovirus," *Proc. Natl. Acad. Sci., USA* 82:7560–7564 (Nov., 1985).
Adam et al., "Identification of a Signal in a Murine Retrovirus That Is Sufficient for Packaging of Nonretroviral RNA into Virions," *J. Virology,* 62(10):3802–3806 (Oct., 1988).
Anderson F. W., "Human Gene Therapy," *Science,* 256:808–813 (May 8, 1992).
Baltimore, "Intracellular Immunization," *Nature,* 335:395–396 (1988).
Cepko et al., "Construction and Applications of a Highly Transmissible Murine Retrovirus Shuttle Vector," *Cell,* 37:1053–1062 (Jul., 1984).
Cone et al., "Regulated Expression of a Complete Human β–Globin Gene Encoded by a Transmissible Retrovirus Vector," *Mol. & Cell. Biol,* 7(2):887–897 (Feb., 1987).
Cournoyer et al., "Gene Therapy of the Immune System," *Ann. Rev. Immunol.,*11:297–329 (1993).
Danos et al., "Safe and Efficient Generation of Recombinant Retroviruses With Amphotropic and Ecotropic Host Ranges," *Proc. Nat'l Acad. Sci., USA,* 85:6460–6464 (Sep., 1988).
Dayton et al., "The Trans–Activator Gene of the Human T Cell Lymphotropic Virus Type III Is Required for Replication," *Cell,* 44:941–947 (Mar. 28, 1986).
Dzierzak et al., "Lineage–Specific Expression of A Human β–Globin Gene In Murine Bone Marrow Transplant Recipients Reconstituted With Retrovirus–transduced Stem Cells," *Nature,* 331:35–41 (Jan. 7, 1988).
Felber et al., "A Quantitative Bioassay For HIV–1 Based On Trans–Activation," *Science,* 239:184–187 (Jan. 8, 1988).
Felgner et al., "Lipofection: A Highly Efficient, Lipid–Mediated DNA–Transfection Procedure," *Proc. Nat'l Acad. Sci., USA,* 84:7413–7417 (Nov., 1987).

Frankel et al., "Dimerization of the Tat Protein from Human Immunodeficiency Virus: A Cysteine–Rich Peptide Mimics the Normal Metal–Linked Dimer Interface," *Proc. Nat'l Acad. Sci.,* USA, 85:6297–6300 (Sep., 1988).
Frankel et al., "Tat Protein From Human Immunodeficiency Virus Forms A Metal–Linked Dimer," *Science,* 240:70–73 (Apr., 1988).
Friedman et al., "Expression Of A Truncated Viral Trans–Activator Selectively Impedes Lytic Infection By Its Cognate Virus," *Nature,* 335:452–454 (Sep. 29, 1988).
Furman et al., "Inhibition of Herpes Simplex Virus–Induced DNA Polymerase Activity and Vital DNA Replication by 9–(2–Hydroxyethoxymethyl)guanine and Its Triphosphate," *J. Virology,* 32(1):72–77 (Oct., 1979).
Ganz et al., "Defensins Natural Peptide Antibiotics of Human Neutrophils," *J. Clin. Invest.,* 76:1427–1435 (Oct., 1985).
Goelz, S.E., "Hypomethylation of DNA from Benign and Malignant Human Colon Neoplasms," *Science,* 228:187–190 (Apr. 12, 1985).
Graham et al., "A New Technique for the Assay of Infectivity of Human Adenovirus 5 DNA," *J. Virology,* 52:456–467 (1973).
Guild et al., "Development of Retrovirus Vectors Useful for Expressing Genes in Cultured Murine Embryonal Cells and Hematopoietic Cells In Vivo," *J. Virol.,* 62(10):3795–3801 (1988).
Haynes, B.F., "Scientific and Social Issues of Human Immunodeficiency Virus Vaccine Development," *Science,* 260:1279–1286 (May 28, 1993).
Hirsch, M.S., "Aids Commentary: Azidothymidine," *J. Infect. Dis.,* 157(3):427–431 (1988).
Ho et al., "A T–Cell–Specific Transcriptional Enhancer Element 3' of $C_\alpha$ in the Human T–Cell Receptor a Locus," *Proc. Nat'l Acad. Sci.,* USA, 86:6714–6718 (Sep., 1989).
Johnston et al.,"Present Status and Future Prospects for HIV Therapies," *Science,* 260:1286–1293 (May 28, 1993).
Kantoff et al., "Correction of Adenosine Dearninase Deficiency in Cultured Human T and B Cells by Retrovirus–mediated Gene Transfer," *Proc. Nat'l Acad. Sci.,* USA, 83:6563–6567 (Sep., 1986).
Kriegler et al., "Transformation Mediated by the SV40 T Antigens: Separation of the Overlapping SV40 Early Genes with a Retroviral Vector," *Cell,* 38:483–491 (Sep., 1984).
Malim et al., "The HIV–I rev trans–activator Acts Through a Structured Target Sequence to Activate Nuclear Export of Unspliced Vital mRNA," *Nature,* 338:254–257 (1989).
Maniatis et al., *Molecular Cloning: A Laboratory Manual,* Cold Spring Harbor Laboratory, Cold Spring Harbor Press, pp. 22–26 (1982).
Maniatis et al., "Regulation of Inducible and Tissue–Specific Gene Expression," *Science,* 236:1237–1245 (Jun. 5, 1987).
Mansour et al., "Disruption Of The Proto–Oncogene int–2 In Mouse Embryo–Derived Stem Cells: A General Strategy For Targeting Mutations To Non–Selectable Genes," *Nature,* 336:348–352 (Nov., 1988).
Mariman, E.C.M., "New Strategeoies for AIDS therapy and Prophylaxis," *Nature,* 318:414 (1985).
Miller et al., "Redesign Of Retrovirus Packaging Cell Lines To Avoid Recombination Leading To Helper Virus Production," *Mol. Cell. Biol.,* 6(8):2895–2902 (Aug., 1986).
Mitsuya et al., "Strategies for Antiviral Therapy in AIDS," *Nature,* 325:773–778 (Feb. 26, 1987).

Moolten, F.L., "An Alternative to the Magic Bullet Paradigm for Specific Cancer Therapy," *Medical Hypotheses*, 24:43–51 (1987).

Moolten, F.L., "Tumor Chemosensitivity Conferred by Inserted Herpes Thymidine Kinase Genes: Paradigm for a Prospective Cancer Control Strategy," *Cancer Research*, 46:5276–5281 (Oct., 1986).

Muesing et al., "Regulation of mRNA Accumulation by a Human Immunodeficiency Virus Trans–Activator Protein," *Cell*, 48:691–701 (1987).

Nabel et al., "Alternative Mechanisms for Activation of Human Immunodeficiency Virus Enhancer in T Cells," *Science*, 239:1299–1302 (1988).

Overhauser et al., "Generation of Glucocorticoid–Responsive Moloney Murine Leukemia Virus by Insertion of Regulatory Sequences from Murine Mammary Tumor Virus into the Long Terminal Repeat," *J. Virol.*, 54(1):133–144 (1985).

Palmiter et al., "Cell Lineage Ablation In Transgenic Mice By Cell–Specific Expression Of A Toxin Gene," *Cell*, 80:435–443 (1987).

Patarca et al., "rpt–1, An Intracellular Protein From Helper/Inducer T Cells That Regulates Gene Expression of Interleukin 2 Receptor and human Immunodeficiency Virus Type 1," *Proc. Nat'l Acad. Sci.*, 85:2733–2737 (1988).

Peterlin et al., "Elevated Levels of mRNA Can Account for the Trans–activation of Human Immunodeficiency Virus," *Proc. Nat'l Acad. Sci.*, USA, 83:9734–9738 (Dec., 1986).

Phelps et al., "The Human Papillomavirus Type 16 E7 Gene Encodes Transactivation and Transformation Functions Similar to Those of Adenovirus EIA," *Cell*, 53:539–547 (May 20, 1988).

Piatak et al., "Expression of Soluble and Fully Functional Ricin A Chain in *Escherichia coli* is Temperature–Sensitive," *J. Biol. Chem.*, 263(10):4837–4843 (1988).

Selsted et al., "Primary Structures of Three Human Neutrophil Defensins," *J. Clin. Invest.*, 76:1436–1439 (Oct., 1985).

Shinnick et al., "Nucleotide Sequence of Moloney Murine Leukaemia Virus," *Nature*, 293:543–548 (1981).

Smith et al., "Blocking of HIV–I Infectivity by a Soluble, Secreted Form of the Antigen," *Science*, 238:1704–1707 (Dec. 18, 1987).

Sodroski et al., "Trans–Acting Transcriptional Regulation of Human T–Cell Leukemia Virus Type III Long Terminal Repeat," *Science*, 22:171–173 (Jan. 11, 1985).

Sodroski et al., "Location Of The Trans–Activating Region On The Genome of Human T–Cell Lymphotropic Virus Type Ill," *Science*, 229:74–77 (Jul. 5, 1985).

Tellier et al., "New Strategies for AIDS Therapy and Prophylaxis," *Nature*, 318:414 (1985).

Treisman, "Identification of a Protein–Binding Site That Mediates Transcriptional Response of the C–fos Gene to Serum Factors," *Cell*, 46:567–574 (Aug. 15, 1986).

Van Beveran et al., "Nucleotide Sequence of the Genome of a Murine Sarcoma Virus," *Cell*, 27:97–108 (1981).

Walbot et al., "Plant Development and Ribozymes for Pathogens," *Nature*, 334:196–197 (Jul. 21, 1988).

Wasmoen et al., "Biochemical and Amino Acid Sequence Analysis of Human Eosinophil Granule Major Basic Protein," *J. Biol. Chem.*, 263:12559–12563 (1988).

Yee et al., "Gene Expression From Transcriptionally Disabled Retroviral Vectors," *Proc. Nat'l Acad. Sci.*, USA, 84:5197–5201 (Aug., 1987).

Yu et al., "Self–Inactivating Retroviral Vectors Designed for Transfer of Whole Genes into Mammalian Cells," *Proc. Nat'l Acad. Sci.*, USA, 83:3194–3198 (May, 1986).

Maxwell et al., "Regulated Expression of a Diptheria Toxin A–Chain Gene Transfected Into Human Cells: Possible Strategy For Inducing Cancer Cell Suicide," *Cancer Research*, 46:4660–4664 (1986).

Maxwell et al., "Regulated Expression of a Transfected Toxin Gene," *J. Cell. Biochem.*, Supplement 10D:39 (Abstract N93) (1986).

Maxwell et al., "HTLV–Regulated Expression of a Transfected Diphtheria Toxin Gene," *J. Cell Biochem.*, Supplement 11D:67 (Abstract P314) (1987).

Harrison et al., "Toward HIV–Regulated Expression of a Diptheria Toxin A Gene In Transfected Cells," *J. Cell. Biochem.*, Supplement 13B:302 (Abstract G418) (Jan. 21, 1989).

Verma et al., "Expression and Regulation of Rat Growth Hormone Gene in Mouse Fibroblasts," In: *Eukaryotic Viral Vectors*, Gluzman, Y. (Ed.), Cold Spring Harbor Laboratory, pp. 159–164 (1982).

Arnold et al., "Vaccine Development for Aids Through Molecular Surgery of a Human Common Cold Virus Surface," *J. Cell. Biochem.*, L401:145 (1990).

Buseyne et al., "Detection of HIV–Specific Cell–mediated Cytotoxicity in the Peripheral Blood from Infected Children," *J. Immunology*, 150(8):3569–3581 (1993).

Carmichael et al., "Quantitative Analysis of the Human Immunodeficiency Virus Type 1 (HIV–1)–Specific Cytotoxic T Lymphocyte (CTL) Response at Different Stages of HIV–1 Infection: Differential CTL Responses to HIV–1 and Epstein–Barr Virus in Late Disease," *J. Exp. Med.*, 177:249–256 (1993).

Chada et al., "Cross–Reactive Lysis of Human Targets Infected with Prototypic and Clinical Human Immunodeficiency Virus Type 1 (HIV–1) Strains by Murine Anti–HIV–1 IIIB env–Specific Cytotoxic T Lymphocytes," *J. Virol.* 67(6):3409–3417 (1993).

Dadaglio et al., "Enhancement of HIV–specific Cytotoxic T Lymphocytes Responses by Zidovudine (AZT) Treatment," *Clin. Ex. Immunol.*, 87:7–14 (1992).

De Baetselier et al., "Differential Expression of H–2 Gene Products in Tumour Cells is Associated with Their Metastatogenic Properties," *Nature*, 288:179–181 (1980).

Doherty et al., "Recombinant Vaccinia Viruses and the Development of Immunization Strategies Using Influenza Virus," *J. Inf. Disease*, 159(6):1119–1122 (1989).

Ellrodt et al., "The Hidden Dangers of AIDS Vaccination," *Nature*, 325:765 (1987).

Fauci et al., "Development and Evaluation of a Vaccine for Human Immunodeficiency Virus (HIV) Infection," *Ann. Intern. Med.*, 110:373–385 (1989).

Fisher–Hoch et al., "Protection of Rhesus Monkeys From Fatal Lassa Fever by Vaccination With a Recombinant Vaccinia Virus Containing the Lassa Virus Glycoprotein," *Proc. Nat'l Acad. Sci.*, USA, 86:317–321 (1989).

Holt et al., "Inducible Production of c–fos Antisense RNA Inhibits 3T3 Cell Proliferation," *Proc. Nat'l Acad. Sci.*, USA, 83:4794–4798 (1986).

Hu et al., "Effect of Immunization with a Vaccinia–HIV env Recombinant on HIV Infection of Chimpanzees," *Nature*, 328:721–723 (1987).

Hussey et al., "A Soluble CD4 Protein Selectively Inhibits HIV Replication and Syncytium Formation," *Nature*, 331:78–81 (1988).

Izant & Weintraub, "Constitutive and Conditional Suppression of Exogenous and Endogenous Genes by Anti–Sense RNA," *Science*, 229:345–352 (1985).

Joly et al., "Cell–Mediated Suppression of HIV–Specific Cytotoxic T Lymphocytes," *J. Immunol.*, 143(7):2193–2201 (1989).

Lathe et al., "Tumour Prevention and Rejection With Recombinant Vaccinia," *Nature*, 326:878–880 (1987).

Ledley et al., "Retroviral–mediated Gene Transfer of Human Phenylalanine Hydroxylase into NIH 3T3 and Hepatoma Cells," *Proc. Nat'l Acad. Sci.*, 83:409–413 (Jan., 1986).

Lotze et al., "Recent Advances in Cellular Immunology: Implication for Immunity to Cancer," *Immunology*, 11:190–193 (1990).

McCormick, D., "Human Gene Therapy: The First Round," *BioTechnology*, 3(8):689–693 (1985).

McCune et al., "Endoproteolytic Cleavage of gp160 Is Required for the Activation of Human Immunodeficiency Virus," *Cell*, 53:55–67 (1988).

Mercola et al., "Insertion of a New Gene of Viral Origin into Bone Marrow Cells of Mice," *Science*, 208:1033–1035 (1980).

Miedema et al., "Maintenance of High Level Cytotoxic T–Cell (CTL) Response in Long–Term Survivors of HIV Infection," *J. Cell. Biochem.*, Supplement 17D:75 (Abstract N350) (1993).

Mulligan, R.C., "Construction of Highly Transmissible Mammalian Cloning Vehicles Derived from Murine Retroviruses," *Experimental Manipulation of Gene Expression*, 8:155–173 (1983).

Mosier et al., "Resistance to Human Immunodeficiency Virus 1 Infection of SCID Mice Reconstituted With Peripheral Blood Leukocytes from Donors Vaccinated With Vaccinia gp160 and Recombinant gp160," *Proc. Nat'l Acad. Sci.*, USA, 90:2443–2447 (1993).

Newell et al., "Herpes Simplex Virus–Induced Stromal Keratitis: Role of T–Lymphocyte Subsets in Immunopathology," *J. Virol.*, 63(2):769–775 (1989).

Salk, J., "Prospects for the Control of AIDS by Immunizing Seropositive Individuals," *Nature*, 327:473–476 (1987).

Shinitzky et al., "Cancer Immunotherapy With Autologous and Allogeneic Vaccines: A Practical Overview," *EORTC Gentitourinary Group Monograph Basic Research and Treatment of Renal Cell Carcinoma Metastasis*, 9:95–125 (1990).

Strebel et al., "The HIV 'A' (sor) Gene Product is Essential for Virus Infectivity," *Nature*, 358:728–730 (1987).

Temin, H.M., "Retrovirus Vectors: Promise and Reality," *Science*, 246:983 (1989).

Torpey, III et al., "Effects of Adoptive Immunotherapy with Autologous CD8+ T Lymphocytes on Immunologic Parameters: Lymphocytes Subsets and Cytotoxic Activity," *Clinical Immunol. & Immunopath.*, 68(5):263–272 (1993).

Voss et al., "Potential Significance of the Cellular Immune Response against the Macaque Strain of Simian Immunodeficiency Virus ($SIV_{MAC}$) in Immunized and Infected Rhesus Macaques," *J. Gen. Virology*, 73:2273–2281 (1992).

Yasutomi et al., "Simian Immunodeficiency Virus–Specific CD8+ Lymphocyte Response in Acutely Infected Rhesus Monkeys," *J. Virol.*, 67(3):1707–1711 (1993).

Zagury et al., "Immunization Against AIDS in Humans," *Nature*, 326:249–250 (1987).

Czarniecki et al., "Synergistic Antiviral and Antiproliferative Activities of *Escherichia coli*–Derived Human Alpha, Beta, and Gamma Interferon," *J. of Virology*, 49(2):490–496 (Feb., 1984).

Davison et al., "The Complete DNA Sequence of Varicella–Zoster Virus," *J. Gen. Virol.*, 67:1759–1816 (1986).

Deen et al., "A Soluble Form of CD4 (T4) Protein Inhibits AIDS Virus Infection," *Nature*, 331:82–84 (Jan. 7, 1988).

Howell et al., "Gene Therapy for Thioguanine–resistant Human Leikemia," *Mol. Biol. Med.*, 4:157–168 (1987).

Katoh et al., "Inhibition of Retroviral Protease Activity by an Aspartyl Proteinase Inhibitor," *Nature*, 329–654–656 (Oct. 15, 1987).

Rein et al., "Myristylation Site in Pr65$^{gag}$ is Essential for Virus Particle Formation by Moloney Murine Leukemia Virus," *Proc. Nat'l Acad. Sci.*, USA, 83:7246–7250 (Oct., 1986).

Sleckman et al., "Expression and Function of CD4 in a Murine T–Cell Hybridoma," *Nature*, 328:351–353 (Jul. 23, 1987).

Stratowa et al., "Recombinant Retroviral DNA Yielding High Expression of Hepatitis B Surface Antigen," *EMBO J.*, 1(12):1573–1578 (1982).

Tabin et al., "Adaptation of a Retrovirus as a Eucaryotic Vector Transmitting the Herpes Simplex Virus Thymidine Kinase Gene," *Mol. & Cell. Biology*, 2(4):426–436 (Apr., 1982).

Temin, H.M., "Retrovirus Vectors for Gene Transfer: Efficient Integration Into and Expression of Exogenous DNA in Vertebrate Cell Genomes," In: *Gene Transfer*, Kucherlapati (Ed.), Plenum Press, New York, pp. 149–187 (1986).

Wachsman et al., "HTLV x Gene Mutants Exhibit Novel Transcriptional Regulatory Phenotypes," *Science*, 235:674–677 (Feb. 6, 1987).

Lang et al., "Expression of a Hemopoietic Growth Factor cDNA in a Factor–Dependent Cell Line Results in Autonomous Growth and Tumorigenicity," *Cell*, 43:531–542 (1985).

Besnard et al. "Selection against expression of the *Escherichia coli* gene gpt in hrpt +•mouse teratocarcinoma and hybrid cells," *Mol. Cell. Biol.*, 7(11):4139–4141 (Nov. 1987).

Borrelli et al., "Targeting of inducible toxic phenotype in animal cells," *Proc. Nat. Acad. Sci. USA*, 85:7572–7576 (Oct. 1988).

Kuriyama et al., "Gene therapy for the treatment of hepatoma by retroviral–mediated gene–transfer of the herpes–simplex virus thymidine kinase gene," *Int. Hepatol. Commun.* 1(5):253–259 (Oct. 1993).

Kuriyama et al. (b), "A potential approach for gene therapy targeting hepatoma using a liver–specific promoter on a retroviral vector," *Cell Struct. Func.*, 16:503–510 (1991).

Nelson, et al. "Gene replacement thereapy for inborn errors of purine metabolism," *Cold Spring Harbor Symp. Quant. Biol.* 51(2):1065–1071 (1986).

Pizer et al., "A mammalian cell line designed to test the mutagenic activity of anti–herpes nucleosides," *Int. J. Cancer*, 40:114–121 (1987).

Trucco, "Molecular mechanisms involved in the etiology and pathogenesis of autoimmune diseases," *Clin. Investig.* 70:756–765 (1992).

Bachmann, et al., "In Vivo versus In Vitro Assays for Assessment of T– and B– cell Function," *Immunological Techniques*, 6:320–326 (1994).

Chan et al., "Mammalian Sarcoma–Leukemia Viruses. I. Infection of Feline, Bovine, and Human Cell Cultures With Snyder–Theilen Feline Sarcoma Virus," *Journal of the Natl. Cancer Inst.*, 52(2):473–478 (Feb. 1974).

Donner, et al., "McDonough Feline Sarcoma Virus: Characterization of the Molecularly Cloned Provirus and Its Feline Oncogene (v–fms)," *Journal of Virology*, 41(2):489–500 (Feb. 1982).

Jolly, et al., "Variable Stability of a Selectable Provirus After Retroviral Vector Gene Transfer Into Human Cells," *Molecular and Cellular Biology*, 6(4):1141–1147 (Apr. 1986).

Lee, Robert E., "Gene Therapy: clipping the wings of nature's own gene transfer vectors," *Can. Med. Assoc. J.*, 134:311–313 (Feb. 15, 1986).

Ruscetti, et al., "Three Independent Isolates of Feline Sarcoma Virus Code for Three Distinct gag–x Polyproteins," *Journal of Virology*, 35(1):259–264 (Jul. 1980).

Suter, et al., "Cytotoxic Immune Response of Puppies to Feline Sarcoma Virus Induced Tumors," *Veterinary Immunology and Immunopathology*, 7:131–138 (1984).

Willis, et al., "Partial Phenotypic Correction of Human Lesch–Nyhan (Hypoxanthine–Guanine Phosphoribosyl-transferase–deficient) Lymphoblasts with a Transmissible Retroviral Vector," *The Journal of Biological Chemistry*, 259(12):7842–7849 (Jun. 25, 1984).

Klein, G., "Tumor Antigens," *Ann. Rev. Microbiol.* 20:223–252 (1966).

Hellström and Hellström, "Cellular Immunity Against Tumor Antigens," *Adv. Cancer Res.* 12:167–223 (1969).

Bishop, J.M., "Cancer Genes Come Of Age," *Cell* 32:1018–1020 (1983).

Hellström and Hellström, "Oncogene–associated Tumor Antigens as Targets for Immunotherapy," *FASEB J.* 3:1715–1722, (1989).

Miller, et al., "Treatment of B–Cell Lymphoma With Monoclonal Anti–Idiotype Antibody," *New England J. Med.* 306:517–522, (1982).

Bartram et al., "Translocation of c–abl Oncogene Correlates with the Presence of a Philadelphia Chromosome in chronic Myelocytic Leukaemia," *Nature* 306:277–280 (1983).

Yasukawa and Zarling, "Human Cytotoxic T Cell Clones Directed Against Herpes Simplex Virus–Infected Cells. III. Analysis of Viral Glycoproteins Recognized by CTL Clones by Using Recombinant Herpes Simplex Viruses," *J. Immunol.* 134(4):2679–2682, 1985.

Zarling, et al., "Human Cytotoxic T Cell Clones Directed Against Herpes Simplex Virus–Infected Cells. IV. Recognition and Activation by Cloned Glycoproteins gB and gD," *J. Immunol.* 136(12):4669–4673 (1986).

Zarling, et al., "Herpes Simplex Virus (HSV)–Specific Human T–Cell Clones Recognize HSV Glycoprotein D Expressed by a Recombinant Vaccinia Virus," *J. Virol.* 59(2):506–509 (1986).

Torseth, et al., "Native and Recombinant Herpes Simplex Virus Type 1 Envelope Protein Induce Human Immune T–Lymphocyte Responses," *J. Virol.* 61(5):1532–1539 (1987).

Aldovini et al., *Nature* 351:479–482, 1991.
Altmann, *Nature* 338:512–514, 1989.
Ameisen et al., *Immunology Today* 12:102–105, 1991.
Anderson et al., *Som. Cell and Mol. Genetics* 15:215–227, 1989.
Anderson, *Science* 226:401–409, 1984.
Armentano et al., *J. Virology* 61:1647–1650, 1987.
Baltimore, *Nature* 335:395–396, 1988.
Barnd et al., *PNAS* 86:7159–7163, 1989.
Berkner, *Biotechniques* 6:616–629, 1988.
Bernards et al., *Cell* 47:667–674, 1986.
Bernards et al., *PNAS* 84:6854–6858, 1987.
Bix et al., *Nature* 349:329–331, 1991.
Bolognesi et al., *Cancer Research (Suppl.)* 45:4700s–4705s, 1985.
Braakman et al., *Int. J. Cancer* 46:475–480, 1990.
Braciale et al., *Immunology Reviews* 98:95–114, 1987.
Bubenik et al., *Immunology Letters* 19:279–282, 1988.
Carey, *Business Week*, pp. 133, 136, May 1, 1989.
Carr et al., *Blood* 62:180–185, 1983.
Cepko et al., *Cell* 37:1053–1062, 1984.
Cepko, *Neuron* 1:345–353, 1988.
Chakrabarti et al., *Nature* 320:535–537, 1986.
Cline et al., *Nature* 284:422–425, 1980.
Collins et al., *J. Cell. Physiology* 137:293–298, 1988.
Cone et al., *Endocrinology* 123:: 2067–2074, 1988.
Cone et al., *PNAS* 81:6349–6353, 1984.
Cortes et al., *J. Surg. Onco.* 25:289–295, 1984.
Crowley et al., *Cancer Research* 50:492–498, 1990.
Culliton, News and Comment, *Science* 246:746–751, 1989.
Dallo et al., *Virology* 173:323–329, 1989.
Earl et al., *J. Virology* 65:31–41, 1991.
Embretson et al., *J. Virology* 60:662–668, 1986.
Episkopou et al., *PNAS* 81:4657–4661, 1984.
Estin et al., *PNAS* 85:1052–1056, 1988.
Evans et al., *Nature* 339:385–388, 1989.
Faraji–Shadan et al., *Medical Hypothesis* 32:81–84, 1990.
Flexner et al., *Virology* 166:339–349, 1988.
Friedmann, *Ann. N.Y. Acad. Sci.* 265:141–152, 1975.
Friedmann, *Science* 244:1275–1281, 1989.
Gansbacher et al., *Cancer Research* 50:7820–7825, 1990.
Gattoni–Celli et al., *PNAS* 85:8543–8547, 1988.
Gilboa et al., *BioTechniques* 4:504–512, 1986.
Gilboa, *The Biology of Hematopoiesis*, pp. 301–311, 1990.
Gruber et al., *Science* 230:1057–1061, 1985.
Guarini et al., *Cancer Immunol. Immunother.* 30:262–268, 1989.
Hatzoglou et al., *J. Biol. Chem.* 263:17798–17808, 1988.
Haynes et al., *Science* 260:1279–1286, 1993.
Hellerman et al., *PNAS* 81:5340–5344, 1984.
Hester et al., *J. Nat. Cancer Inst.* 82:1209–1214, 1990.
Hoffenbach et al., *Journal of Immunology* 142:452–462, 1989.
Hu et al., *Virology* 179:321–329, 1990.
Hunt et al., *J. Virology* 62:3014–3019, 1988.
Isobe et al., *J. Nat. Cancer Inst.* 81:1823–1828, 1989.
Jaroff, *Time*, pp. 74–76, Sep. 24, 1990.
Johnston et al., *Science* 260:1286–1293, 1993.
Jolly et al., *Biotechnology Therapeutics* 2(1–2):179–193, 1990–1991.
Joyner et al., *Developmental Biology Using Purified Genes*, Academic Press, 1981.
Joyner et al., *Nature* 305:556–558, 1983.
Kantoff et al., *J. Exp. Med.* 166:219–234, 1987.
Kasid et al., *PNAS* 87:473–477, 1990.
Kast et al., *Cell* 59:603–614, 1989.
Keller et al., *Nature* 318:149–154, 1985.

Klavinskis et al., *J. Virol. 63:*4311–4316, 1989.
Koenig et al., *J. Immunol. 145:*127–135, 1990.
Kohn, *Blood Cells 13:*285–298, 1987.
Korman et al., *PNAS 84:*2150–2154, 1987.
Kourilsky et al., *Adv. in Immunol. 45:*107–193, 1989.
Ledley, *J. Pediatrics 110:*1–8, 1987.
Lee, *Can. Med. Assoc. J. 134:*311–313, 1986.
Linial et al., *Cell 15:*1371–1381, 1978.
Linial, *J. Virology 38:*380–382, 1981.
Lotteau et al., *J. Exp. Med. 169:*351–356, 1989.
Luytjes et al., *Cell 59:*1107–1113, 1989.
Mason et al., *Science 234:*1372–1378, 1986.
McCune et al., *Cancer Immunol. Immunother. 32:*62–66, 1990.
McMichael et al., *The New England J. Med. 309:*13–17, 1983.
Merz, *JAMA 257:*150–151, 1987.
Michel et al., *Eur. J. Immunol. 18:*1917–1924, 1988.
Miller et al., *Mol. And Cell. Biol. 5:*431–437, 1985.
Miller et al., *Mol. And Cell. Biol. 6:*2895–2902, 1986.
Miller et al., *PNAS 80:*4709–4713, 1983.
Miller et al., *Science 225:*630–632, 1984.
Miller, *Human Gene Therapy 1:*5–14, 1990.
Morgan et al., *Science 237:*1476–1479, 1987.
Morrow, *Ann. N.Y. Acad. Sci. 265:*13–21, 1975.
Nabel et al., *Science 244:*1342–1344, 1989.
Nixon et al., *Nature 336::* 484–487, 1988.
Overell et al., *Mol. And Cell. Biol. 8:*1803–1808, 1988.
Palmer et al., *PNAS 88:*1330–1334, 1991.
Panicali et al., *PNAS 80:*5364–5368, 1983.
Plata et al., *Nature 328:*348–351, 1987.
Redfield et al., *The New England J. Med. 324:*1677–1684, 1991.
Reif, *Cancer Research 45:*25–31, 1985.
Reimann et al., *J. Immunol. Methods 89:*93–101, 1986.
Rosenberg et al., *The New England J. Med. 323:*570–578, 1990.
Rosenfeld et al., *Science 252:*431–434, 1991.
Rouse et al., *Rev. Infect. Dis. 10:*16–33, 1988.
Rubenstein et al., *PNAS 81:*7137–7140, 1984.
Ruprecht et al., *PNAS 87:*5558–5562, 1990.
Sabin et al., *J. Biol. Standardization 1:*115–118, 1973.
Saito et al., *Immunological Reviews 101:*81–193, 1988.
Shimotohno et al., *Cell 26:*67–77, 1981.
Siu et al., *J. Immunology 143:*3813–3820, 1989.
Smith et al., *PNAS 86:*5557–5561, 1989.
St. Louis et al., *PNAS 85:*3150–3154, 1988.
Stover et al., *Nature 351:*456–460, 1991.
Strair et al., *J. Virology 62:*4756–4759, 1988.
Stuhlmann et al., *PNAS 81:*7151–7155, 1984.
Takahashi et al., *PNAS 85:*3105–3109, 1988.
Takahashi et al., *Science 246:*118–121, 1989.
Tellier et al., *Nature 318:*414, 1985.
Thomason and Booth, *Amer. J. Physiology 258:*C578–C581, 1990.
Townsend et al., *Cell 42:*457–467, 1985.
Traversari et al., *J. Immunol. 142:*2887–2894, 1989.
Van Den Eynde et al., *Int. J. Cancer 44:*634–640, 1989.
Verma, *Scientific American 262:*68–72, 81–84, 1990.
Walker et al., *Nature 328:*345–348, 1987.
Walker et al., *Science 240:*64–66, 1988.
Wallich et al., *Nature 315:*301–305, 1985.
Warner et al., *AIDS Research & Human Retroviruses 7(8):*645–655, 1991.
Watanabe et al., *Mol. And Cell. Biol. 3:*2241–2249, 1983.
Watanabe et al., *PNAS 79:*5986–5990, 1982.
Weber and Jay, *Curr. Top. Microbiol. Immunol. 137:*140–147, 1988.
Weber et al., *J. Exp. Med. 166:*1716–1733, 1987.
Wei et al., *J. Virology 39:*935–944, 1981.
Weis et al., *Mol. & Cell. Biol. 5:*1379–1384, 1985.
Weis et al., *PNAS 81:*4879–4883, 1984.
Wilson et al., *Science 244:*1344–1346, 1989.
Wilson et al., *Science 248:*1413–1416, 1990.
Wolff et al., *PNAS 86:*9011–9014, 1989.
Wong et al., *Genes Dev. 1:*358–365, 1987.
Xu et al., *Virology 171:*331–341, 1989.
Yap et al., *Nature 273:*238–239, 1978.
Zarling et al., *J. Immunol. 139:*988–990, 1987.
Zarling et al., *Nature 323:*344–346, 1986.
Zbar et al., *Cancer Research 43:*46–53, 1983.
Zinkernagel et al., *J. Exp. Med. 145:*644–651, 1977.
Zwiebel et al., *Ann. N.Y. Acad. Sci. 618:*394–404, 1990.

\* cited by examiner

62/3

53-7

51-1

VECTORS EXPRESSING MLV VIRAL PROTEINS

SCV 10

1.

p CMV env Am Dra

2.

p CMV env AM Nhe

3.

p MLP env Am Sph

4.

p CMV Xeno

5.

p CMV MCF

6.

p LARNL

7.

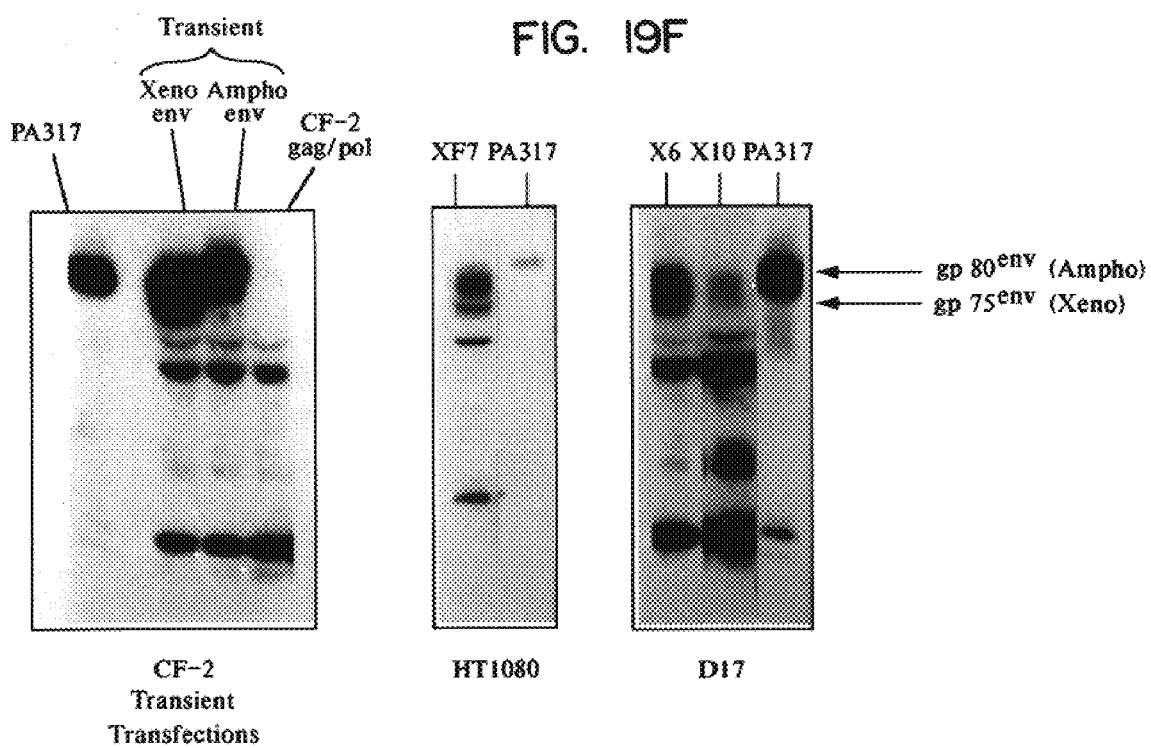

HT1080 CMV MCF-Transfected Clones

METHOD FOR INHIBITING HUMAN TUMOR CELLS

CROSS-REFERENCE TO RELATED APPLICATIONS

This application is a division of 08/344,743, filed Nov. 23, 1994, which is a continuation of 08/139,994, filed Oct. 20, 1993, now abandoned, which is a continuation of 07/965,084, filed Oct. 22, 1992, now abandoned, which is a continuation of 07/586,603, filed Sep. 21, 1990, now abandoned, which is a continuation-in-part of 07/565,606, filed Aug. 10, 1990, now abandoned, which is a continuation-in-part of 07/395,932, filed Aug. 18, 1989, now abandoned, which is a continuation-in-part of 07/170,515, filed Mar. 21, 1988, now abandoned.

TECHNICAL FIELD

The present invention relates generally to retroviruses, and more specifically, to recombinant retroviruses which are capable of delivering vector constructs to susceptible target cells. These vector constructs are typically designed to express desired proteins in target cells, including proteins which stimulate immune activity or which are conditionally active in defined cellular environments. In these respects the retrovirus carrying the vector construct is capable of directing an immune or toxic reaction against the target cell.

BACKGROUND OF THE INVENTION

Although bacterial diseases are, in general, easily treatable with antibiotics, very few effective treatments or prophylactic measures exist for many viral, cancerous, and other nonbacterial diseases, including genetic diseases. Traditional attempts to treat these diseases have employed the use of chemical drugs. In general, these drugs have lacked specificity, exhibited high overall toxicity, and thus have been therapeutically ineffective.

Another classic technique for treating a number of nonbacterial diseases involves the elicitation of an immune response to a pathogenic agent, such as a virus, through the administration of a noninfectious form of the agent, such as a killed virus, thereby providing antigens from the pathogenic agent which would act as an immuno-stimulant.

A more recent approach for treating viral diseases, such as acquired immunodeficiency syndrome (AIDS) and related disorders, involves blocking receptors on cells susceptible to infection by HIV from receiving or forming a complex with viral envelope proteins. For example, Lifson et al. (*Science* 232:1123–1127, 1986) demonstrated that antibodies to CD4 (T4) receptors inhibited cell fusion (syncytial) between infected and noninfected CD4 presenting cells in vitro. A similar CD4 blocking effect using monoclonal antibodies has been suggested by McDougal et al. (*Science* 231:382–385, 1986). Alternatively, Pert et al. (*Proc. Natl. Acad. Sci. USA* 83:9254–9258, 1986) have reported the use of synthetic peptides to bind T4 receptors and block HIV infection of human T-cells, while Lifson et al. (*J. Exm. Med.* 164:2101, 1986) have reported blocking both syncytia and virus/T4 cell fusion by using a lectin which interacts with a viral envelope glycoprotein, thereby blocking it from being received by CD4 receptors.

A fourth, recently suggested technique for inhibiting a pathogenic agent, such as a virus, which transcribes RNA is to provide antisense RNA which complements at least a portion of the transcribed RNA, and binds thereto, so as to inhibit translation (To et al., *Mol. Cell. Biol.* 6:758, 1986).

However, a major shortcoming of the techniques described above is that they do not readily lend themselves to control as to the time, location or extent to which the drug, antigen, blocking agent or antisense RNA are utilized. In particular, since the above techniques require exogenous application of the treatment agent (i.e., exogenous to the sample in an in vitro situation), they are not directly responsive to the presence of the pathogenic agent. For example, it may be desirable to have an immunostimulant expressed in increased amounts immediately following infection by the pathogenic agent. In addition, in the case of antisense RNA, large amounts would be required for useful therapy in an animal, which under current techniques would be administered without regard to the location at which it is actually needed, that is, at the cells infected by the pathogenic agent.

As an alternative to exogenous application, techniques have been suggested for producing treatment agents endogenously. More specifically, proteins expressed from viral vectors based on DNA viruses, such as adenovirus, simian virus 40, bovine papilloma, and vaccinia viruses, have been investigated. By way of example, Panicali et al. (*Proc. Natl. Acad. Sci. USA* 80:5364, 1983) introduced influenza virus hemagglutinin and hepatitis B surface antigens into the vaccinia genome and infected animals with the virus particles produced from such recombinant genes. Following infection, the animals acquired immunity to both the vaccinia virus and the hepatitis B antigen.

However, a number of difficulties have been experienced to date with viral vectors based on DNA viruses. These difficulties include (a) the production of other viral proteins which may lead to pathogenesis or the suppression of the desired protein; (b) the capacity of the vector to uncontrollably replicate in the host, and the pathogenic effect of such uncontrolled replication; (c) the presence of wild-type virus which may lead to viremia; and (d) the transitory nature of expression in these systems. These difficulties have virtually precluded the use of viral vectors based on DNA viruses in the treatment of viral, cancerous, and other nonbacterial diseases, including genetic diseases.

Due to the nontransitory nature of their expression in infected target cells, retroviruses have been suggested as a useful vehicle for the treatment of genetic diseases (for example, see F. Ledley, *The Journal of Pediatrics* 110:1, 1987). However, in view of a number of problems, the use of retroviruses in the treatment of genetic diseases has not been attempted. Such problems relate to (a) the apparent need to infect a large number of cells in inaccessible tissues (e.g., brain); (b) the need to cause these vectors to express in a very controlled and permanent fashion; (c) the lack of cloned genes; (d) the irreversible damage to tissue and organs due to metabolic abnormalities; and (e) the availability of other partially effective therapies in certain instances.

In addition to genetic diseases, other researchers have contemplated using retroviral vectors to treat nongenetic diseases (see, for example, EP 243,204 Cetus Corporation; Sanford, *J. Theor. Biol.* 130:469, 1988; Tellier et al., *Nature* 318:414, 1985; and Bolognesi et al., *Cancer Res.* 45:4700, 1985).

Tellier et al. suggested protecting T-cell clones by apparently infecting stem cells with "defective" HIV having a genome which could express antisense RNA to HIV RNA. Bolognesi et al. have suggested the concept of generating a nonvirulent HIV strain to infect stem cells so that T4 cells generated therefrom would carry interfering, nonvirulent forms of virus and thereby protect those cells from infection by virulent HIV. However, it would appear that the "attenuated" or "defective" HIV viruses used in both of the foregoing papers could reproduce (i.e., are not replication defective) such that the resulting viruses could infect other cells, with the possibility of an increased risk of recombination with previously present HIV or other sequences, leading to loss of attenuation. Non-nonreplicative forms would necessitate a defective helper or packaging line for HIV. However, since the control of HIV gene expression is complex, such cells have to date not been constructed. Furthermore, since the infecting attenuated or defective virus is not chimeric (a "nonchimeric" retrovirus being one with substantially all of its vector from the same retrovirus species), even if they were made replication defective (for example, by deletion from their genomes of an essential element), there still exists a significant possibility for recombination within the host cells with resultant production of infectious viral particles.

Although Sanford (*J. Theor. Biol.* 130:469, 1988) has also proposed using a genetic cure for HIV, he notes that due to the potential that exists for creating novel virulent viruses via genetic recombination between natural AIDS virus and therapeutic retroviral vectors carrying anti-HIV genes, retroviral gene therapy for AIDS may not be practical. Similarly, while McCormick & Kriegler (EP 243,204 A2) have proposed using retroviral vectors to deliver genes for proteins, such as tumor necrosis factor (TNF), the techniques they describe suffer from a number of disadvantages.

SUMMARY OF THE INVENTION

Briefly stated, the present invention provides recombinant retroviruses carrying a vector construct capable of preventing, inhibiting, stabilizing or reversing infectious, cancerous, auto-immune or immune diseases. Such diseases include HIV infection, melanoma, diabetes, graft vs. host disease, Alzheimer's disease, and heart disease.

The present invention is directed, in part, toward methods for (a) stimulating a specific immune response, either humoral or cell-mediated, to an antigen or pathogenic antigen; (b) inhibiting a function of a pathogenic agent, such as a virus; and (c) inhibiting the interaction of an agent with a host cell receptor, through the use of recombinant retroviruses.

More specifically, within one aspect of the present invention, a method for stimulating a specific immune response is provided, comprising infecting susceptible target cells with recombinant retroviruses carrying a vector construct that directs the expression of an antigen or modified form thereof in infected target cells. For purposes of the present invention, the term "infecting" includes the introduction of nucleic acid sequences through viral vectors, transfection or other means, such as microinjection, protoplast fusion, etc. The introduced nucleic acid sequences may become integrated into the nucleic acid of the target cell. Expression of the vector nucleic acid encoded protein may be transient or stable with time. Where an immune response is to be stimulated to a pathogenic antigen, the recombinant retrovirus is preferably designed to express a modified form of the antigen which will stimulate an immune response and which has reduced pathogenicity relative to the native antigen. This immune response is achieved when cells present antigens in the correct manner, i.e., in the context of the MHC class I and/or II molecules along with accessory molecules such as CD3, ICAM-1, ICAM-2, LFA-1, or analogs thereof (e.g., Altmann et al., *Nature* 338:512, 1989). Cells infected with retroviral vectors are expected to do this efficiently because they closely mimic genuine viral infection.

This aspect of the invention has a further advantage over other systems that might be expected to function in a similar manner, in that the presenter cells are fully viable and healthy, and no other viral antigens (which may well be immunodominant) are expressed. This presents a distinct advantage since the antigenic epitopes expressed can be altered by selective cloning of subfragments of the gene for the antigen into the recombinant retrovirus, leading to responses against immunogenic epitopes which may otherwise be overshadowed by immunodominant epitopes. Such an approach may be extended to the expression of a peptide having multiple epitopes, one or more of the epitopes being derived from different proteins. Further, this aspect of the invention allows efficient stimulation of cytotoxic T lymphocytes (CTL) directed against antigenic epitopes, and peptide fragments of antigens encoded by sub-fragments of genes, through intracellular synthesis and association of these peptide fragments with MHC Class I molecules. This approach may be utilized to map major immunodominant epitopes for CTL. In addition, the present invention provides for a more efficient presentation of antigens through the augmentation or modification of the expression of presenting accessory proteins (e.g., MHC I, ICAM-1, etc.) in antigen presenting cells. Such an approach may involve a recombinant retrovirus carrying a vector construct which directs expression of both an antigen (e.g., a tumor antigen) and an MHC protein (e.g., Class I or II) capable of presenting the antigen (or a portion thereof) effectively to T lymphocytes so that it stimulates an immune response in an animal. This offers the advantage that antigen presentation may be augmented in cells (e.g., tumor cells) which have reduced levels of MHC proteins and a reduced ability to stimulate an immune response. The approach may additionally involve a recombinant retrovirus carrying a vector construct which directs expression of both an antigen and a protein stimulating increased MHC protein expression in cells (e.g., interferon). The retrovirus infected cells may be used as an immunostimulant, immunomodulator, or vaccine, etc.

An immune response can also be achieved by transferring to an appropriate immune cell (such as a T lymphocyte) the gene for the specific T-cell receptor which recognizes the antigen of interest (in the context of an appropriate MHC molecule if necessary), for an immunoglobulin which recognizes the antigen of interest, or for a hybrid of the two which provides a CTL response in the absence of the MHC context.

In the particular cases of disease caused by HIV infection, where immunostimulation is desired, the antigen generated from the recombinant retroviral genome is of a form which will elicit either or both an HLA class I- or class II-restricted immune response. In the case of HIV envelope antigen, for example, the antigen is preferably selected from gp 160, gp 120, and gp 41, which have been modified to reduce their pathogenicity. In particular, the selected antigen is modified to reduce the possibility of syncytia, to avoid expression of epitopes leading to a disease enhancing immune response, to remove immunodominant, but strain-specific epitopes or to present several strain-specific epitopes, and allow a response capable of eliminating cells infected with most or all strains of HIV. The strain-specific epitopes can be further selected to promote the stimulation of an immune response within an animal which is cross-reactive against other strains of HIV. Antigens from other HIV genes or combinations of genes, such as gag, pal, rev, vif, nef, prot, gag/pol, gag prot, etc., may also provide protection in particular cases.

In another aspect of the present invention, methods for inhibiting a function of a pathogenic agent necessary for disease, such as diseases caused by viral infections, cancers or immunological abnormalities, are disclosed. Where the pathogenic agent is a virus, the inhibited function may be selected from the group consisting of adsorption, replication, gene expression, assembly, and exit of the virus from infected cells. Where the pathogenic agent is a cancerous cell or cancer-promoting growth factor, the inhibited function may be selected from the group consisting of viability, cell replication, altered susceptibility to external signals, and lack of production of anti-oncogenes or production of mutated forms of anti-oncogenes. Such inhibition may be provided through recombinant retroviruses carrying a vector construct encoding "inhibitor palliatives," such as: (a) antisense RNA; (b) a mutant protein analogue to a pathogenic protein, which interferes with expression of the pathogenic state; (c) a protein that activates an otherwise inactive precursor; (d) defective interfering structural proteins; (e) peptide inhibitors of viral proteases or enzymes; (f) tumor suppressor genes; or (g) a RNA ribozyme capable of specifically cutting and degrading RNA molecules corresponding to the pathogenic state. Alternatively, such inhibition is attained by a recombinant retrovirus capable of site-specific integration into pathogenic genes, thereby disrupting them.

Such inhibition may also be accomplished through the expression of a palliative that is toxic for a diseased cell. Where a toxic palliative is to be produced by cells containing the recombinant viral genome, it is important that either the recombinant retrovirus infect only target cells or express the palliative only in target cells, or both. In either case, the final toxic agent is localized to cells in the pathogenic state. Where expression is targeted, the pathogenic agent controlling expression of the toxic palliative could be, for instance, a protein produced through transcription and translation of a pathogenic viral genome present in the cell.

It should be understood in the foregoing discussion, and throughout this application, that when reference is made to the viral construct "expressing" or "producing" any substance in a cell, or the like, this in fact refers to the action of the resulting provirus following reverse transcription of the viral RNA in the cell. In the context of a toxic palliative, the consequent killing effect may not necessarily require the permanent integration of the recombinant viral genome into the host genome, but simply a reasonably long-term expression of a toxic palliative gene, in whatever form desirable, over a reasonably long period of time (several days to one month). Thus, other nonintegrating viral vectors such as, but not limited to, adenoviral vectors may be used for this purpose. Examples of conditional toxic palliatives include recombinant retroviruses encoding (a) a toxic gene product under the control of a cell cycle-specific promoter, a tissue-specific promoter or both; (b) a gene product which is conditionally expressed and which in itself is not toxic but which processes within target cells a compound or drug from a nontoxic precursor form to an active toxic form; (c) a gene product which is not in itself toxic, but when processed by a protein, such as protease specific to a viral or other pathogen, is converted into a toxic form; (d) a conditionally expressed reporter gene product on the cell surface which identifies the pathogenic cells for attack, for example, by immunotoxins; (e) conditionally expressed gene products on the cell surface which lead to a toxic effect by interaction with extracellular factors; and (f) conditionally expressed ribozymes specific for RNA molecules essential for viability.

Within a related aspect, the present invention also provides methods for diminishing or eliminating an unwanted or deleterious immune response. Immune suppression, where appropriate, can be achieved by targeting expression of immune suppressive genes, such as the virally derived E3 gene of adenovirus.

Within another aspect of the present invention, methods are disclosed for inhibiting the interaction of viral particles with cells, cells with cells, or cells with factors. The methods generally comprise infecting susceptible cells with a recombinant, replication defective retrovirus which directs the expression of a blocking element in infected cells, the blocking element being capable of binding with a cell receptor (preferably the host cell receptor) either while the receptor is intracellular or on the cell surface, or alternatively, by binding with the agent. In either event, the interaction is blocked.

Regardless of the means by which the recombinant retrovirus exerts its immunogenic or inhibitory action as described above, it is preferred that the retroviral genome be "replication defective" (i.e., incapable of reproducing in cells infected with it). Thus, there will be only a single stage of infection in either an in vitro or in vivo application, thereby substantially reducing the possibility of insertional mutagenesis. Preferably, to assist in this end, the recombinant retrovirus lacks at least one of the gag, pol, or env genes. Further, the recombinant viral vector is preferably chimeric (that is, the gene which is to produce the desired result is from a different source than the remainder of the retrovirus). A chimeric construction further reduces the possibility of recombination events within cells infected with the recombinant retrovirus, which could produce a genome that can generate viral particles.

Within another aspect of the present invention, recombinant retroviruses which are useful in executing the above methods as well as delivering other therapeutic genes are disclosed. The present invention also provides a method for producing such recombinant retroviruses in which the retroviral genome is packaged in a capsid and envelope, preferably through the use of a packaging cell. The packaging calls are provided with viral protein-coding sequences, preferably in the form of two plasmids, which produce all proteins necessary for production of viable retroviral particles, an RNA viral construct which will carry the desired gene, along with a packaging signal which will direct packaging of the RNA into the retroviral particles.

The present invention additionally provides a number of techniques for producing recombinant retroviruses which can facilitate:

i) the production of higher titres from packaging cells;

ii) the production of higher titres of helper free recombinant retrovirus from packaging cell lines that are non-murine (to avoid production of recombinant or endogenously activated retroviruses, and to avoid packaging of defective murine retroviral sequences) and which will infect human cells;

iii) the production of helper free recombinant retroviruses with higher titres using alternative non-hybrid envelopes such as xenotropic or polytropic envelope proteins (to allow infection of cells poorly infectable with amphotropic recombinant retroviruses or to allow specificity of cell type infection).

iv) packaging of vector constructs by means not involving the use of packaging cells;

v) the production of recombinant retroviruses which can be targeted for preselected cell lines;

vi) the construction of retroviral vectors with tissue-specific (e.g., tumor) promoters; and vii) the integration of the proviral construct into a preselected site or sites in a cell's genome.

One technique for producing higher titres from packaging cells takes advantage of the discovery that of the many factors which can limit titre from a packaging cell, one of the most limiting is the level of expression of the packaging proteins, namely, the gag, pol, and env proteins, as well as the level of expression of the retroviral vector RNA from the proviral vector. This technique allows the selection of packaging cells which have higher levels of expression (i.e., produce higher concentrations) of the foregoing packaging proteins and vector construct RNA. More specifically, this technique allows selection of packaging cells which produce high levels of what is referred to herein as a "primary agent," which is either a packaging protein (e.g., gag, pol, or env proteins) or a gene of interest to be carried into the genome of target cells (typically as a vector construct). This is accomplished by providing in packaging cells a genome carrying a gene (the "primary gene") which expresses the primary agent in the packaging cells, along with a selectable gene, preferably downstream from the primary gene. The selectable gene expresses a selectable protein in the packaging cells, preferably one which conveys resistance to an otherwise cytotoxic drug. The cells are then exposed to a selecting agent, preferably the cytotoxic drug, which enables identification of those cells which express the selectable protein at a critical level (i.e., in the case of a cytotoxic drug, by killing those cells which do not produce a level of resistance protein required for survival).

Preferably, in the technique briefly described above, the expression of both the selectable and primary genes is controlled by the same promoter. In this regard, it may be preferable to utilize a retroviral 5' LTR. In order to maximize titre of a recombinant retrovirus from packaging cells, this technique is first used to select packaging cells expressing high levels of all the required packaging proteins, and then is used to select which of these cells, following transfection with the desired proviral construct, produce the highest titres of the recombinant retrovirus.

Techniques are also provided to select cells that produce higher titres of helper free recombinant retroviruses in non-murine cells. These cell lines produce recombinant retroviruses capable of efficiently infecting human cells. These techniques involve screening potential parent cells for their ability to produce recombinant retroviruses in the presence of a replicating virus. Subsequently, uninfected cultures of candidate cell lines chosen by the above procedure are infected with a vector expressing MLV gag/pol, and clones which synthesize high levels of gag/pol are identified. A clone of this type is then reinfected with a vector expressing env, and clones expressing high level of env (and gag/pol) are identified. Within the context of the present invention, "high levels" means discernibly greater than that seen in the standard mouse packaging line, PA317 on a Western blot analysis. Many non-mouse cell lines such as human or dog have never been known to spontaneously generate competent retrovirus, do not carry possible recombination partners for recombinant retroviral packaging or gene sequences; and do not carry genes which make RNA which may be packaged by the MLV system. Techniques are provided to generate cell lines which produce high titres of recombinant retroviruses using alternative envelopes such as xenotropic or polytropic by techniques similar to those described above. Such retroviruses may be used in infecting amphotropic resistant cells (xenotropic envelope) or infecting only a subset of cells (polytropic).

Techniques are also provided for packaging of vector constructs by means not involving the use of packaging cells. These techniques make use of other vector systems based on viruses such as other unrelated retroviruses, baculovirus, adenovirus, or vaccinia virus, preferably adenovirus. These viruses are known to express relatively high levels of proteins from exogenous genes provided therein. For such DNA virus vectors, recombinant DNA viruses can be produced by in vivo recombination in tissue culture between viral DNA and plasmids carrying retroviral or retroviral vector genes. The resultant DNA viral vectors carrying either sequences coding for retroviral proteins or for retroviral vector RNA are purified into high titre stocks. Alternatively, the constructs can be constructed in vitro and subsequently transfected into cells which provide in trans viral functions missing from the DNA vectors. Regardless of the method of production, high titre ($10^7$ to $10^{11}$ units/ml) stocks can be prepared that will, upon infection of susceptible cells, cause high level expression of retroviral proteins (such as gag, pol, and env) or RNA retroviral vector genomes, or both. Infection of cells in culture with these stocks, singly or in combination, will lead to high-level production of retroviral vectors, if the stocks carry the viral protein and viral vector genes. This technique, when used with adenovirus or other mammalian vectors, allows the use of primary cells (e.g., from tissue explants or cells such as WI38 used in production of vaccines) to produce recombinant retroviral vectors.

In an alternative to the foregoing technique, recombinant retroviruses are produced by first generating the gag/pol and env proteins from a cell line infected with the appropriate recombinant DNA virus in a manner similar to the preceding techniques, except that the cell line is not infected with a DNA virus carrying the vector construct. Subsequently, the proteins are purified and contacted with the desired viral vector RNA made in vitro, transfer RNA (tRNA), liposomes, and a cell extract to process the env protein into the liposomes, such that recombinant retroviruses carrying the viral vector RNA are produced. Within this technique, it may be necessary to process the env protein into the liposomes prior to contacting them with the remainder of the foregoing mixture. The gag/pol and env proteins may also be made after plasmid mediated transfection in eukaryotic cells, in yeast, or in bacteria.

A technique suitable for producing recombinant retroviruses which can be targeted for preselected cell lines utilizes recombinant retroviruses having one or more of the following: an env gene comprised of a cytoplasmic segment of a first retroviral phenotype, and an extracellular binding segment exogenous to the first retroviral phenotype (the binding segment being from a second viral phenotype or from another protein with desired binding properties which is selected to be expressed as a peptide which will bind to the desired target); another viral envelope protein; another ligand molecule in place of the normal envelope protein; or another ligand molecule along with an envelope protein that does not lead to infection of the target cell type. Preferably, in the technique briefly described above, an env gene comprised of a cytoplasmic segment of a retroviral phenotype is combined with an exogenous gene encoding a protein having a receptor-binding domain to improve the ability of the recombinant retrovirus to bind specifically to a targeted cell type, e.g., a tumor cell. In this regard, it may be preferable to utilize a receptor-binding domain which binds to receptors expressed at high levels on the surface of the target cell (e.g., growth factor receptors in tumor cells) or alternatively, a receptor-binding domain binding to receptors expressed at a relatively higher level in one tissue cell type (e.g., epithelial cells, ductal epithelial cells, etc., in breast cancer). Within this technique, it may be possible to improve and genetically alter recombinant retroviruses with specificity for a given tumor by repeated passage of a replicating recombinant retrovirus in tumor cells; or by linking the vector construct to a drug resistance gene and selecting for drug resistance.

The technique for the construction of retroviral vectors with tissue (e.g., tumor)-specific promoters utilizes recombinant retroviruses having regulatory control elements operative in a tissue of interest (e.g., beta globin gene promoter in bone marrow leading to expression in reticulocytes, immunoglobulin promoter in B cells, etc). The tissue-specific regulatory control element is able to direct expression of a gene encoding a lethal agent in target cells in which the control elements are operable. The operability of the regulatory control element in different tissues may not need to be absolutely-specific for a particular tissue to be used in this technique, since quantitative differences in operability may be sufficient to confer a substantial level of tissue specificity to the lethality of the agent under the control of the element.

Techniques for integrating a retroviral genome at a specific site in the DNA of a target cell involve the use of homologous recombination, or alternatively, the use of a modified integrase enzyme which will recognize a specific site on the target cell genome. Such site-specific insertion allows genes to be inserted at sites on the target cells' DNA, which will minimize the chances of insertional mutagenesis, minimize interference from other sequences on the DNA, and allow insertion of sequences at specific target sites so as to reduce or eliminate the expression of an undesirable gene (such as a viral gene) in the DNA of the target cell.

It will be appreciated that any of the above-described techniques may be used independently of the others in particular situations, or can be used in conjunction with one or more of the remainder of the techniques.

These and other aspects of the present invention will become evident upon reference to the following detailed description and attached drawings.

BRIEF DESCRIPTION OF THE DRAWINGS

FIG. 1A depicts three different families of vectors used to produce HIV env and which may or may not have the selectable SV-Neo cassette inserted.

FIG. 1B depicts vectors KT1, KT2 and KT3 with the RNA transcripts expected and seen from cells infected with these vectors. KT1 encodes HIV env IIIB and gives at least 10 fold higher titres ($10^6$ cfu/ml) than the vectors in FIG. 1A. KT2 and KT3 express full-length HIV gag/pol and a truncated gag/pol gene respectively.

FIG. 1C depicts the plasmid expression vector 62/3 and the retroviral expression vectors 53-7 and 51-1. All of these lead to expression of the MCMV pp89 IE gene.

FIG. 2 illustrates the HIV env expression levels seen in polyacrylamide gel electrophoresis of HIV env-specific radioimmune precipitations of extracts of human Sup T1 cells transfected with the vectors shown. The markers are in kilodaltons, gp 160 and gp 120 mark the appropriate proteins, and 517+tat is the positive control (HIV LTR driving env in the presence of tat).

FIG. 3 depicts the protocol for testing T-cell killing induced in mice injected with syngeneic tumor cells expressing HIV env (the vector is pAF/$Env^r$/$SV_2$neo).

FIG. 4A graphically depicts the results of the experimental protocol in FIG. 3. The specific killing is seen in the top graph with BC10MEenv-29 being killed in contrast to B/C10ME control cells lacking in HIVenv-expression.

FIG. 4B illustrates the specificity of the CTL for HIV envelope antigens.

FIG. 4C demonstrates the phenotype of the effector cell population generated in the experimental protocol in FIG. 3. The effector cell population is that of an $L3T4^-$lyt2+($CD4^-$ $CD8^+$) T lymphocyte.

FIG. 4D illustrates the MHC restriction requirements for the Balb/c anti-BCenv CTL response.

FIG. 4E demonstrates that CTL can be induced in vivo by irradiated nonproliferating stimulator cells.

FIG. 4F illustrates the dose-response relationship of immunizing Balb/c mice with BCenv stimulator cells.

FIG. 4G demonstrates the generation of CTL responses by different H-$2^d$ mouse strains as well as F1 hybrid mice against BCenv target cells.

FIG. 4H demonstrates that CTL induced in mice to envelope of the HIV III B strain of virus kill (B/C 10ME env) HIVenv-expressing target cells as well as non-target B/C 10 ME cells (BC) if they are coated with peptide homologous to the HIV III B strain of virus (RP 135). The results also demonstrate that these CTL cross-react and kill some cells coated with peptide homologous to the envelope of the MN strain of HIV (RP 142).

FIG. 4I demonstrates induction of HIV envelope specific murine CTL (Env-specific-CTL) following intraperitoneal injection of $10^7$ BC cells transfected with plasmid DNA having a recombinant vector construct in which the cytomegalovirus (CMV) promoter directs transient expression of the HIV IIIb envelope as evidenced by specific CTL killing of BCpCMVenv IIIb target cells transiently-expressing HIVenv (BCpCMVenvIIIb target) and cloned stable—HIVenv-expressing BC29 target cells (BC29 target) but not non-infected BC cells (BC10ME target).

FIG. 4J demonstrates that murine BC target cells infected two days before use by transfection with CMVH2-Dd or RSV-Dd which encode H2-Dd under control of the Cmv or RSV-LTR promoter, respectively, serve as target cells for killing by C57BL16 muring CTL immunized with Balb/C cells (H2-Dd). These CTL specifically kill target cells expressing H2-Dd but not control 3T3 cells.

FIG. 4K graphically depicts the results of an experimental protocol similar to that in FIG. 3, wherein mice were injected with cells expressing gag/pol (BC-1-16H) or gag/prot (BC-1) instead of cells expressing HIVenv. CTL from gag/pol or gag/prot immunized mice killed their respective target cell, either BC-1 or BC-1-16H target cells, respectively, but not B/C 10 ME cells.

FIG. 4L demonstrates that CTL induced by gag/pol stimulator cells (BC-1-15H; abbreviated 1-15H) killed both gag/pol (1-15H) and gag/prot (BC-1) target cells.

FIG. 4M demonstrates that CTL induced by gag/prot stimulator cells (BC-1) killed both gag/prot (BC-1) and gag/pol (1-15H) target cells.

FIG. 4N demonstrates that two (2×) direct injections of HIVenv encoding retrovirus by the intraperitoneal (I.P.) or intramuscular (I.M.) routes stimulated the development of CTL capable of specifically killing BC10MEenv-29 cells but not B/C 10 ME control cells (BC)

FIG. 4O demonstrates in vitro immunization of human donor #99PBL using autologous EBV-transformed stimulator calls from donor #99 (99-EBV) that were infected in vitro with recombinant retroviral vector encoding HIVenv (99-EBV-HIVenv) to effect induction of CTL which kill 99-EBV-HIVenv target cells but not negative control autologous cells, i.e., 99-PHA stimulated PBL (99 PHA blasts).

Donor #99 expressed natural immunity to EBV, as evidenced by a lower level of killing of positive control 99-EBV target cells.

FIG. 4P demonstrates that human HT1080 cells infected with both murine MHC H2-Dd and HIVenv antigen (HT1080+Dd+env) simultaneously express both gene products in a functionally-active form as evidenced by the lysis of these cells by HIVenv-immune murine CTL. These HIVenv-immune CTL did not induce significant lysis of either control HT1080 (HT1080) cells or BC cells expressing H2-Dd (BC-Dd).

FIG. 4Q demonstrates in panel A the lysis of BC cells expressing HIV envelope proteins (BCenvIIIb) and BC cells coated with RP135 "V3loop" ("loop") synthetic peptide by HIVenv-immune CTL; in panel B, the lysis of BCenvΔV3 cells lacking the gp120 hypervariable envelope loop (i.e., "loopless") by CTL immunized with "loopless" BCenvΔV3 cells. The CTL immunized with "loopless" BCenvΔV3 were specific, i.e., they did not lyse BC cells lacking in HIVenv (BC) and they did not lyse cells coated with the "loop" RP135 peptide (BC-RP135).

FIG. 4R demonstrates: in panel A, the specific lysis of BC cells expressing a truncated envelope protein from a recombinant HIVenv gene (BCpcmv Chunk 1 target; referred to as "Chunk 1" (see Example 1F2)), and also cloned infected BC cells expressing HIVenvIIIb (BCenvIIIb 29 target) by BCenvIIIb 29-immune murine CTL; and in panel B, the induction of immune CTL in mice immunized with BCpCMVChunk 1 cells which specifically kill BCpCMVChunk 1 target cells and BCenvIIIb-14H target cells but not non-infected BC cells (BC10ME target).

Figure 12:
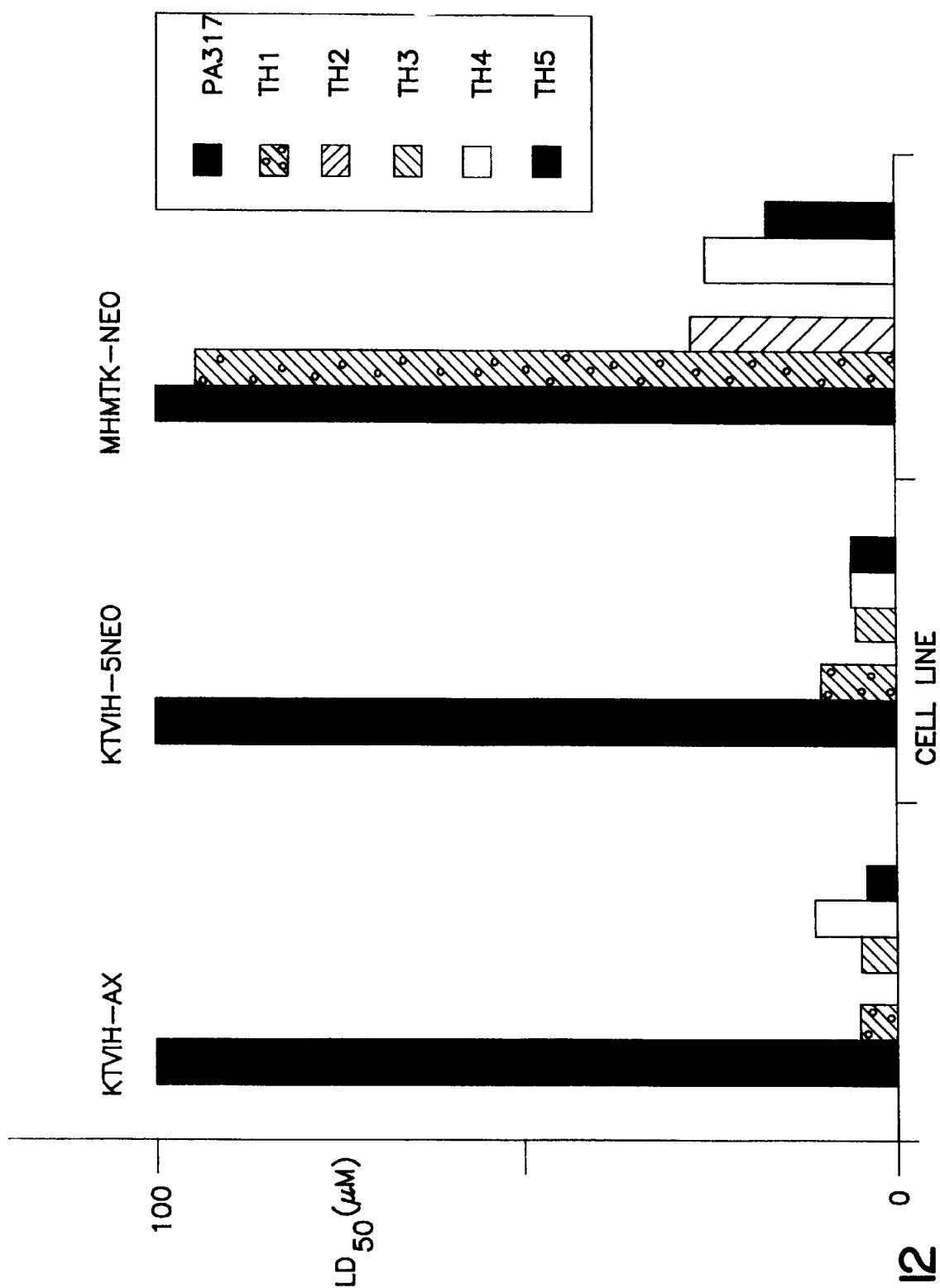

FIG. 12 graphically depicts the preferential killing of PA317 cells infected with tathis vector (5 clones, TH1–5) compared to control PA317, upon infection with the three conditional lethal vectors shown and treatment with acyclovir (ACV).

Figure 13:
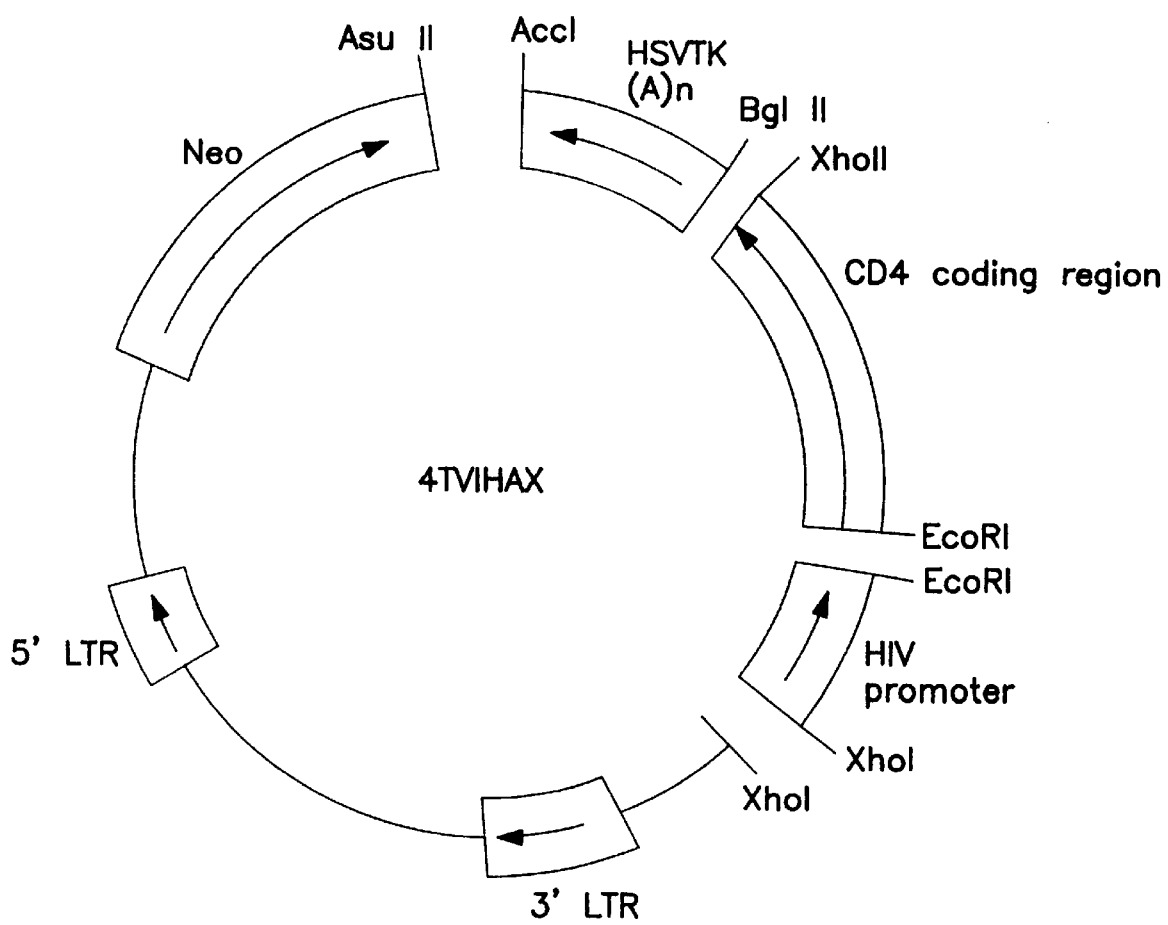

FIG. 13 illustrates the constuction of the lasmid carrying the vector 4TVIHAX.

Figure 14:
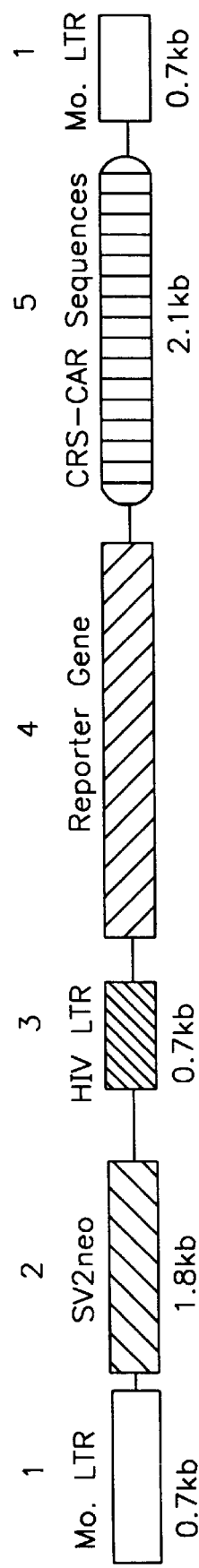

FIG. 14 depicts the construction of a viral vector carrying HIV inducible marker/reporter genes such as alkaline phosphatase (AP).

Figure 15:
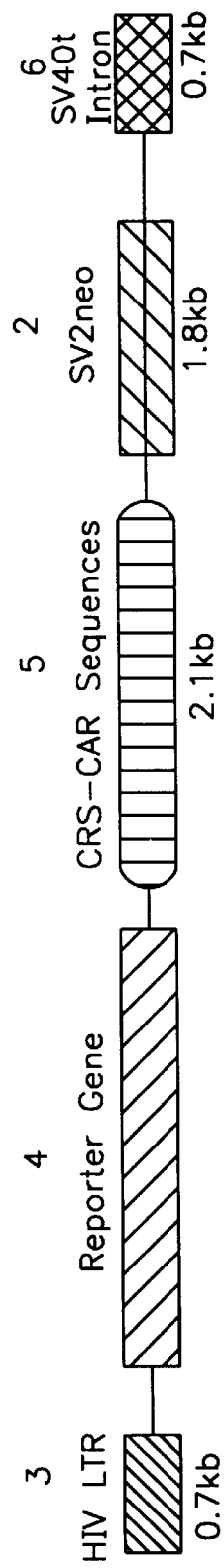

FIG. 15 depicts the structure of an HIV inducible marker/reporter gene carried on a plasmid which can be transfected into cells.

Figure 16:
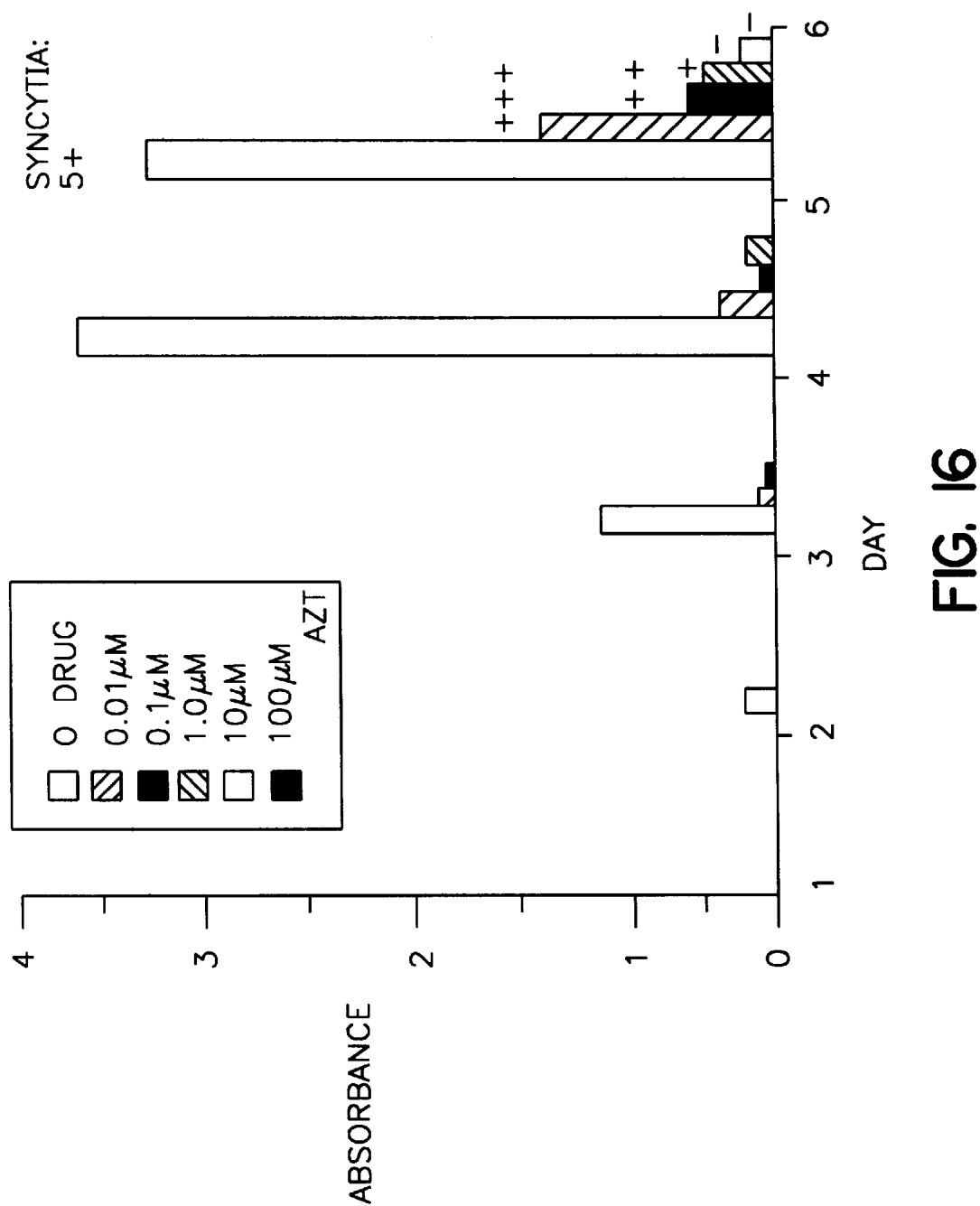

FIG. 16 graphically depicts a time course of HIV infection of Sup T1 cells carrying the AP marker in FIG. 15 with HIV at various concentrations of AZT. The level of HIV infection was measured by taking small aliquots of supernatant.

Figure 17:
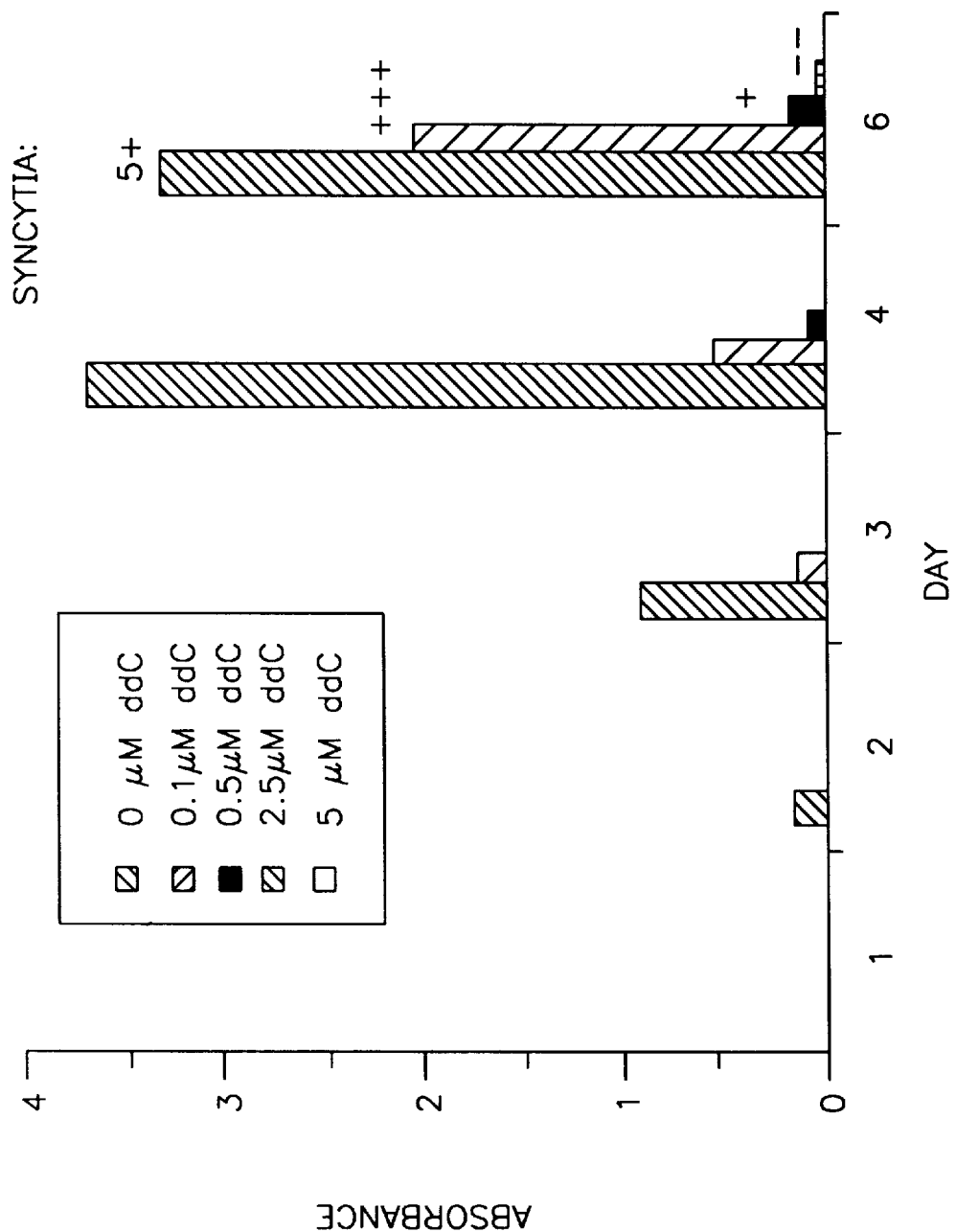

FIG. 17 graphically depicts the results of the same experiment as in FIG. 16, but with ddC as the HIV inhibitor.

Figure 18:
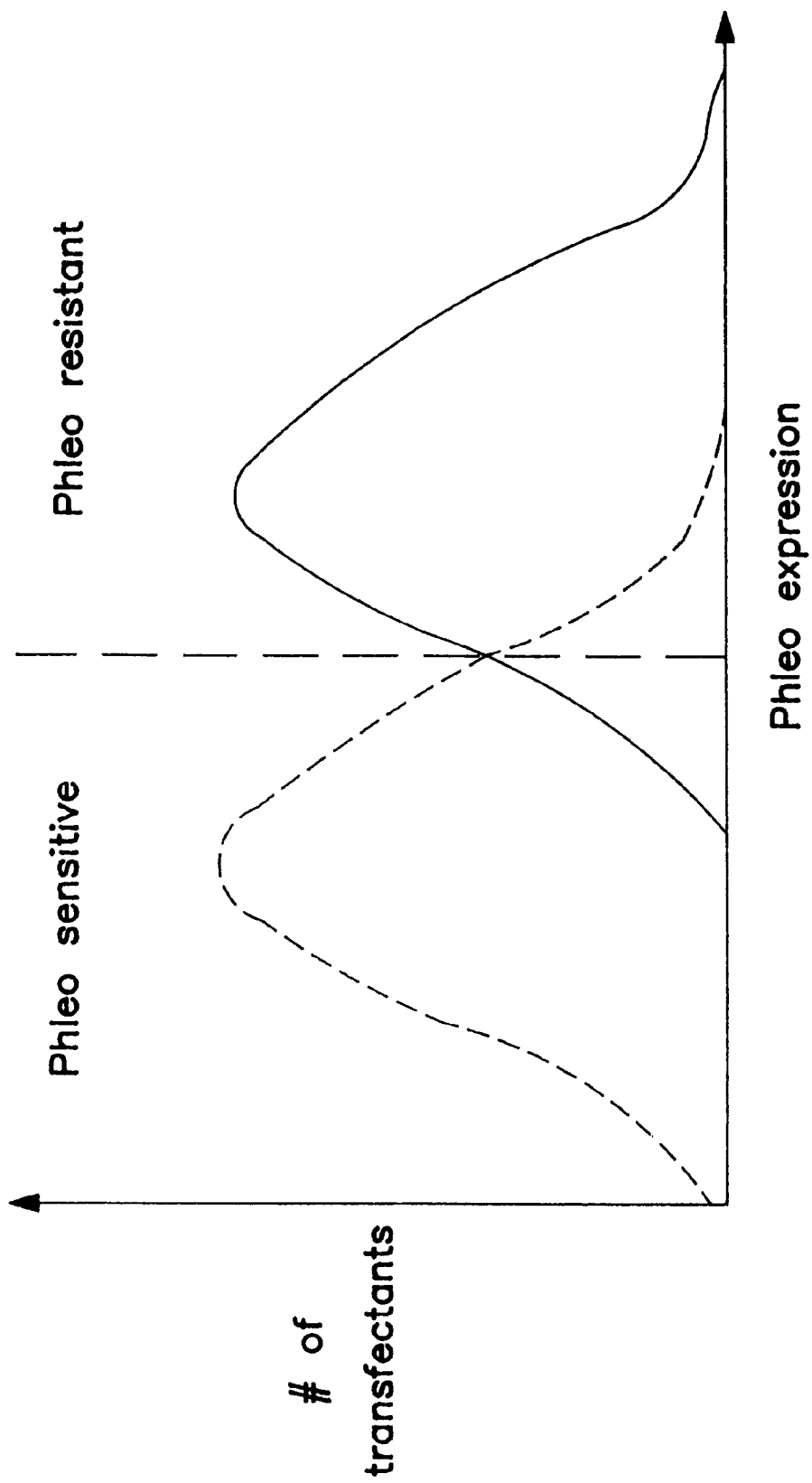

FIG. 18 diagrammatically illustrates the number of cells surviving after phleomycin selection upon transfection of cells with a plasmid which expresses the phlemoycin resistance gene (PRG) directly from a promoter (right, complete line), and with another which expresses PRG with a coding sequence interposed between it and the promoter (left, dotted line).

Figure 19A:
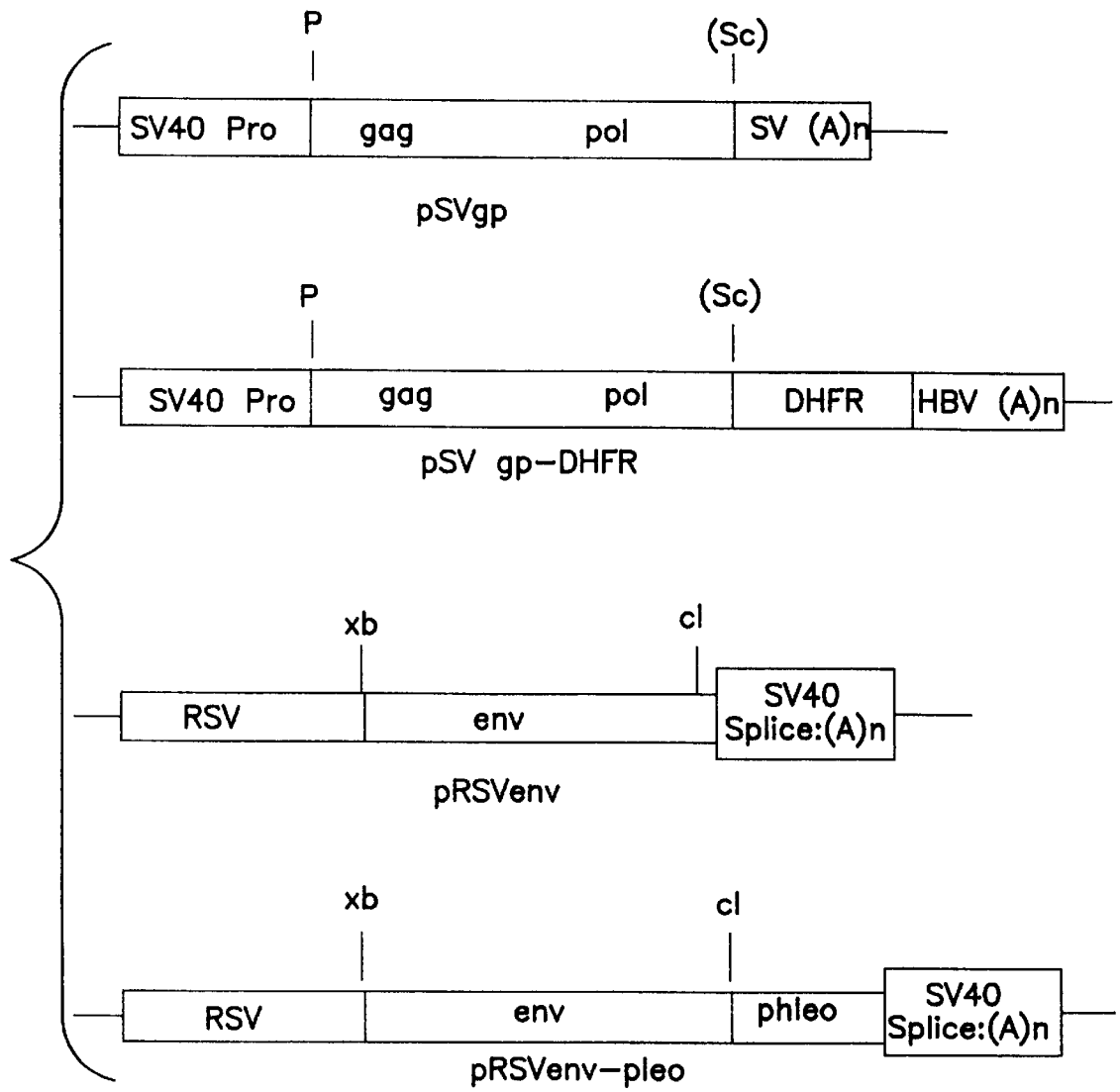

FIG. 19A depicts four plasmids designed to express retroviral proteins in mammalian cells. pSVgp and pRSVenv are cotransfected with a selectable marker, while pSVgp-DHFR and pRSVenv-phleo are the equivalent plasmids with the selectable marker placed downstream of the viral protein-coding regions.

Figure 19B:
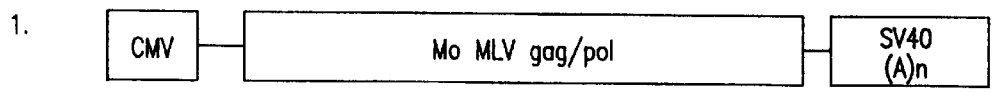
Figure 19B:
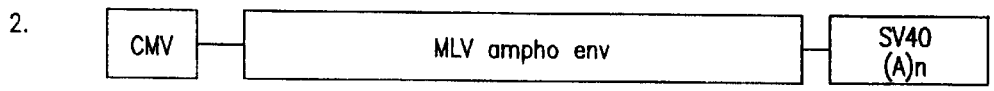
Figure 19B:
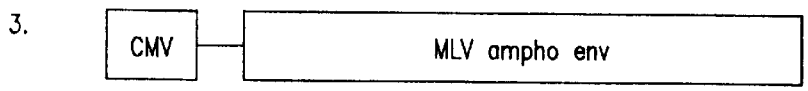
Figure 19B:
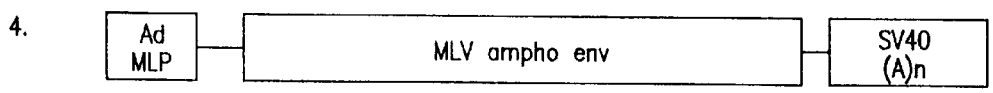
Figure 19B:
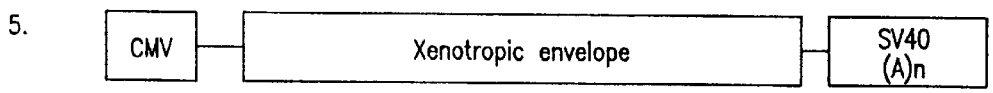
Figure 19B:
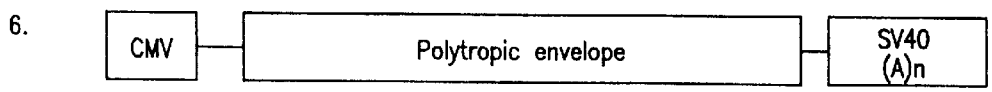
Figure 19B:
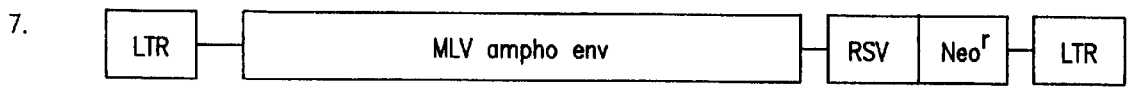

FIG. 19B depicts vectors which lead to expression of: 1. MLV core proteins (pSCV10); 2-4 MLV amphotropic env (pCMVenv AmDra, pCMVenv AnNhe, pMLPenv AmSph); 5. MLV xenotropic env (pCMV xeno). 6. MLV MCFenv (pCMV MCF); 7. MLV amphotropic env as a retroviral vector (pLARNL).

Figure 19C:
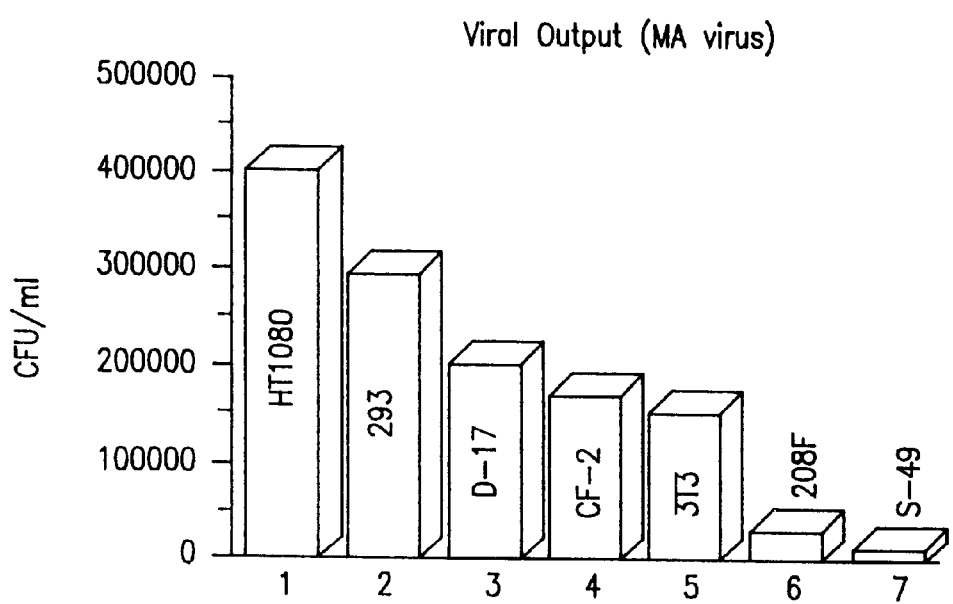

FIG. 19C depicts the results of the screening procedure for assessing the intrinsic ability of cell lines to make retroviral vectors in the presence of helper virus (Example 9B).

Figure 19D:
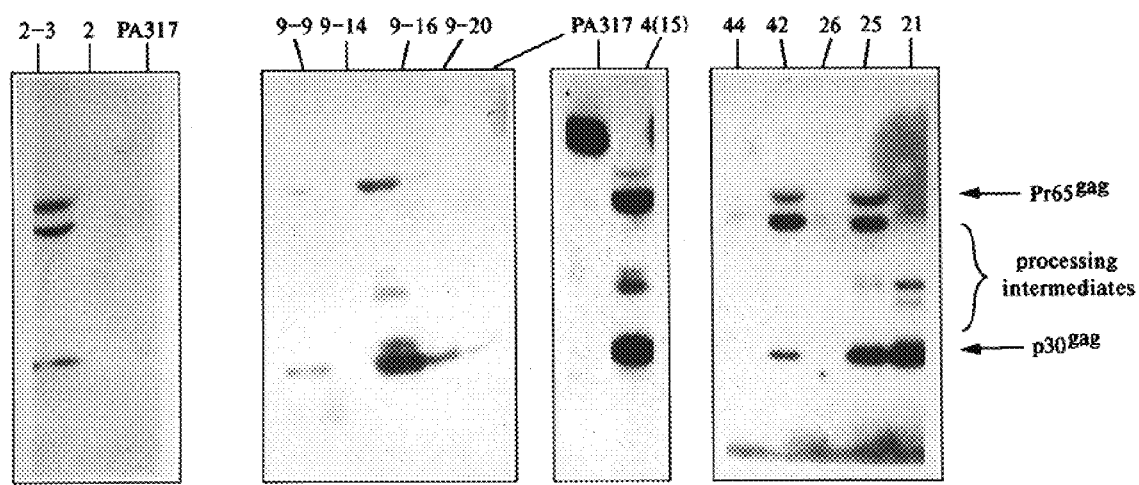

FIG. 19D depicts the results of selecting clones of cells into which pSCV10 had been introduced and examining these clones for gag/pol production as compared to PA317 by Western blots.

Figure 19E:
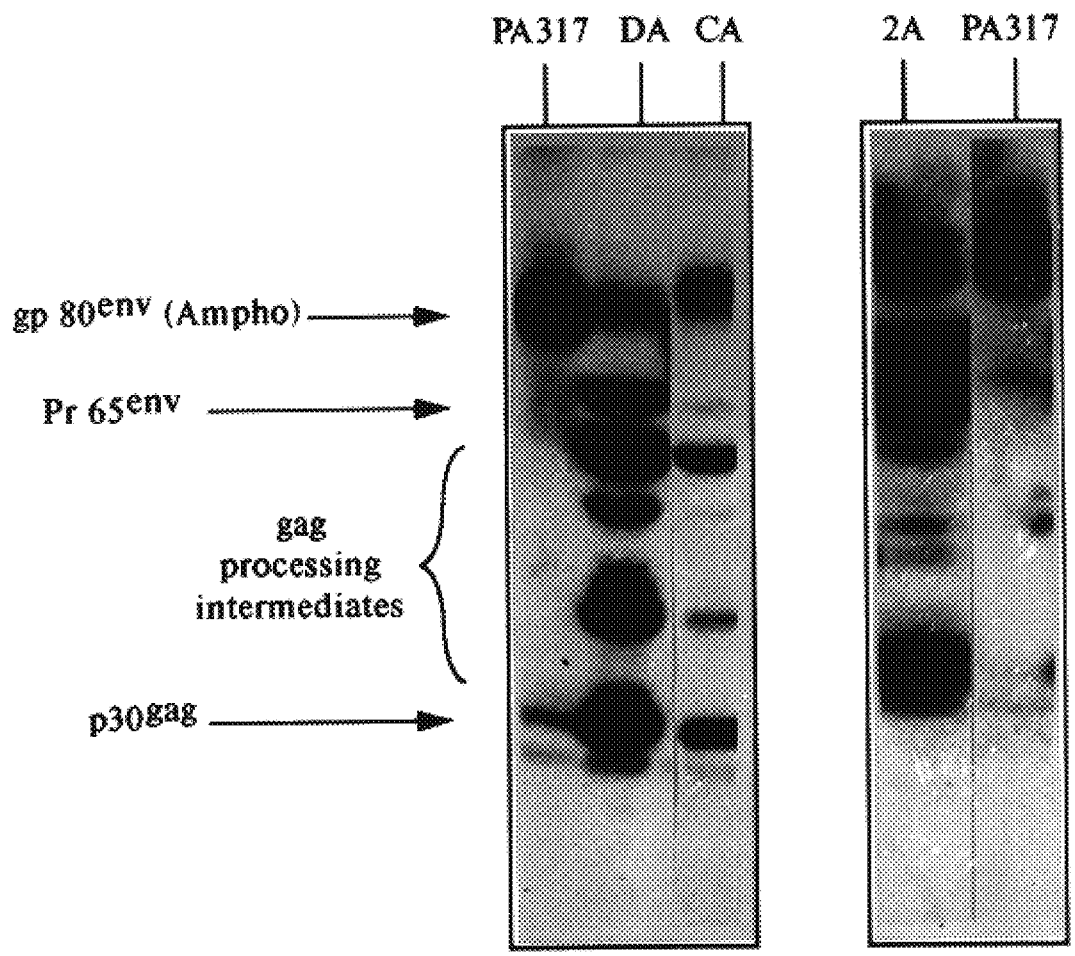

FIG. 19E depicts the results of Western blot experiments to compare levels of amphotropic env in cell lysates from DA, CA, 2A and PA317.

FIG. 19F depicts the results of Western blot experiments to compare levels of xenotropic env in cell lysates from transient transfections of CF gag/pol and permanently expressing lines XF7, X6, X10 and PA317 (ampho env).

Figure 19G:
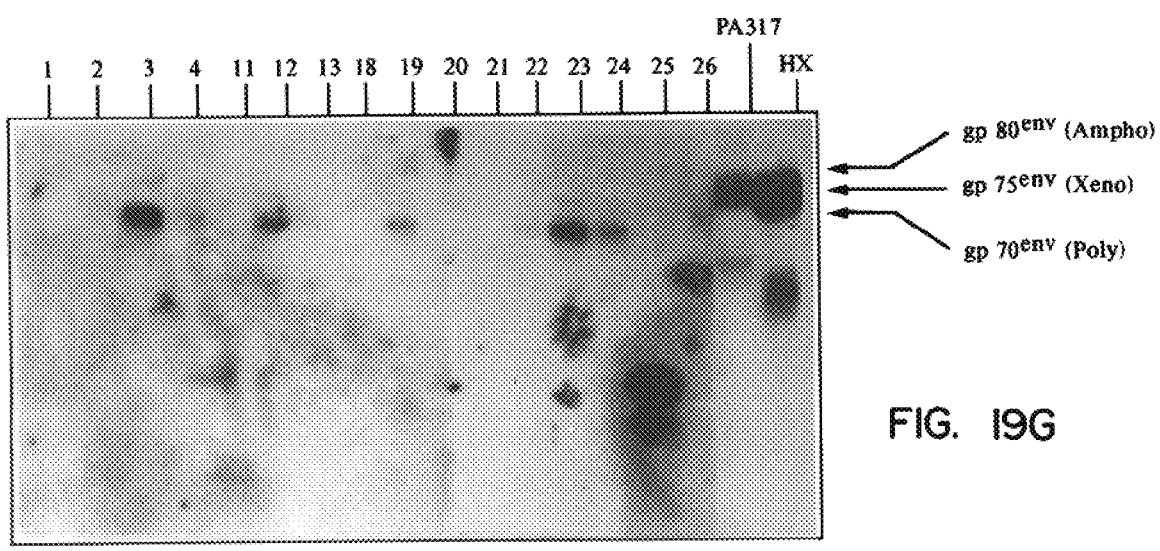

FIG. 19G depicts the results of Western blot experiments to compare levels of MCF (polytropic) env in HT1080 derived clones, PA317 (amphotropic env) and HX (xenotropic env).

Figure 20:
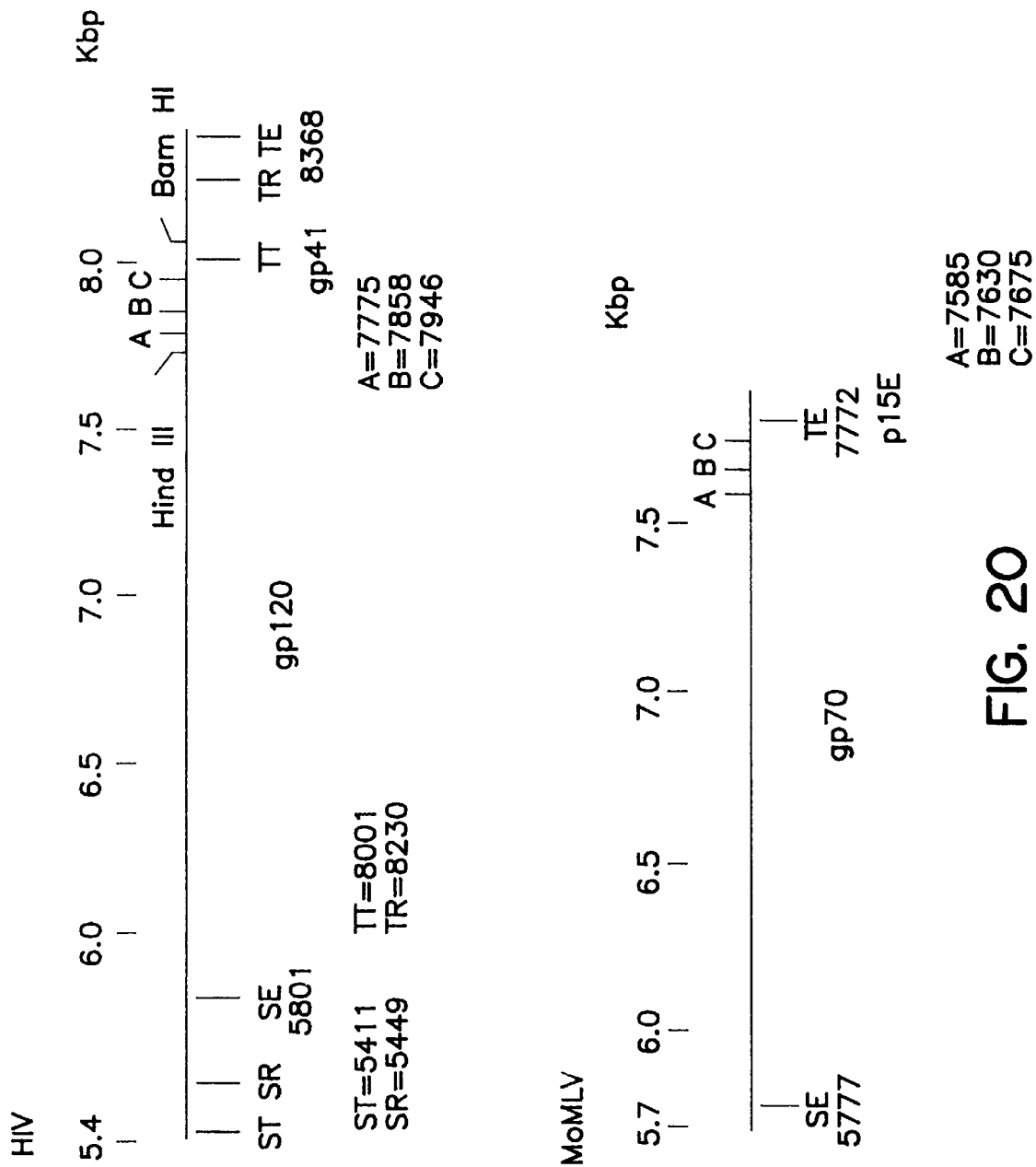

FIG. 20 depicts three sites of fusion of HIV env and MOMLV env after site-directed mutagenesis. The joint at the extracellular margin of the transmembrane region is designated as A, while B and C indicate locations of joints at the middle of the transmembrane region and cytoplasmic margin, respectively. The numbering is according to nucleotide numbers (*RNA Tumor Viruses*, Vol. II, Cold Spring Harbor, 1985). ST, SR, SE are the starts of tat, rev and env while TT, TR, and TE are the corresponding termination sites.

Figure 21:
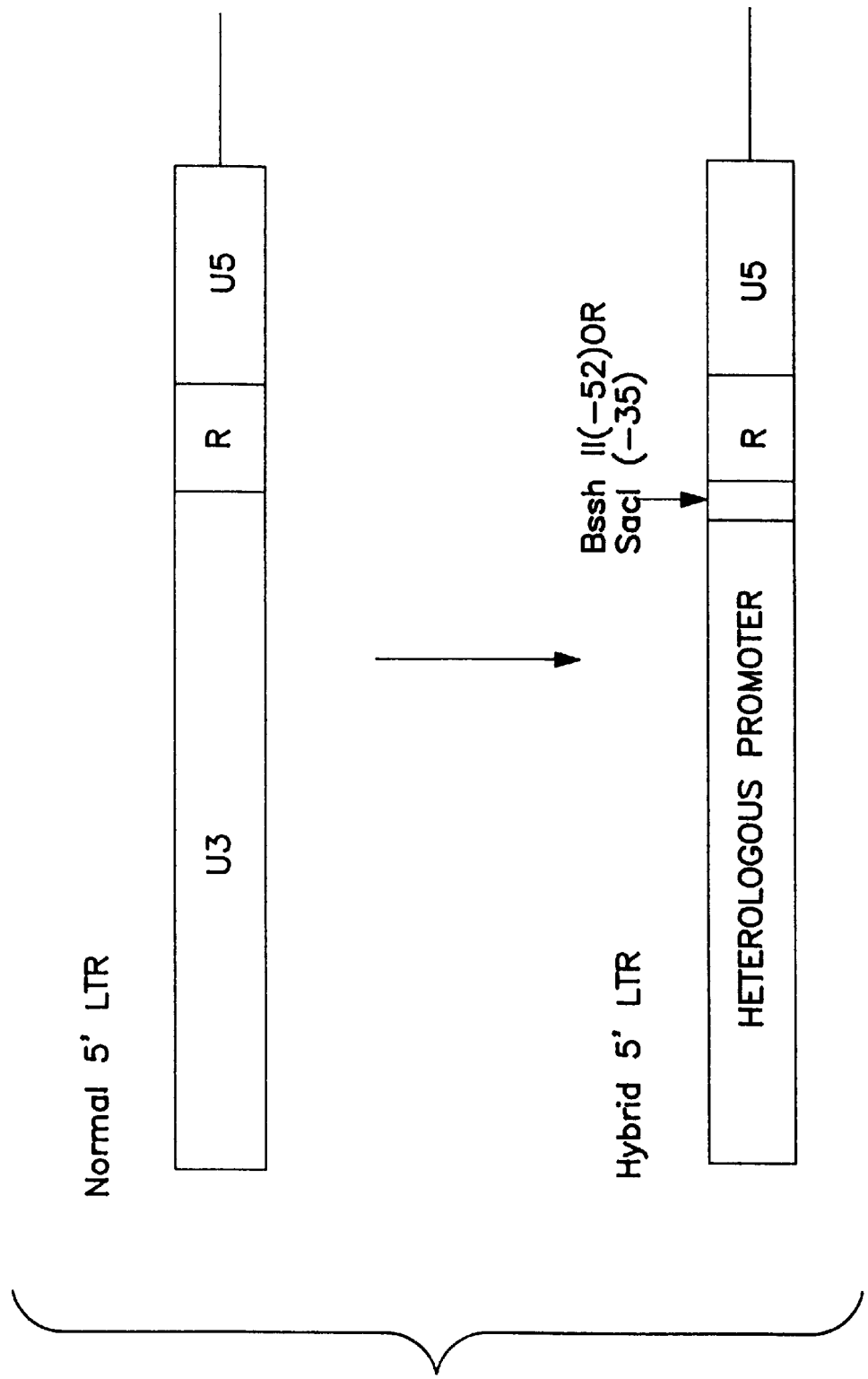

FIG. 21 depicts the substitution of U3 in a 5' LTR by a heterologous promoter/enhancer which can be fused to either the Sac I, Bssh II or other site in the region.

Figure 22:
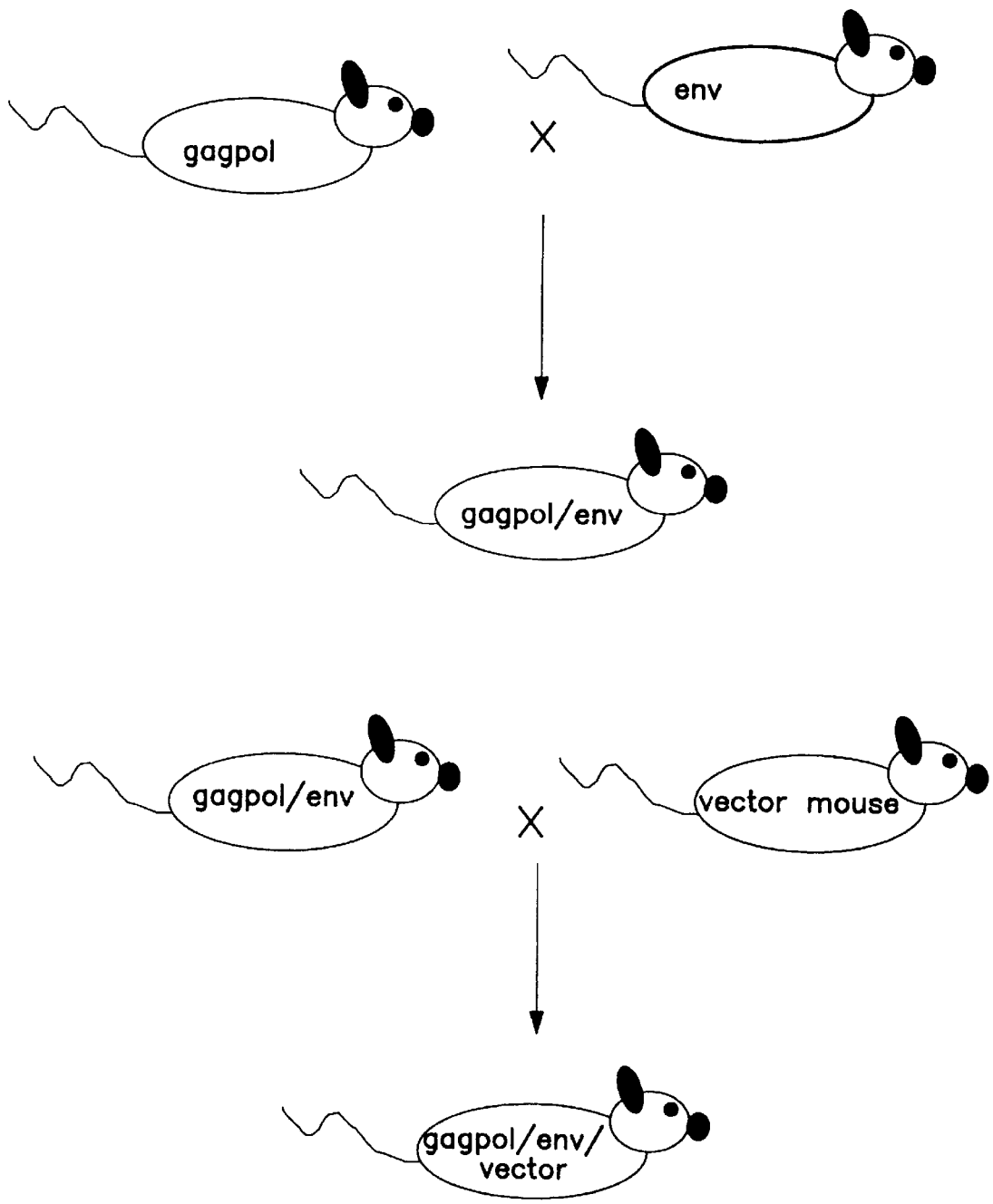

FIG. 22 illustrates a representative method for crossing transgenic mice expressing viral protein or vector RNA.

DETAILED DESCRIPTION OF THE INVENTION

I. Immunostimulation

The ability to recognize and defend against foreign pathogens is central to the function of the immune system. This system, through immune recognition, must be capable of distinguishing "self" from "nonself" (foreign), which is essential to ensure that defensive mechanisms are directed toward invading entities rather than against host tissues. The fundamental features of the immune system are the presence of highly polymorphic cell surface recognition structures (receptors) and effector mechanisms (antibodies and cytolytic cells) for the destruction of invading pathogens.

Cytolytic T lymphocytes (CTL) are normally induced by the display of processed pathogen-specific peptides in conjunction with the MHC class I or class II cell surface proteins. Also stimulated by this type of antigen presentation are the generation and production antibodies, helper cells and memory cells. Within one embodiment of the present invention, presentation of immunogenic viral determinants in the context of appropriate MHC molecules efficiently induces optimal CTL responses without exposing the patient to the pathogen. This vector approach to immunostimulation provides a more effective means of inducing potent class I-restricted protective and therapeutic CTL responses, because the type of immunity induced by the vector more closely resembles that induced by exposure to natural infection. Based on current knowledge of several viral systems, it is unlikely that exogenously supplied, nonreplicating viral antigens, such as peptides and purified recombinant proteins, will provide sufficient stimulus to induce optimal class I-restricted CTL responses. Alternatively, vector-delivered expression of selected viral proteins or other antigens corresponding to a pathogenic condition, such as cancer, within target cells as described within the present invention provides such a stimulus.

By way of example, in the case of HIV-1 infections, patients develop antibodies specific for a variety of viral envelope-region determinants, some of which are capable of in vitro virus neutralization. Nevertheless, disease progression continues and the patients eventually succumb to the disease. Low-level CTL responses against infected patients' cells (Plata et al., *Nature* 328:348–351, 1987) and against target cells infected with recombinant vaccinia vectors expressing HIV gag, pol, or env (Walker et al., *Nature* 328:345–348, 1987; Walker et al., *Science* 240:64–66, 1988) have been detected in some HIV-1 seropositive patients. In addition, it has recently been shown that murine as well as human CTL can be induced by autologous stimulator cells expressing HIV gp 120 via transfection (Langlade-Demoyan et al., *J. Immunol.* 141:1949, 1988). Improved CTL induction could be therapeutically advantageous to infected patients and provide effective preventive therapy to individuals under noninfectious conditions. HIV infection itself may not be producing an adequate CTL response because other elements associated with HIV infection may prevent proper immune stimulation. In addition, it may be that stimulation of T-cells by infected cells is an interaction that leads to infection of the stimulated T-cells.

HIV is only one example. This approach should be effective against many virally linked diseases or cancers where a characteristic antigen (which does not need to be a membrane protein) is expressed, such as in HPV and cervical carcinoma, HTLV-I-induced leukemias, prostate-specific antigen (PSA) and prostate cancer, mutated p53 and colon carcinoma, GD2 antigen and melanoma. Example 1 describes procedures for constructing plasmids capable of generating retroviral vectors in packaging cells, which then lead to expression of HIV viral antigens.

EXAMPLE 1

Vectors Exmressina HIV Antigens

A. Env Expression Vector (See FIG. 1):

A 2.7 kb Kpn-Xho I DNA fragment was isolated from the HIV proviral clone BH10-R3 (for sequence, see Ratner et al., *Nature* 313:277, 1985) and a ≈400 bp Sal-Kpn I DNA fragment from IIIexE7deltaenv (a Bal31 deletion to nt. 5496) was ligated into the Sal I site in the plasmid $SK^+$. From this clone, a 3.1 kb env DNA fragment (Xho I-Cla I) which also encodes rev, essential for env expression, was purified and ligated into a retroviral vector called pAFVXM (see Kriegler et al., *Cell* 38:483, 1984). This vector was modified in that the Bgl II site was changed by linker insertion to a Xho I site to facilitate cloning of the HIV env coding DNA fragment.

A dominant selectable marker gene comprised of a SV40 early promoter driving expression of neomycin phosphotransferase gene was inserted into the vector at the Cla I site to facilitate isolation of infected and transfected cell lines. This vector is called pAF/$Env^r$/$SV_2$neo (see FIG. 1).

The Xho I site upstream from the ENV gene in the vector provides a convenient site to insert additional promoters into the vector construct as the RSV promoter, SV40 early or late promoter, the CMV immediate early (IE) promoter, human beta-actin promoter, and Moloney murine MLV SL3-3 promoter.

One such promoter, the CMV Immediate Early gene promoter (see FIG. 1), a 673 bp DNA fragment Hinc II to Eag I, results in a tenfold increase in ENV expression in a human T-cell line called Sup T1 when compared to the parental construct pAF/$Env^r$/$SV_2$neo (see FIG. 2).

To improve titres of the vector one can use a recombinant retrovirus based on N2 (Armentano et al., *J. Virol.* 61:1647–1650, 1987; Eglitas et al., *Science* 230:1395–1398, 1985). This vector contains both the packaging sequences from N2 as well as the bacterial neomycin phosphotransferase gene. The above HIV env construct was inserted into the unique Xho I site in N2 as follows.

The MoMuLV 5' LTR fragment, including GAG sequences, from N2 (Eco RI-Eco RI) was ligated into plasmid $SK^+$ resulting in a construct called N2R5. The N2R5 construct was mutagenized by site-directed invitro mutagenesis to change the GAG ATG to ATT. This mutagenized site was flanked by Pst I sites 200 bp apart. The 200 bp mutagenized fragment was purified and inserted into the same Pst I sites (to replace the non-mutagenized 200 bp fragment) of N2 MoMuLV 5' LTR in plasmid pUC 31. The resulting construct was called pUC 31/N2RS $g^M$. (pUC31 was derived from pUC19, with additional Xho I, Bgl II, Bss HII and Nco I sites inserted between the Eco RI and Sac I sites of the polylinker). The 1.0 kb MoMuLV 3' LTR fragment from N2 (Eco RI-Eco RI) was cloned into plasmid $SK^+$ resulting in a construct called N2R3(−).

From the vector pAF/$Env^r$$SV_2$neo the 3.1 kb env DNA fragment (Xho I-Cla I) which also encodes rev, essential for env expression, was purified. From the plasmid N2R3(−), the 1.0 kb MoMuLV 3' LTR fragment (Cla I-Hind III) was purified.

The N2-based env expression vector was produced by a three-part ligation in which the 3.1 kb env fragment (Xho I-Cla I) and the 1.0 kb MoMuLV 3' LTR fragment (Cla I-Hind III) were inserted into Xho I-Cla I site of pUC 31/N2RS $g^M$.

A dominant selectable marker gene comprised of a SV40 early promoter driving expression of the neomycin phosphotransferase gene was inserted into the N2-based env expression vector at the Cla I site to facilitate isolation of infected and transfected cell lines. This vector was called KT-1.

B. Gag Expression Vector:

To efficiently express HIV gag and pol gene products in a retrovirus vector, two criteria must be met: 1) a REV response element (RRE) must be added to the vector to override repressive elements buried in gag and pol; and 2) REV must be efficiently expressed to interact with the RRE inserted in the vector, thus allowing for correct transport of viral messenger RNA into the cytoplasm.

A 2.5 kb Sac I-Eco RV DNA fragment was isolated from pBH10-R3 (see Ratner et al., op. cit.) and ligated into the Sac I-Sma I site of pUC31 along with a linker coding for a universal translation termination codon. pUC31 is derived from pUC19 with additional Xho I, Bgl II, Bss HII and Nco I sites inserted between the Eco RI and Kpn I sites of the poly linker. However, this construct contained the major splice donor (SD) site from HIV and thus could be problematic in virus generation. The SD site was removed by subcloning a 70 bp Rsa I-Cla I fragment with a 2.1 kb Cla I-Bam HI DNA fragment into the Hinc II-Bam HI site of $SK^+$. The Bam HI site was converted into a Cla I site by linker insertion. This construct was designated $SK^+$ gag protease SD delta.

A gag/pol SD deletion complete construct was produced by a three-part ligation reaction in which a 757 bp Xho-Spe I fragment from $SK^+$ gag protease SD delta and a 4.3 kb Spe I-Nco I fragment from BH10 R3 were inserted into $SK^+$ XhoI-Nco I. The Xba I site in $SK^+$ was converted to a Nco I to facilitate this reaction.

In order to introduce both REV and the REV responsive elements in the vector, a 1.4 kb Ssp I deletion in the plasmid $SK^+$ HIV env was generated. This deletion removed intronic sequences which are not important for REV expression (REV expression will continue to be from a spliced mRNA.) In addition, this deletion does not effect the REV responsive element located in env. The 1.1 kb DNA fragment coding for the dominant selectable marker Neo, engineered to contain a eukaryotic translation initiation codon, was introduced into the construct at the Bgl II site in env. Insertion of neo facilitates detection of passaged virus as well as selection for virus in an unspliced state during passage. A promoter such as the CMV is inserted into the XhoI site of this construct. This construct is designated $SK^+$ CMV/REV/Neo. The final viral construct may be produced by a four-part ligation reaction. A 2.5 kb Xho I-Xba I DNA fragment from $SK^+$ gag/polymerase SD delta, a 3.5 kb Spe I-Cla I DNA fragment from $SK^+$ CMV/REV/Neo and a 1.2 kb Cla I-Hind III DNA fragment from N2R3(−) (a subclone of N2 containing only the 3' LTR) are inserted into pUC N2R5 (a subclone of $N_2$ containing the 5' LTR) at the Xho I-Hind III site of this construct.

C. Gag/Pol Expression Using N2-Based Vector:

Efficient expression of HIV gag/pol gene products requires a REV response element (RRE) and REV (as discussed above, see "Gag Expression Vector").

To obtain REV and RRE, a 2.7 kb Kpn I-Xho I DNA fragment was isolated from the HIV proviral clone BH10-R3 (for sequence, see Ratner et al., *Nature* 313:277, 1985) and a 400 bp Sal I-Kpn I DNA fragment from exE7deltaenv (a Bal 31 deletion to nt 5496) was ligated into the Sal I site in the plasmid $SK^+$. This construct was called $SK^+$ env$^r$. A 239 bp 5'REV DNA fragment (Xho I-Ssp I) and a 4.2 kb RRE/3'REV in $SK^+$ fragment (Xho-I-Bgl II) were isolated from $SK^+$ envr.

To obtain the gag/pol gene, a 2.5 kb Sac I-Eco RI DNA fragment was isolated from pBH10-R3 (see Ratner et al., supra) and ligated into the Sac I-Sma I site of pUC31 along with a linker coding for a universal translation termination codon. However, this construct contained the major splice donor (SD) site from HIV and thus could be problematic in virus generation. The SD site was removed by subcloning a 70 bp RSA I-Cla I fragment with a 2.1 kb Cla I-Bam HI DNA fragment into the Hind II-Bam HI site of $SK^+$. The Bam HI site was converted into a Cla I site by linker insertion. This construct was designated $SK^+$ gag protease SD delta.

A gag/pol SD deletion complete construct was produced by a three-part ligation in which a 757 bp Xho I-Spe I fragment from $SK^+$ gag protease SD delta and a 4.3 kb Spe I-Nco I fragment from BH10-R3 were inserted into $SK^+$ Xho I-Nco I. The Xba I site in $SK^+$ was converted to a Nco I to facilitate this reaction. In addition, the Nde 1 site in pol was converted to an Xba I site. The resulting construct was called $SK^+$ gag/pol SD delta. The Xba I site from this construct was again converted to create a Bam HI site, and the 4.2 kb gag/pol DNA fragment (Xho I/blunt-Bam HI) was isolated.

The $SK^+$ gag/pol expression vector was produced by a three-part ligation in which the 239 bp 5'REV DNA fragment (Xho-I-Ssp I) and the 4.2 kb gag/pol DNA fragment (Xho I/blunt-Bam HI) were inserted into the Xho I-Bgl II 4.2 kb RRE/3'REV in $SK^+$ vector fragment. The resulting construct was called $SK^+$ gag/pol/RRE/REV.

The N2-based gag/pol expression vector was produced by a two-part ligation in which the 5.7 kb gag/pol/RR/Rz-V fragment (Xho I-Cla I), from $SK^+$ gag/pol/RRE/REV, was inserted into the Xho I-Cla I site of pUC31/N2R5 $g^M$.

A dominant selectable marker gene fragment from N2 (EcoRI-EcoRI comprised of a SV40 early promoter driving expression of the neomycin phosphotransferase gene was cloned into plasmid $SK^+$. From this a 1.3 kb neo gene fragment (Cla1-Bst B1) was inserted into the Cla I site of the N2-based gag/pol expression vector to facilitate isolation of infected and transfected cell lines. This vector was called KT-2

D. Gac-Protease -RT Exression Using N2-based Vector

Efficient expression of gag-protease-reverse transcriptase (gag-protease-RT) gene products (gag/prot) requires RRE and REV (as discussed above, see "Gag Expression Vector").

REV and RRE were obtained as described above (see "Gag/pol Expression Using N2-based Vector").

The gag gene contains a major splice donor (SD) site which could be a problem in virus generation. The SD site was removed by changing GT to AC (nt 744,745) by site-directed in vitro mutagenesis of pSLCATdelBgl II (a vector that expresses gag/pol, tat, and rev, derived from HIV strain HXB2). A Sac I site was also created upstream of the SD delta site so that a 780 bp SD delta gag fragment (Sac I-Spe I) could be purified. A 1.5 kb gag-prot-RT fragment (Spe I-EcoRV) and the 780 bp SD delta gag fragment (Sac I-Spe I) were inserted into pUC18 (Sac I-Sma I). The resulting 2.3 kb SD delta gag-prot-RT fragment (Sac I/blunt-Bam HI) was isolated from this pUC18 vector.

The $SK^+$ gag-prot-RT expression vector was produced by a three-part ligation in which the 239 bp 5'REV DNA fragment (Xho I-Ssp I) and the 2.3 kb SD delta gag-prot-RT fragment (Sac I/blunt-Bam HI) were inserted into the Xho I-Bgl II 4.2 kb RRE/3'REV in $SK^+$ vector fragment. The resulting construct was called $SK^+$ gag-prot-RT/RRE/REV.

The N2-based gag-prot-RT expression vector was produced by a two-part ligation in which the 3.8 kb gag-prot-RT/RRE/REV fragment (Xho I-Cla I), from SK+ gag-prot-RT-RRE/REV, was inserted into the Xho I-Cla I site of pUC31/N2R5 $g^M$.

A dominant selectable marker gene fragment from N2 (EcoRA-EcoR1), comprised of a SV40 early promoter driving expression of the neomycin phosphotransferase gene, was cloned into plasmid SK+. From this, a 1.3 Kb neo gene fragment (Clal-Bst BI) was inserted into the N2-based gag/pol-RT expression vector at the Cla I site to facilitate isolation of infected and transfected cell lines. This vector was called KT-3.

E. Construction of H2-Dd expression vectors

The murine class I gene encoding H2-Dd gene was cloned into a Bluescript™ SK+ plasmid containing either the CMV promoter or the RSV LTR inserted upstream of the H2-Dd gene. The expression constructs RSV-Dd and CMV-Dd were transfected into 3T3 cells using the $CaPO_4$/polybrene method.

The expression constructs CXV-Dd and MV7.T4 (a retroviral construct expressing human CD4 and neomycin phosphotransferase) were co-transfected into human HT1080 cells. The cells were selected with G418 and resistant colonies were picked, expanded and tested for expression of H2-Dd by Western blot using a rat anti-Dd antibody. One of the positive clones (A-9) was infected with N2env-neo (KT-1).

F. Construction of HIV envelope deletions for CTL epitone mapping:

Two retroviral vectors were prepared for mapping the regions in the HIV envelope proteins which contain peptide epitopes reactive with CTL. The first, referred to as Δloop, contains a deletion of the gp120 hypervariable loop which is a region of the HIV IIIB envelope protein reactive with antibody in patient's sera. The second, referred to as "Chunk I", contains only the envelope region of HIV IIIB envelope from the amino terminal up to the beginning of the gp120 loop and also lacks the membrane gp41 "tail" of the envelope protein.

1. ΔLoop

A 602 base pair Hinc II-Sca I fragment of HIV IIB env was prepared and inserted into plasmid 130B. A 43-mer oligo 5' G AAC CAA TCT GTA GAA ATT AAT AAC AAT AGT AGA GCA AAA TGG 3' was synthesized. Mutagenesis of the mismatched primer was done by the method of Kunkel (Kunkel, T. A. Proc. Natl. Acad. Sci. USA 82:448–493, 1985) to generate an in frame deletion of 106 amino acids. This was confirmed by DNA sequencing. The Stu I-Aoc I fragment containing the deletion was then inserted into the same sites of HIV IIIb env that was carried in Bluescript SK+ (Stratagene, La Jolla). From this intermediate, the Xho I-Cla I fragment of HIV env IIIB containing the deletion was inserted into the same sites of a modified N2 retroviral vector. (This vector did not have the gag ATG start codon.) The SV2neo gene was lastly inserted into the Cla I site in the sense orientation.

2. Chunk I

The 1.30 kb Xho I-PVU II fragment of HIV IIIB env was cloned into the Bluescript SK+ vector (Stratagene, La Jolla) at the Xho I-Hinc II sites. This fragment was then reisolated from the vector as Xho I-Bam HI fragment (Bam HI site from the polylinker) and inserted into the Xho I-Bgl II sites of HIV env IIIB carried either in the KT-1 retroviral vector or a CMV construct expressing HIV IIIB env.

These plasmids, when placed in a suitable packaging cell, expressed a retroviral vector construct which contains a packaging signal. The packaging signal directed packaging of the vector construct into a capsid and envelope along with all further proteins required for viable retroviral particles. The capsid, envelope, and other proteins are preferably produced from one or more plasmids containing suitable genomes placed in the packaging cell. Such genomes may be proviral constructs, which in a simple case may merely have the packaging signal deleted. As a result, only the vector will be packaged. Suitable packaging or packaging cell lines, and the genome necessary for accomplishing such packaging, are described in Miller et al. (*Mol. Cell. Bio.* 6:2895, 1986), which is incorporated herein by reference. As described by Miller et al., it is preferable that further changes be made to the proviral construct other than simple deletion of the packaging signal in order to reduce the chances of recombination events occurring within the packaging cell line, which may result in production of viral particles which are not replication defective.

It will be understood that Example 1 is merely illustrative of a procedure for generating an HIV envelope glycoprotein (gp) or other viral antigen. It is also possible to provide a proviral vector construct which expresses a modified HIV envelope gp on the target cells which will likewise stimulate an immune response, but with less T-cell cytopathic effects. Envelope glycoproteins can be suitably modified using techniques well known in the art, for instance through use of the disclosure of articles such as Kowalski et al. (*Science* 237:1351, 1987), which is herein incorporated by reference. The envelope of the human immunodeficiency virus type 1 (HIV-1) plays a central role in the process of virus entry into the host cell and in the cytopathicity of the virus for lymphocytes bearing the CD-4 molecule. Mutations that affect the ability of the envelope glycoprotein to form syncytia in CD4+ cells can be divided into five groups: those that decrease the binding of the envelope protein to the CD4 molecule, those that prevent a post-binding fusion reaction, those that disrupt the anchorage of the envelope glycoprotein in the membrane, those that affect the association of the two subunits of the envelope glycoprotein, and those that affect post-translational proteolytic processing of the envelope precursor protein.

To define the relation between the structure of the HIV-1 envelope glycoprotein and the ability to form syncytia, Kowalski et al. introduced deletion and insertion mutations into a plasmid, pIIIenv3, that encodes the envelope glycoprotein derived from the HTLV-IIIB strain of HIV-1.

The integral membrane protein (gp41) of HIV-1 differs from that of most retroviruses in the presence of additional sequences at the carboxyl terminus. The gp41 on the carboxyl-terminal side of the probable membrane-spanning region consists of a hydrophilic region (residues 724–745) and a terminal region (residues 745–856) of alternating hydrophilic and hydrophobic character. In Kowalski et al., large deletions of either of these regions resulted in mutant env proteins that efficiently formed syncytia [see plasmids pIIIenvΔ(727–751), Δ813, and Δ753]. However, deletion of both of these regions (pIIIenvΔ727) resulted in very low levels of env protein production and loss of syncytium formation. When the deleted sequences were replaced by sequences derived from the art gene or by random sequences that have varying degrees of hydrophobic or hydrophilic character, syncytium induction was observed (for example, pIIIenvΔ722S, Δ725S, and Δ732S). The art protein-derived amino acid sequence could be introduced in the amino-terminal direction up to amino acid 705 without eliminating the ability of the mutated env protein to yield syncytia (pIIIenvΔ705S). However, substitution of the identical amino acid sequences on the amino-terminal side of residue 705 (for example, the products encoded by pIIIenvΔ700S or pIIIenvΔ697S) resulted in undetectable levels of cell-associated env protein and lack of syncytium formation. These studies, which are described in koeslski et al., indicate that gp41 sequences on the carboxyl-terminal side of residue 705 are not necessary for the functions of the envelope involved in the formation of syncytia.

To examine the effect of deletion of the probable membrane-spanning region of gp41 (residues 666–722), Kowalski et al. introduced translation termination codons in positions corresponding to amino acids 472, 517, 641, and 665 (pIIIenvΔ472S, Δ517, Δ641, and Δ665). Additionally, a series of polar amino acids were introduced into the region between amino acids 666 and 722 (pIIIenvΔ705S, Δ700S, and Δ697S). The level of cell-associated env products was markedly reduced for all of these mutants compared with the wild-type envelope in Kowalski et al.

by contrast, in further experiments described in Kowalski et al., an env product with a deletion of 39 amino acids from the carboxyl terminus of gp 120 (made by plasmids pIIIenvΔ472S) did not bind to the $CD4^+$ SupT1 cells. Thus, the addition of 6 or 130 amino acids derived from gp41 did not eliminate the ability of the exterior envelope protein to bind to the CD4 molecule, whereas a deletion near the carboxyl terminus of gp120 disrupted CD4 binding.

Also described in Kowalski et al., a series of four or five amnio acids in-frame insertion mutants were created through the env gene. One set of these mutants (pIIIenv103, 252, 287, 342, and 448) that fail to form synctia upon transfection of $CD4^+$ cells was defective in the synthesis of gp120 as determined by immunoprecipitation of the labeled cell lysates or of cell-free supernatants.

Additionally, in Kowalski et al., two sets of insertion mutations that eliminate synctium formation dramatically reduced the amount of gp120 associated with the cell yet produced abundant gp120 in the supernatant. One set of these mutants is located in the amino-terminal half of gp120 (pIIIenv65, 129, 174, 204, and 308) and the second set is located in the amino-terminal half of gp41 (pIIIenv530, 537, 640A, and 640B). The amount of cell-associated gp160 produced by these mutants is near normal. These mutations apparently disrupt the association of the gp120 and gp41 env glycoproteins. Thus, a proviral construct may be constructed by the above technique which generates retroviral constructs expressing such a suitably modified gp. This construct is then placed in a packaging cell as described above. The resulting recombinant retroviruses produced from the packaging cell lines may be used in vitro and in vivo to stimulate an immune response through the infection of susceptible target cells. The nucleic acids introduced by these means into the susceptible target cell may become integrated into the nucleic acid of the target cell. It will be appreciated that other proteins expressed from the HIV genome, such as gag, pol, vif, nef, etc., may also elicit beneficial cellular responses in HIV-infected individuals. Proviral vectors such as those described below are designed to express such proteins so as to encourage a clinically beneficial immune response. It may be necessary for certain vectors to include rev coding sequences as well as a rev responsive element (Rosen et al., Proc. Natl. Acad. Sci. 85:2071, 1988).

The following example demonstrates the ability of syngeneic cells expressing a foreign antigen after vector treatment to: (a) elicit CTL responses in mice by injecting either infected syngeneic cells or preparations of infectious vector; (b) elicit CTL responses in a human in vitro culture system; (c) to infect human, chimpanzee and macaque cells, including primary cells, so that these can be used to elicit CTL responses and can serve as targets in CTL assays; (d) map immune response epitopes; and (e) elicit and measure CTL responses to other non-HIV antigens such as mouse CMV (MCMV).

EXAMPLE 2

A. Immune Response to Retroviral Vector-Encoded Antigens

Figure 1A:
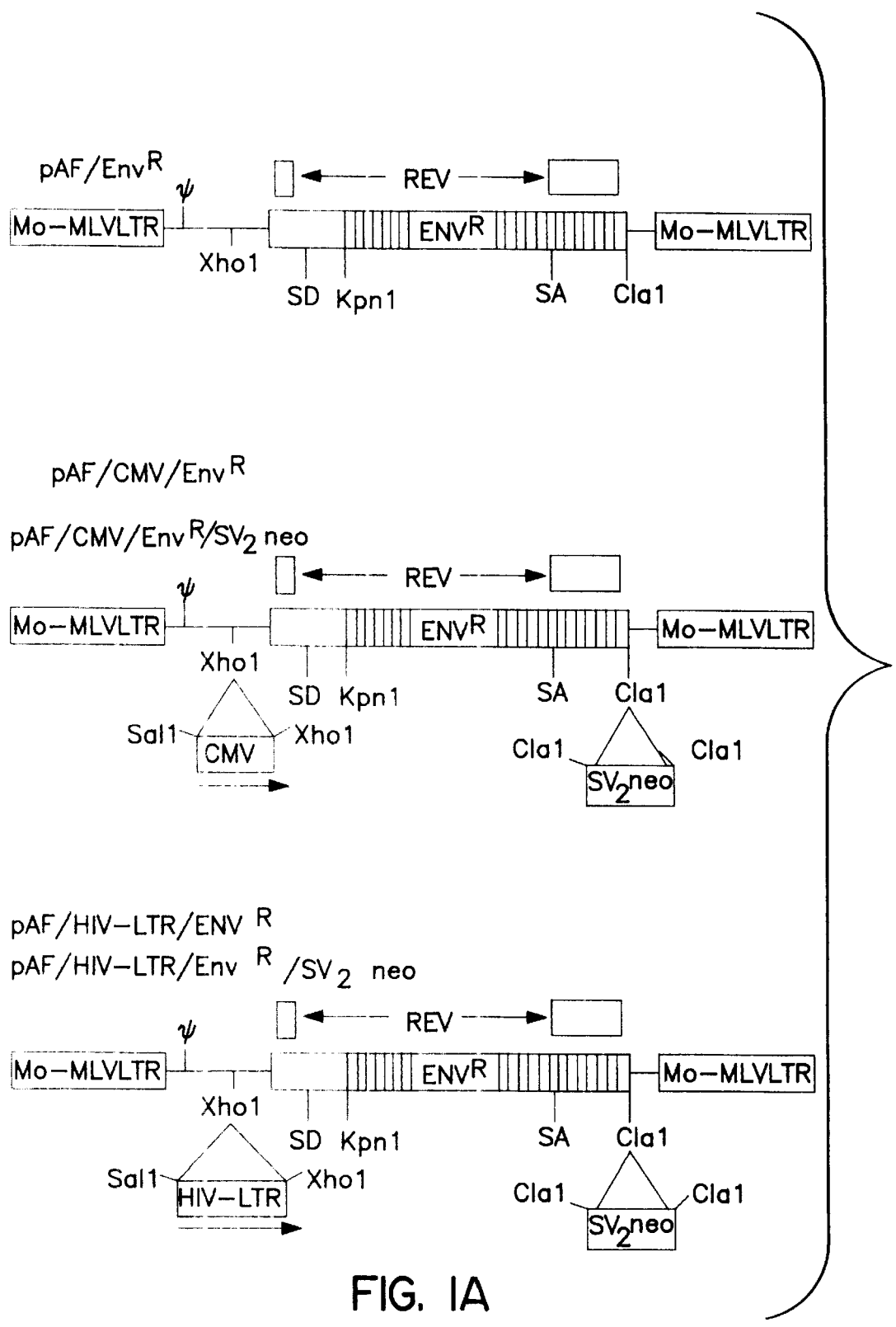
Figure 1B:
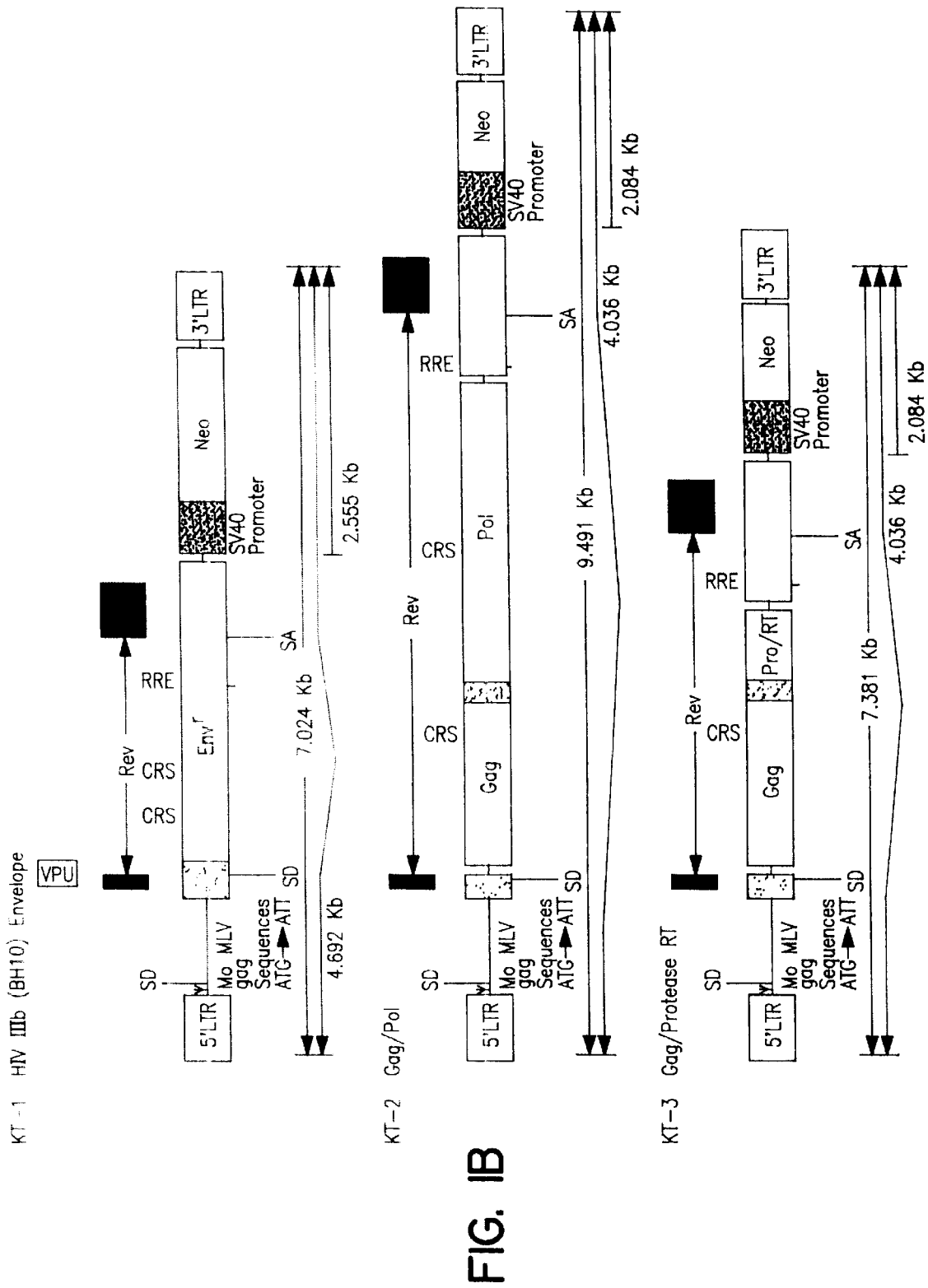
Figure 1C:
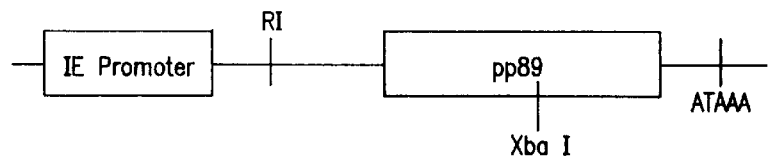
Figure 1C:
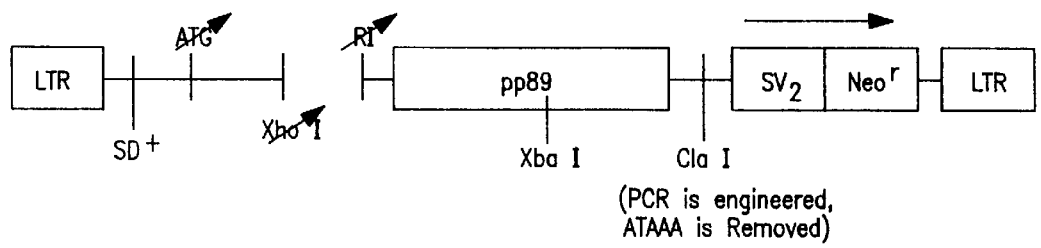
Figure 1C:
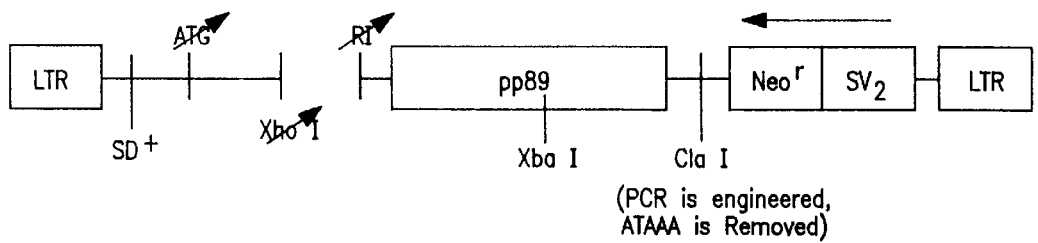
Figure 2:
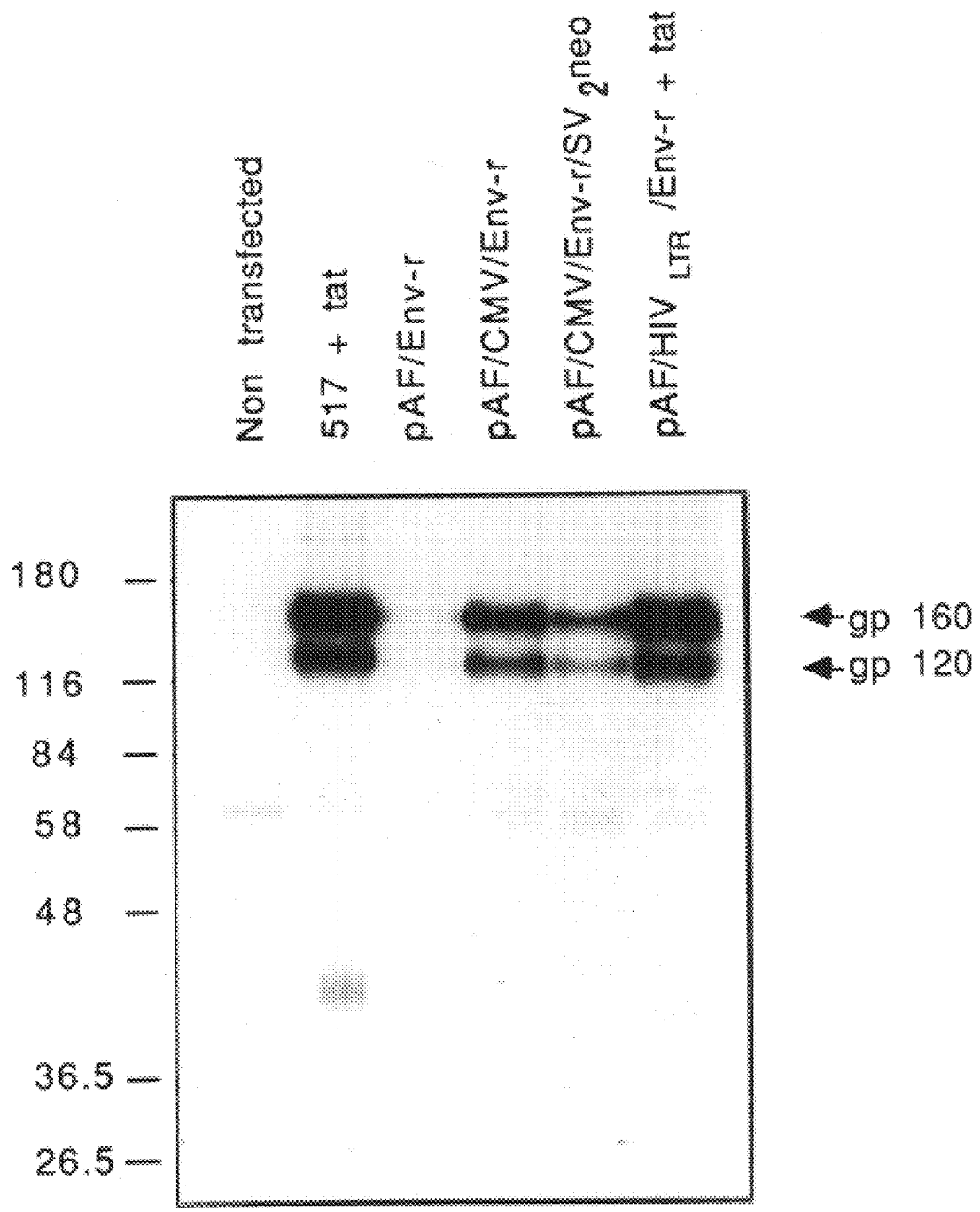
Figure 3:
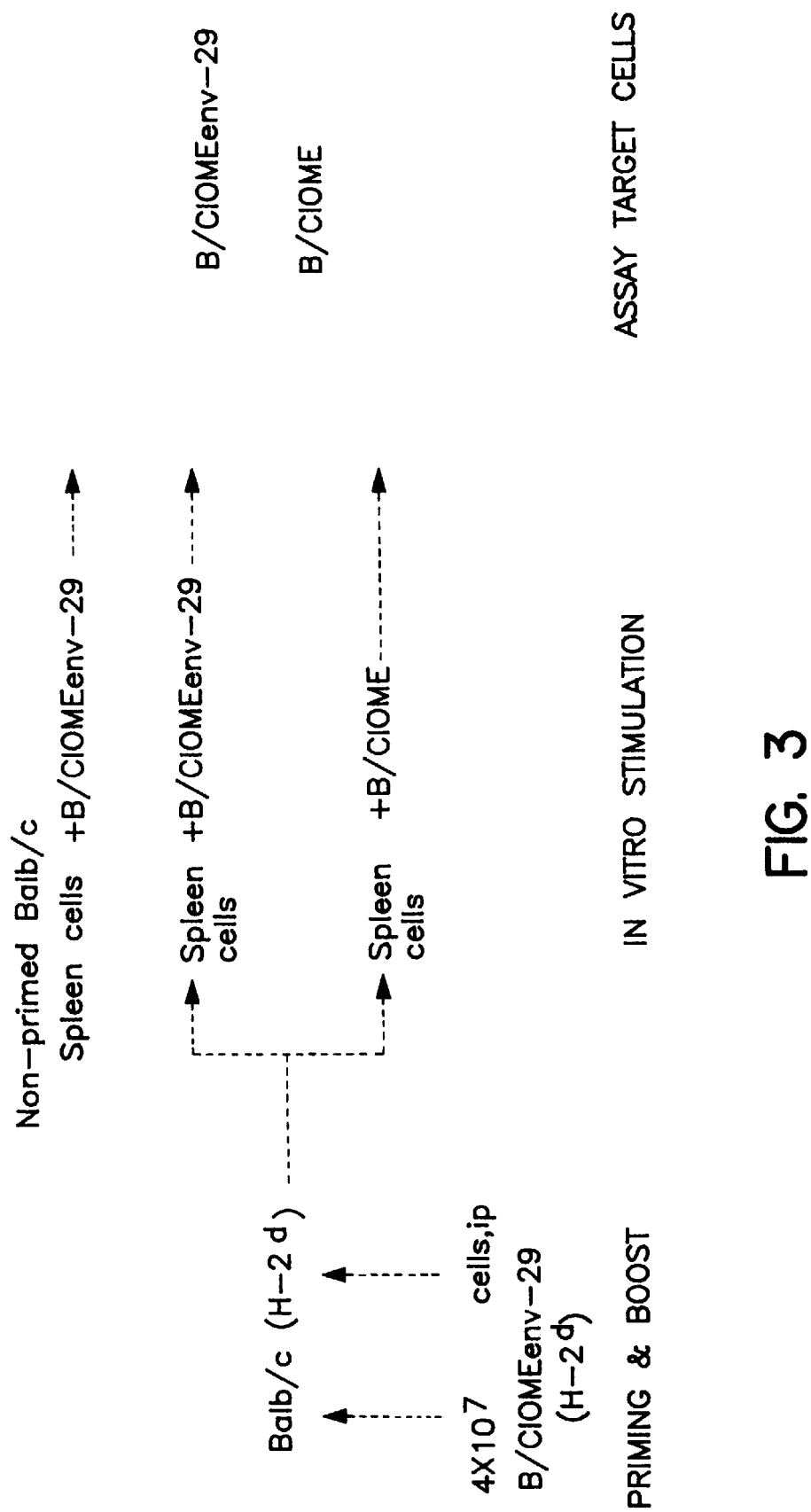

A murine tumor cell line (B/C10ME) ($H_{-2}^d$) (Patek et al., Cell. Immunol. 72:113, 1982) was infected with a recombinant retrovirus carrying the $pAF/Env^r/SV_2neo$ vector construct coding for HIV env. One cloned HIV-env expressing cell line (B/C10ME-29) was then utilized to stimulate HIV-env-specific CTL in syngeneic (i.e., MHC identical) Balb/c ($H_{-2}^d$) mice (see FIG. 3). Mice were immunized by intraperitoneal injection with B/C10ME-29 cells ($1 \times 10^7$ cells) and boosted on day 7–14. (Boosting was not absolutely required.) Responder spleen cell suspensions were prepared from these immunized mice and the cells cultured in vitro for 4 days in the presence of either B/C10ME-29 (BCenv) or B/C10ME (BC) mitomycin-C-treated cells at a stimulator-:responder cell ratio of 1:50 (FIG. 3). The effector cells were harvested from these cultures, counted, and mixed with radiolabeled ($^{51}Cr$) target cells (i.e., B/C10MEenv-29 or B/C10ME) at various effector:target (E:T) cell ratios in a standard 4–5 hr $^{51}Cr$-release assay. Following incubation, the microtitre plates were centrifuged, 100 ul of culture supernate was removed, and the amount of radiolabel released from lysed cells quantitated in a Beckman gamma spectrometer. Target cell lysis was calculated as: % Target Lysis=Exp CP−SR CPM/MR CPM−SR CPM×100, where experimental counts per minute (Exp CPM) represents effectors plus targets; spontaneous release (SR) CPM represents targets alone; and maximum release (MR) CPM represents targets in the presence of 1M HCl.

Figures 1, 4A:
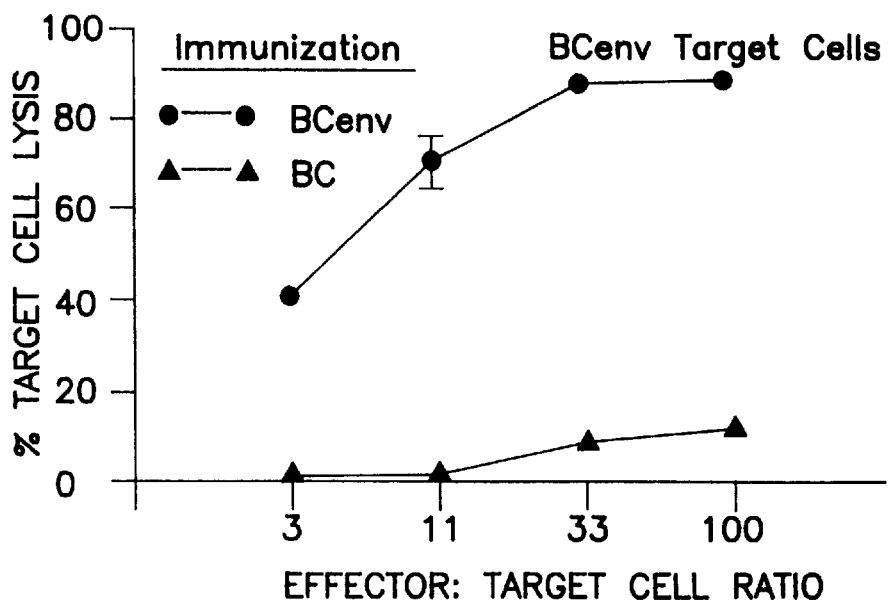
FIG. 4S depicts the CTL response in Balb/c mice to cells expressing the MCMV pp89 protein (BC pp89 #9) measured on BC cells infected with 62/3, 53-7, 51-1 (all expressing pp89), KT1 (BC-env 14H expressing HIV env) or with no treatment (BC).
Figures 2, 4A:
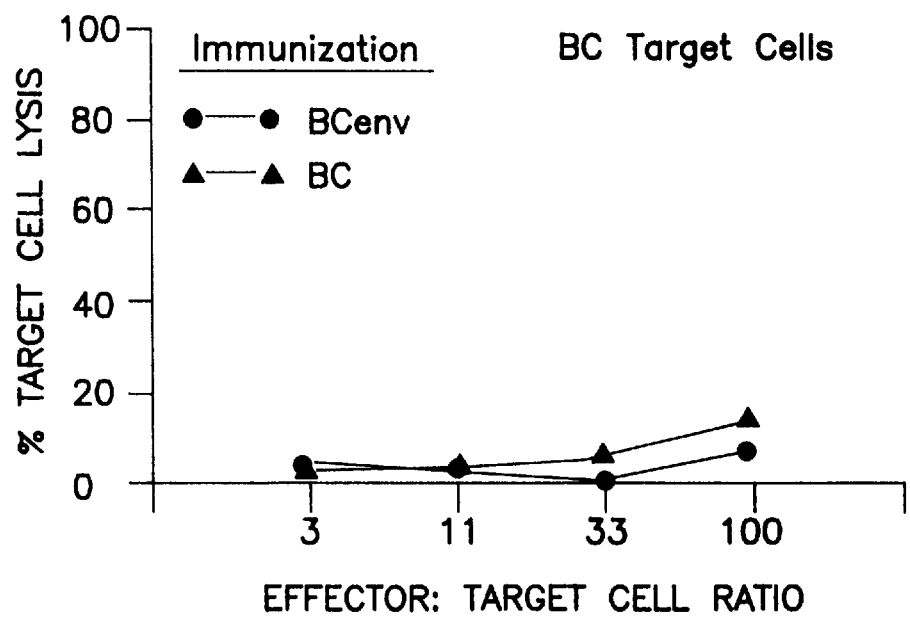

The results (FIG. 4A) illustrate that CTL effectors were induced which specifically lysed HIV-env-expressing target cells (BCenv) significantly more efficiently than non-HIV env BC targets. Primed spleen cells restimulated in vitro with non-HIV-env-expressing control cells (B/C10ME) did not show significant CTL activity on either B/C10MEenv-29 or B/C10ME targets, particularly at lower E:T cell ratios. Spleen cells obtained from naive nonimmunized Balb/c mice which were stimulated in vitro with B/C10MEenv-29 did not generate CTL (data not shown), thus suggesting the importance of the in vivo priming and boosting event. This experiment has been repeated and similar results obtained.

Figure 4B:
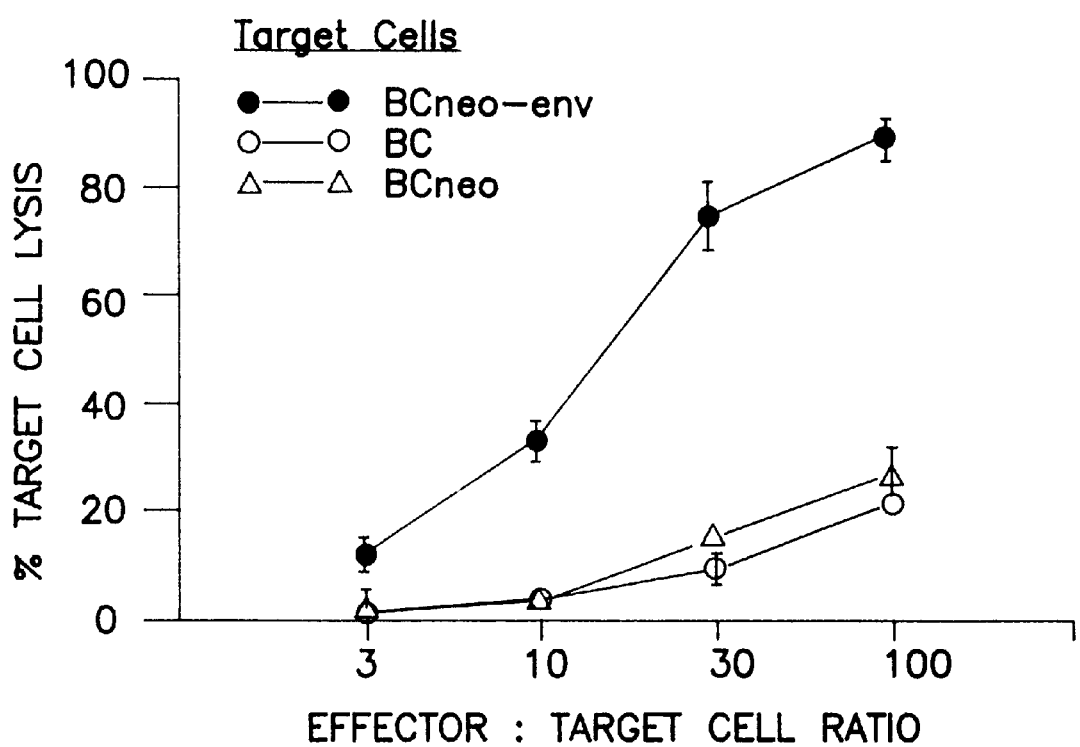

In another experiment, effector cells obtained from Balb/c mice immunized, boosted and restimulated in vitro with a different $H_{-2}^d$ HIV-env-expressing tumor cell clone (L33-41) infected with the same $pAF/Env^r/SV_2neo$ (HIV-env) vector construct were capable of lysing B/C10MEenv-29 target cells. This provides additional support that the CTL generated in these mice are specifically recognizing an expressed form of HIV-env rather than simply a unique tumor cell antigen on these cells. This result also suggests that the vector-delivered antigen is presented in a similar manner by the two tumor cell lines. The specificity of the CTL response was further demonstrated by testing effector cells obtained from BCenv immunized mice on BCenv target cells expressing the neo and HIV env genes, BC (non-neo, non-HIV env) parental targets and BCneo target cells expressing the nec resistance marker gene, but no HIV env. FIG. 4B indicates that the CTL responses are specific for the HIV env protein.

Figure 4C:
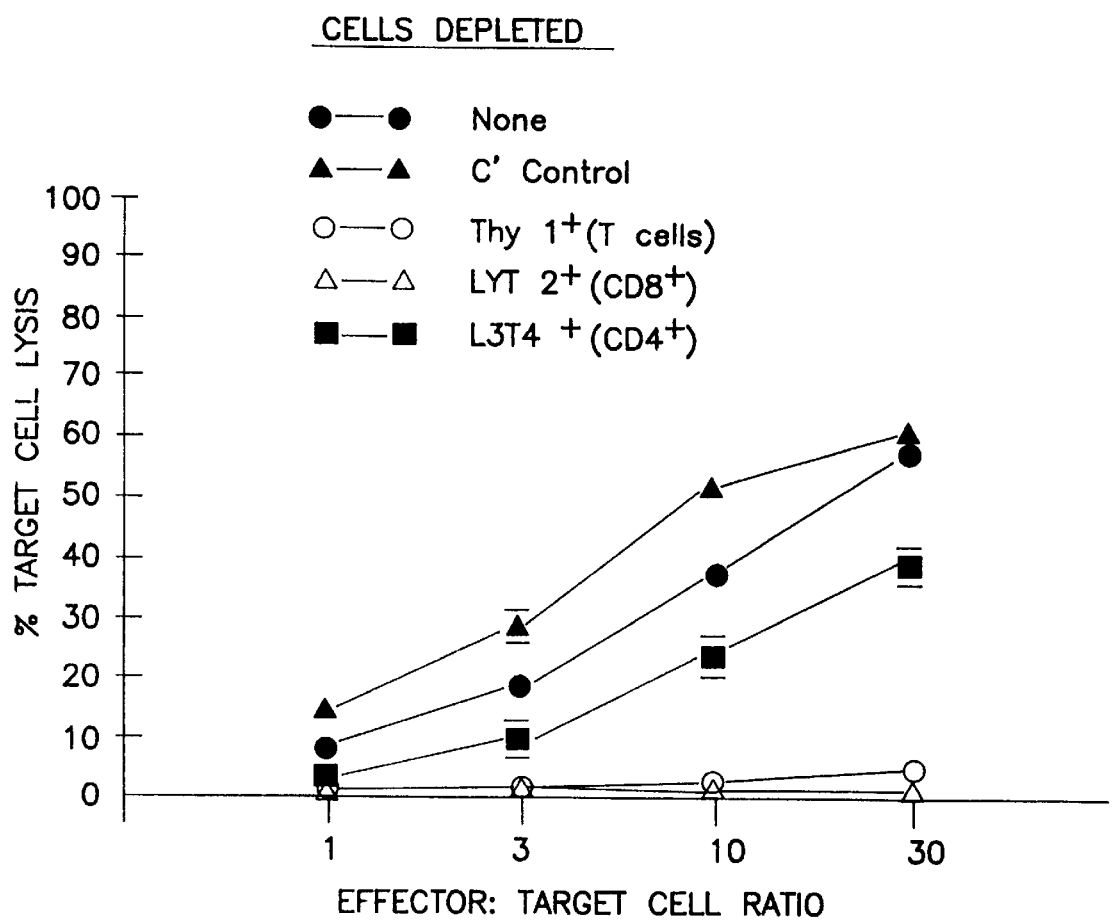

In another experiment, effector cells obtained from mice immunized with 1×10[7] BCenv cells, boosted and restimulated in vitro, were treated with T-cell-specific monoclonal antibodies (Mab) plus complement (C') in order to determine the phenotype of the induced cytotoxic effector cells. Effectors were treated with either anti-Thy 1.2 (CD3), anti-L3T4 (CD4; RL172.4, Ceredig et al., *Nature* 314:98, 1985) or anti-Lyt 2.2 (CD8) Mab for 30 minutes at 4° C, washed 1 time in Hank's balanced salt solution (HBSS), resuspended in low tox rabbit C' and incubated 30 minutes at 37° C. The treated cells were washed 3 times in RPMI 1640 complete medium, counted, and tested for their ability to lyse BCenv radio-labeled target cells as previously described. FIG. 4C shows that treatment with either anti-Thy 1.2 or anti-Lyt 2.2 Mab+C' abrogated cytotoxic activity, whereas treatment with anti-L3T4 Mab+C' or C' alone did not significantly affect cytotoxicity. These results indicate that the majority population of cytotoxic effector cells generated in this system are of the $CD3^+$ $CD4^-$ $CD8^+$ cytotoxic T-cell phenotype.

Figure 4D:
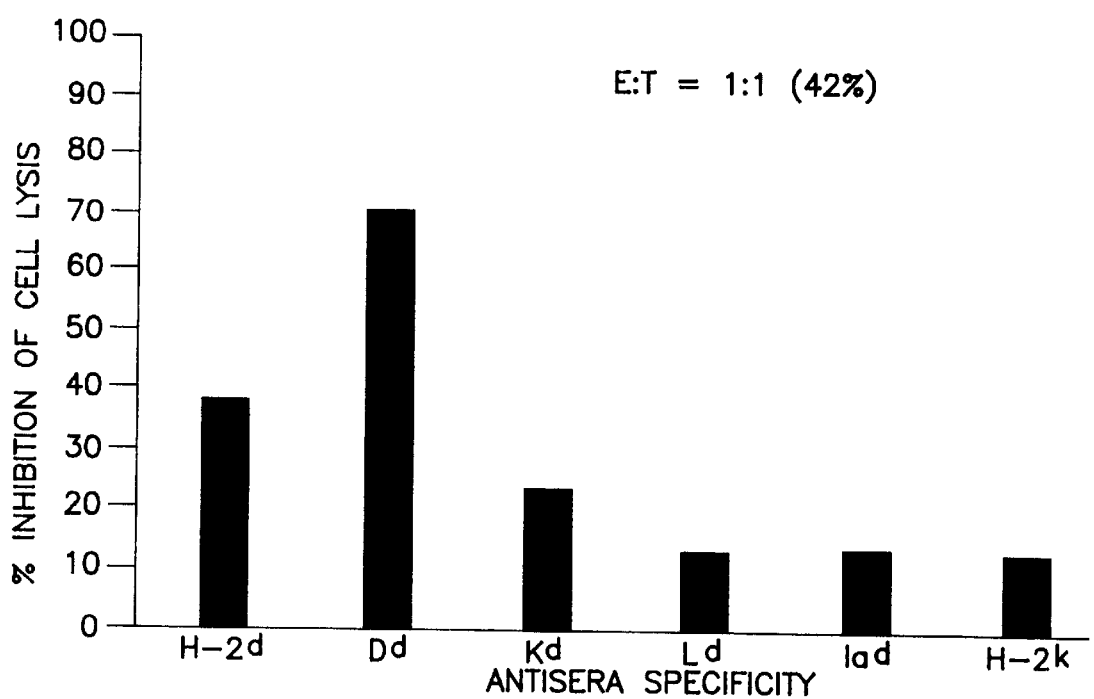

Experiments were performed to determine the MHC restriction of CTL effector cells described above. Polyclonal antibodies directed against different H-2 regions of the murine MHC (i.e., anti-$H-2^d$, anti-$H-2D^d$, anti-$H-2L^d$, anti-$H-2K^d$, anti-$H-2I^d$) were used to inhibit the CTL response on BCenv target cells. The anti-$H-2^k$ antiserum was used as a negative control. The data (FIG. 4D) indicate that the Balb/C anti-BCenv CTL response is inhibited primarily by the anti-$H-2D^d$ antiserum. This suggests that these CTL responses are restricted by MHC class I molecules, most likely encoded within the D region of the H-2 complex.

Figure 4E:
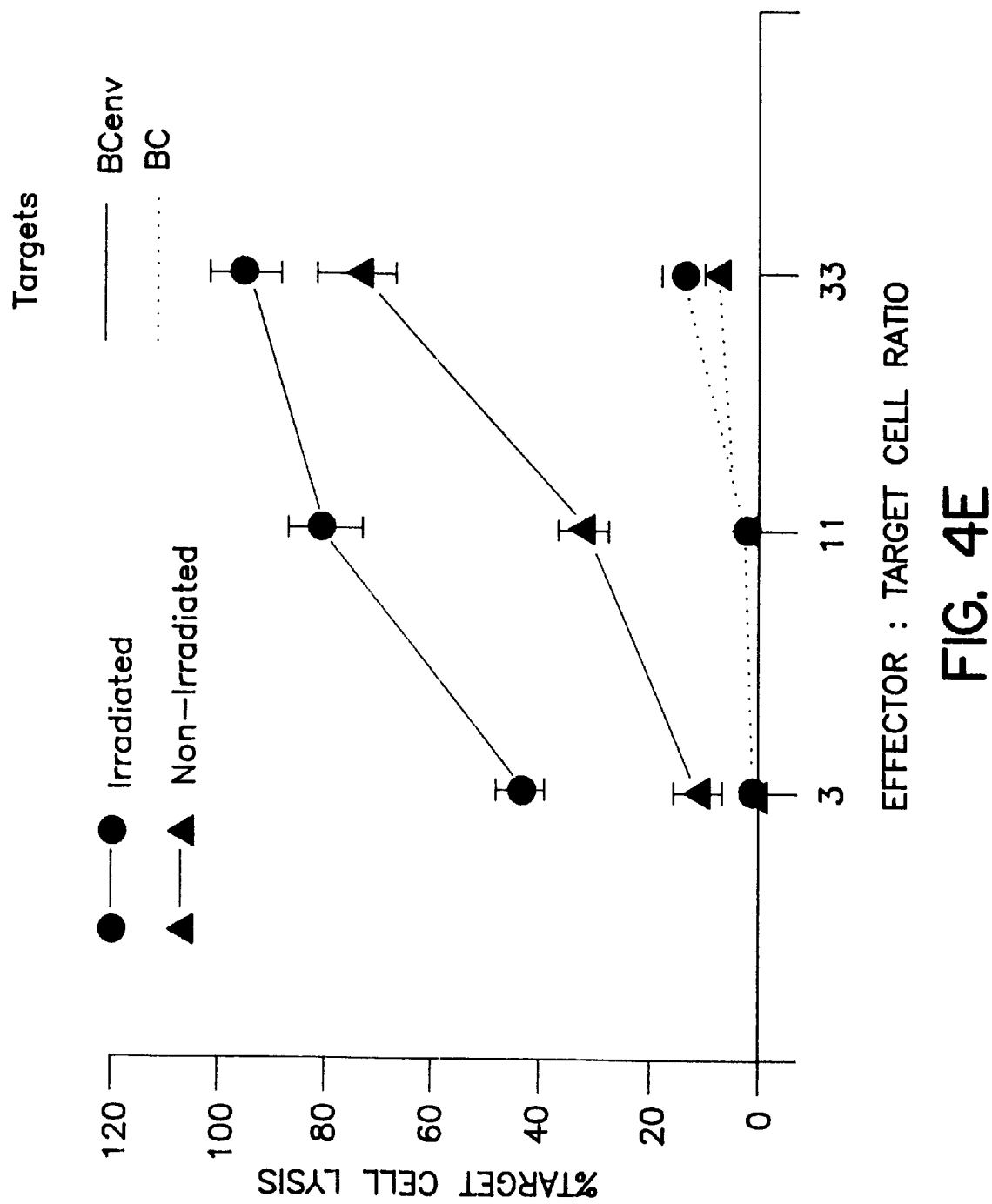

In addition to experiments in which mice were immunized with replication-competent HIV env-expressing tumor cells, tests were conducted to determine whether proliferating stimulator cells were necessary for inducing CTL in vivo. Mice were immunized with either irradiated (10,000 rads) or nonirradiated BCenv cells, and the primed spleen cells were later stimulated in vitro, as previously described. The resulting effector cells were tested for CTL activity on radiolabeled BCenv and BC target cells. FIG. 4E indicates HIV-specific CTL can be induced in vivo with either irradiated or nonirradiated stimulator cells. These data demonstrate that CTL induction by HIV env-expressing stimulator cells is not dependent upon proliferation of stimulator cells in vivo and that the presentation of HIV env antigen in the appropriate MHC context is sufficient for effective CTL induction. Formalin fixed cells also elicit an equivalent immune response. This shows that killed cells or perhaps cell membranes expressing the appropriate antigen in the proper MHC class I/II molecular context are sufficient for induction of effective CTL responses.

Figures 1, 4F:
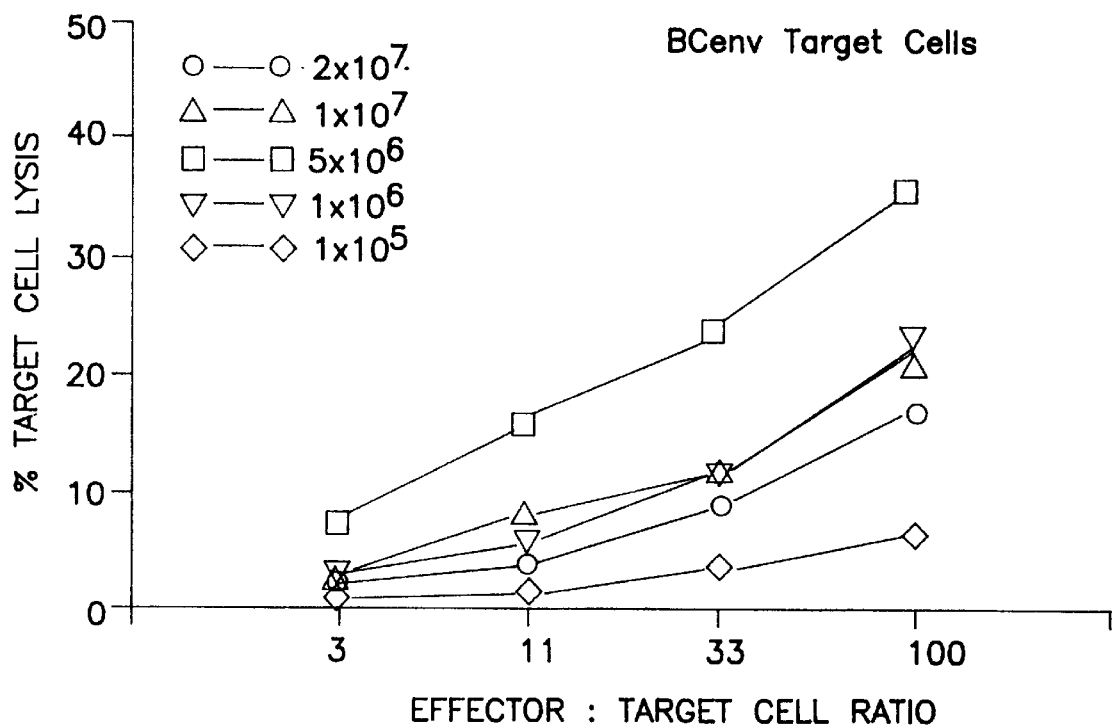
Figures 2, 4F:
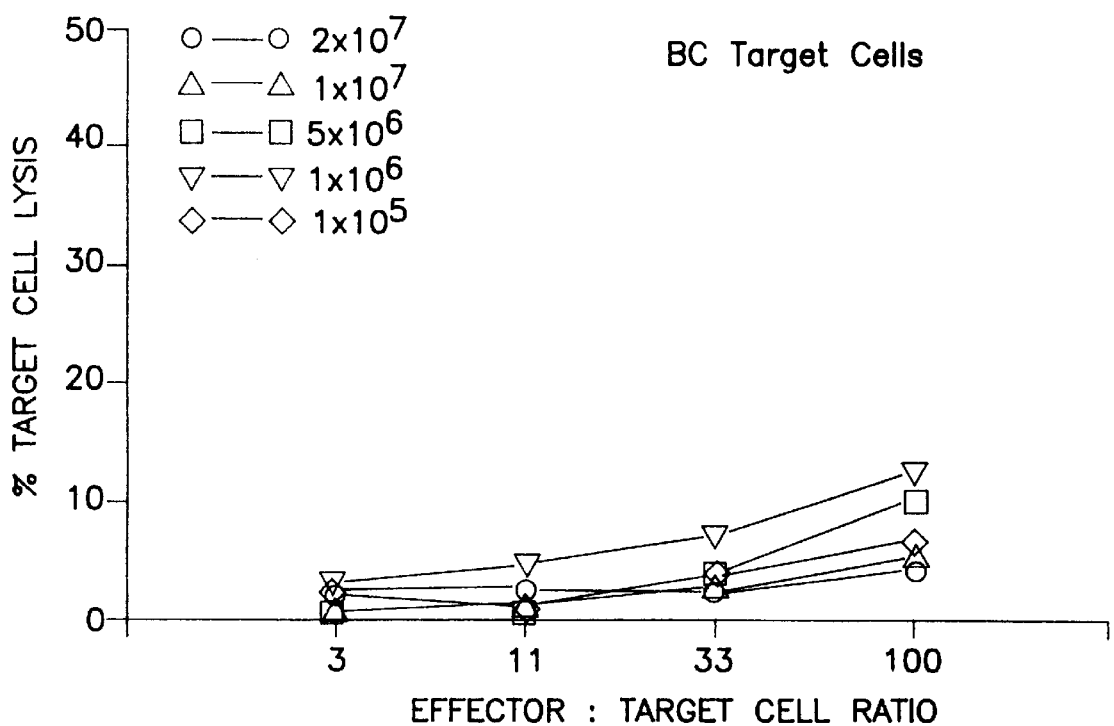

Additional experiments were performed to examine the optimal injection dose of BCenv cells into Balb/C mice. Mice were immunized with varying numbers of BCenv stimulator cells, restimulated in vitro as described, and tested for CTL activity. The results shown in FIG. 4F indicate that immunization of mice with 5×10[6] env-expressing BCenv-29 stimulator cells generated an optimal CTL response under these conditions.

Figures 1, 4G:
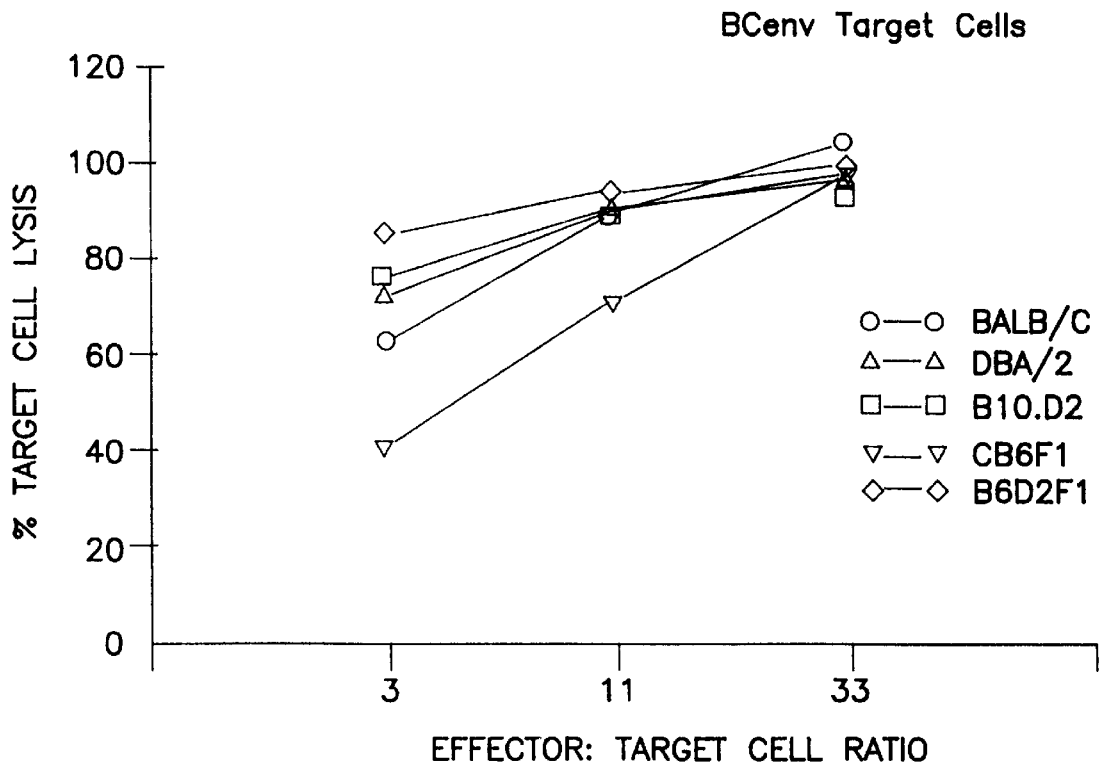
Figures 2, 4G:
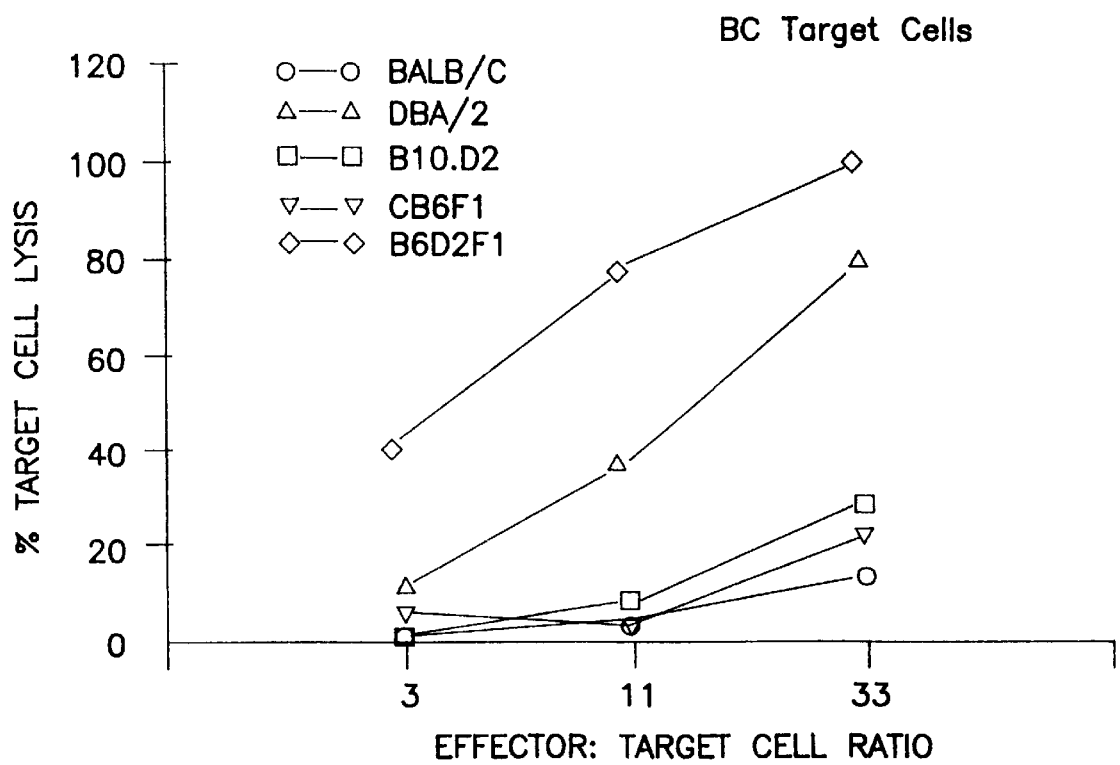

Further experiments examined the ability of vector-infected HIV env-expressing BCenv stimulator cells to induce CTL responses in other $H-2^d$ mouse strains other than Balb/C, in order to provide an indication as to genetic restrictions imposed on host responsiveness. Different strains of $H-2^d$ (i.e., Balb/C, DBA/2, B10.D2), as well as $H-2^d \times H-2^b$ F1 hybrid mice [i.e., CB6F1 (Balb/c×B6 F1); B6D2F1 (B6×DBA/2 F1)], were immunized with BCenv stimulator cells and examined for the induction of CTL responses. FIG. 4G illustrates that all strains including F1 hybrids generate CTL responses against the BCenv target cells to varying degrees. Although some strains also exhibit responses against the parental (i.e., non-HIV env) target cells, these responses are lower than those directed against the BCenv target.

Figure 4H:
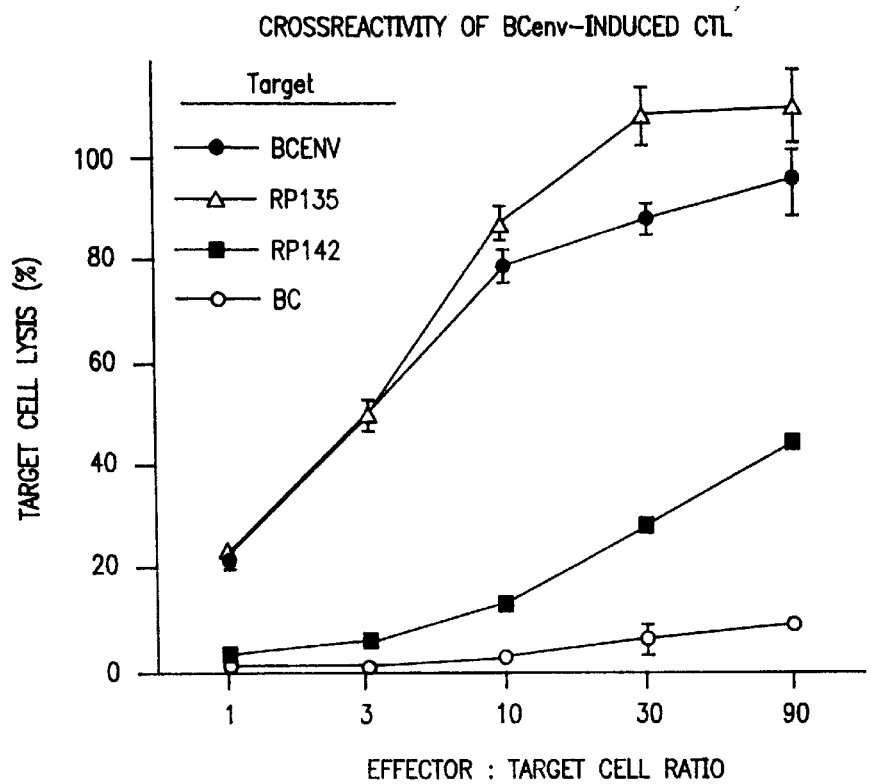

Experiments were also conducted to evaluate the ability of the vector-infected HIVenv (strain III B)-expressing BCenv stimulator cells to induce cross-reactive CTL responses against other strains of HIV (i.e., MN). FIG. 4H illustrates that CTL induced with the HIV env III B strain of vector-infected BC stimulator cells killed BC target calls coated with RP135 peptide (Javaherian et al., *Proc. Natl. Acad. Sci. USA* 86:6768, 1989) homologous with the 1IIB envelope sequence. These CTL also killed BC target cells coated with RP142 (i.e., peptide homologous with the HIV MN strain of envelope proteins) (Javaherian et al., *Proc. Natl. Acad. Sci. USA* 86:6768, 1989).

Figure 4I:
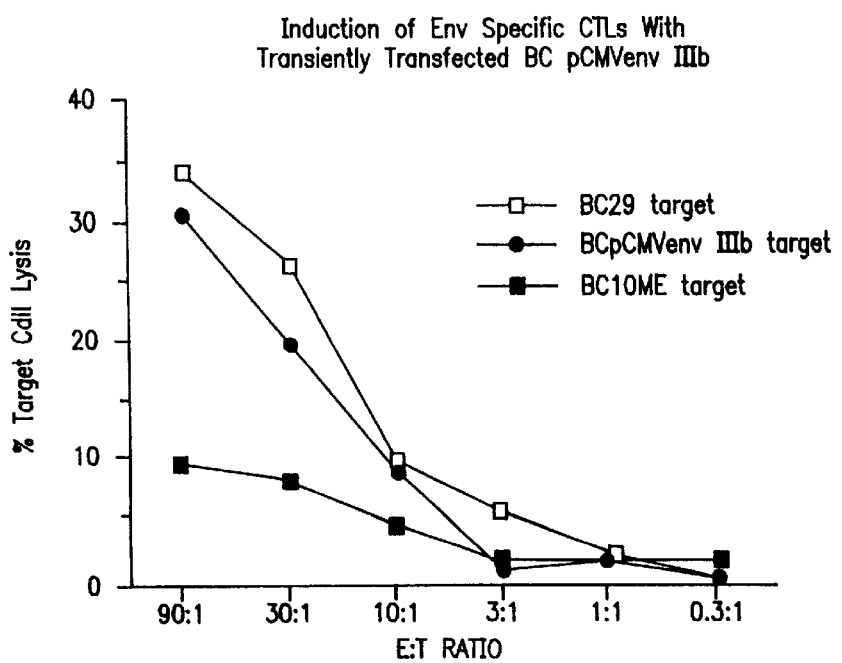
Figure 4J:
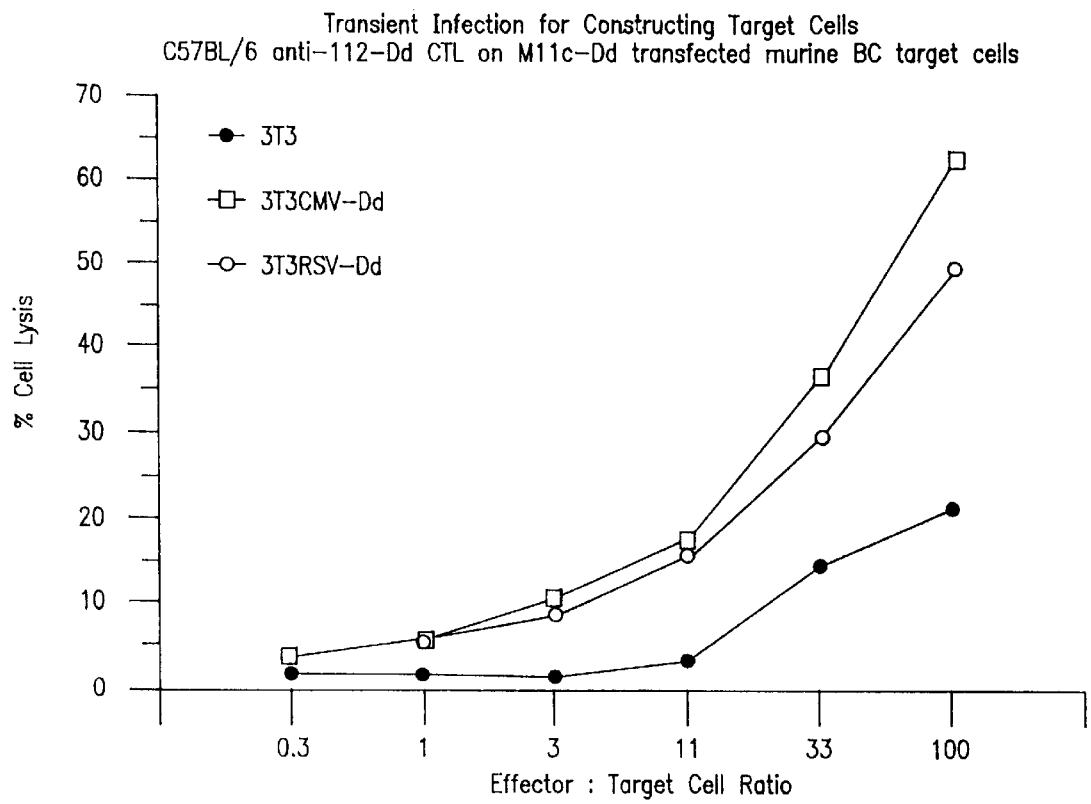

Additional experiments were conducted to examine the ability of transiently-HIVenv expressing stimulator cells to induce CTL responses in mice. These cells are distinguished from the BCenv stimulator cells, described above, by virtue of being infected with retroviral vector only two days prior to use and not being selected or cloned in vitro prior to use as stimulator cells, i.e., by injection into mice. The results presented in FIG. 4I illustrate that BC cells transfected two days before injection into mice with plasmid DNA having the HIVenv IIIb vector construct (in which the cmv promoter drives expression of HIV envelope protein; BCpcmvIIIb) induced specific CTL which could be restimulated with BCpcmvIIIb cells in vitro and would kill BCpcmvIIIb transiently-expressing target cells (BCpcmvenv IIIB target) as well as retrovirus-infected BC cells from a cell line which was cloned and selected for stable expression of HIVenvIIIb (BC-29 target). These specific immune CTL did not kill BC10ME control cells which do not express HIV envelope proteins. Thus, B/C cells transiently-expressing HIV envelope proteins can serve as effective inducers of immune CTL responses in vitro, restimulators of immune CTL in vitro (i.e., for use in CTL assays, etc.), and target cells for lysis by immune CTL in vitro. In addition, the results of similar experiments are presented graphically in FIG. 4J which illustrates that BC calls transiently-expressing H2-Dd serve as target cells for lysis by H2-Dd alloimmune CTL.

Figure 4K:
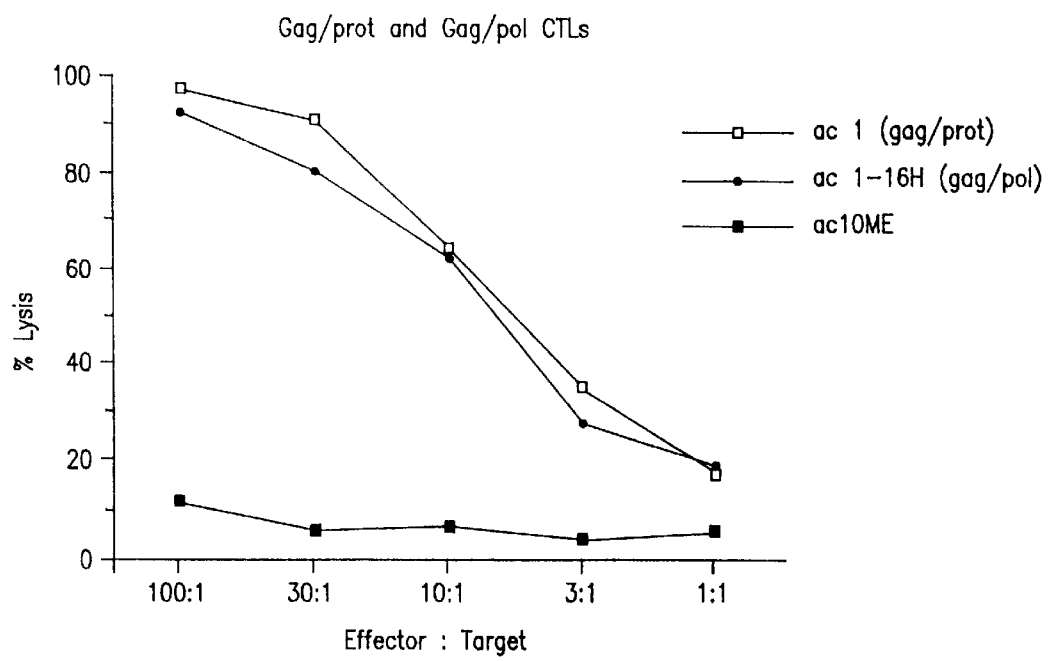

To evaluate the ability of other retroviral vector-encoded HIV antigens to induce an immune response in mice, experiments were also conducted with retroviral constructs encoding gag/pol and gag/prot. The results presented in FIG. 4K illustrates that murine CTL are induced by immunization with either gag/pol or gag/prot wich can kill their respective target cells, i.e., either BC-1–16H cells (i.e., infected with the gag/pol vector) or BC 1 cells (i.e., infected with the gag/prot vector).

Figure 4L:
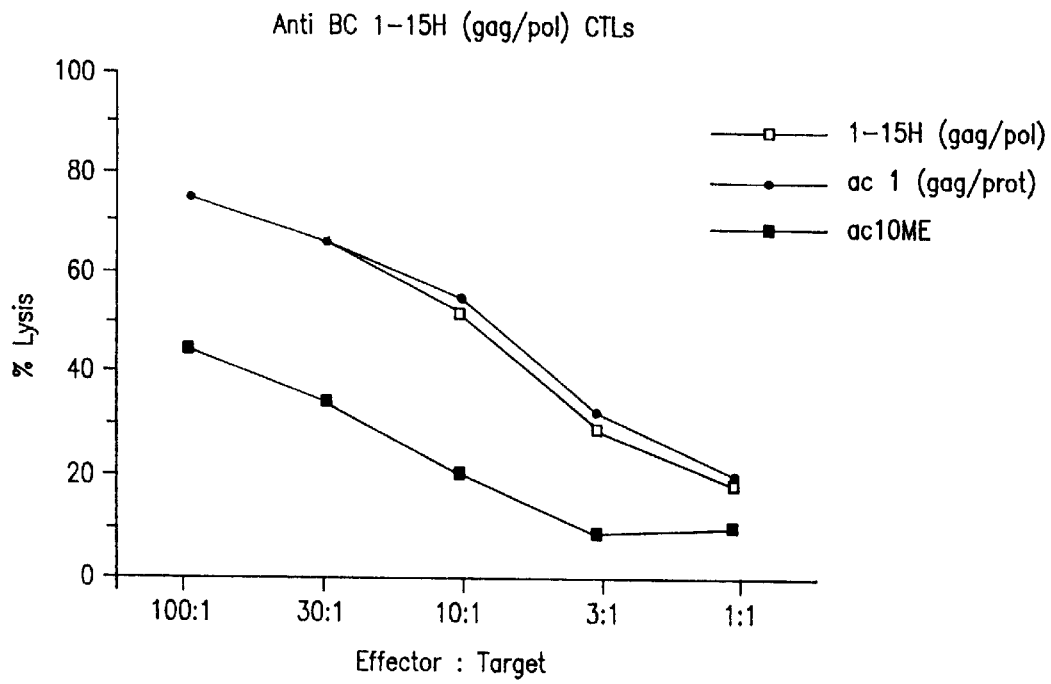
Figure 4M:
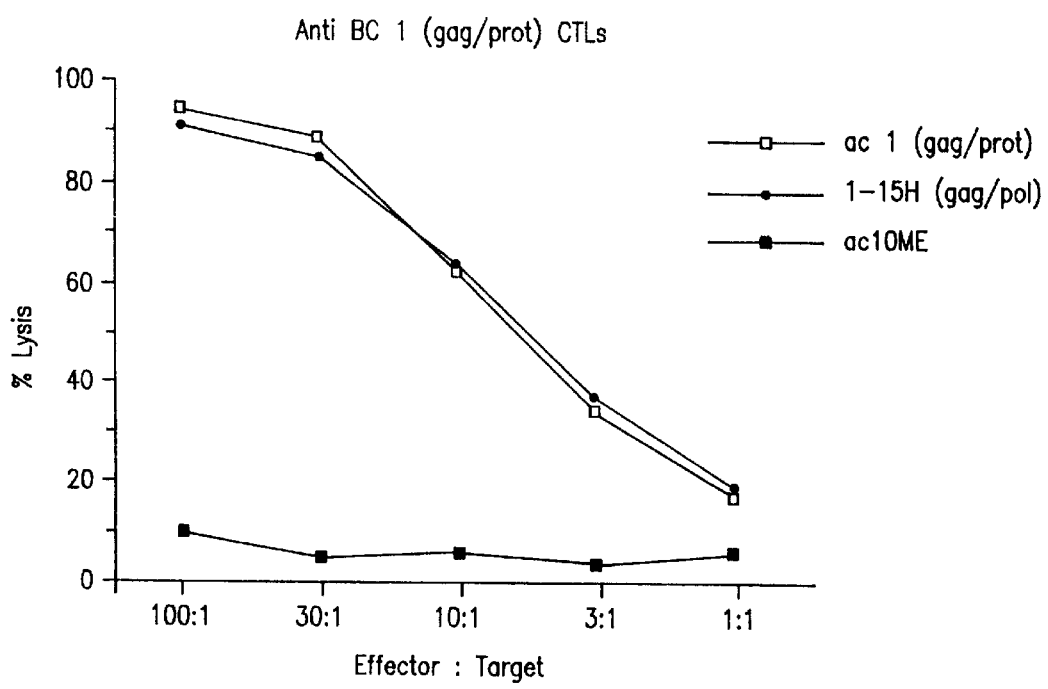

Further experiments were conducted to evaluate the specificity of the CTL killing induced by gag/pol and gag/prot stimulator cells. The results presented in FIGS. 4L and 4M illustrate that CTL induced by gag/pol or gag/prot stimulator cells killed both gag/pal (i.e., 1–15H) and gag/prot (i.e., BC-1) target cells. In this case, the killing by CTL may be directed towards shared regions common to both gag/pol and gag/prot.

Implementation of this immunostimulant application in humans requires that (1) the gene coding for the antigen of interest be delivered to cells, (2) the antigen be expressed in appropriate cells, and (3) MHC restriction requirements, i.e., class I and class II antigen interaction, are satisfied. Within a preferred embodiment, preparations of vector are made by growing the producer cells in normal medium, washing the cells with PBS plus human serum albumin (HSA) at 10 mg/ml, then growing the cells for 8–16 hours in PBS plus HSA. Titres obtained are typically $10^4$ to $10^6$/ml depending on the vector, packaging line or particular producer line clone. The vector supernatants are filtered to remove cells and are concentrated up to 100-fold by filtration through 100,000 or 300,000 pass Amicon filters (Wolff et al., *Proc. Natl. Acad. Sci.* 84:3344, 1987) or other equivalent filters. This lets globular proteins of 100,000 or 300,000 pass but retains 99% of the viral vector as infectious particles. The stocks can be frozen for storage since they lose about 50% of the infectious units on freezing and thawing. Alternatively, the viral vector can be further purified by conventional techniques. The most direct delivery involves administration of the appropriate gene-carrying vector into the individual and reliance upon the ability of the vector to efficiently target to the appropriate cells, which can then initiate stimulation of the immune response. The dose is generally $10^5$ to $10^6$ infectious units/kg body weight. The following example demonstrates the ability of direct vector injection to stimulate an immune response in mice.

Figure 4N:
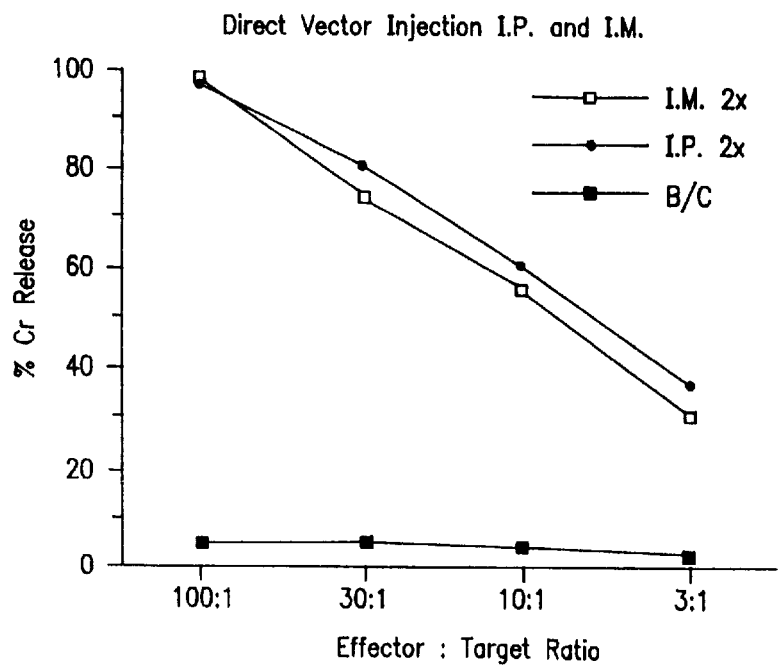

B. Stimulation Of An Immune Response In Mice By Direct Injection Of Retroviral Vector Experiments were performed to evaluate the ability of recombinant retroviral vectors to induce expression of HIV envelope proteins following direct injection in mice. Approximately $10^4$ to $10^5$ colony forming units (cfu) of recombinant retrovirus carrying the KT-1 vector construct were injected twice (2x) at 3-week intervals either by the intraperitoneal (I.P.) or intramuscular (I.M.) route. This amount of retrovirus was determined to be equivalent to approximately less than 100 $\mu$g of protein, which is usually considered too little to stimulate an immune response. Spleen calls were prepared for CTL approximately 7 to 14 days after the second injection of vector and CTL were restimulated in vitro using irradiated BCenV stimulator cells as described above (see Example 2A). The results presented in FIG. 4N illustrate that direct vector injection by the I.P. and I.M. routes stimulates the development of CTL which kill Bcenv target cells (I.M. 2x; I.P. 2x) but not control B/C cells (B/C). Thus, the injection of $10^4$ to $10^5$ units of retrovirus (an amount of protein antigen which would not usually stimulate an immune response) may induce expression of significant levels of HIV envelope in the autologous host cells which thereby leads to the induction of a specific CTL immune response.

However, a more practical approach may involve the extracorporeal treatment of patient peripheral blood lymphocytes (PBL), fibroblasts or other cells obtained from each individual with the vector, producer cells, or vector plasmid DNA. PBL can be maintained in culture through the use of mitogens (phytohemagglutinin) or lymphokines (e.g., IL-2). The following example demonstrates the ability of extracorporeal treatment of primate cells to induce expression of vector encoded proteins.

C. Extracorporeal Treatment Of Human, Chimpanzee And Macaque Cells To Induce Expression Of Vector Encoded Proteins Experiments were conducted in which human peripheral blood leukocytes (PBL) or fibroblasts and chimpanzee dermal fibroblasts were infected with a murine retroviral vector construct in which the cytomegalovirus (cmv) promoter drives expression of β-galactosidase (cmvβ-gal) as a marker enzyme for retroviral gene expression. (A more detailed discussion of the use of such "Expression Markers" appears in Section V, below; and engineering retroviral vector constructs carrying the β-gal marker is detailed also in Example 7, below). Infection was accomplished either by (a) electroporation (250V) or transfection ($CaPO_4$/polybrene) of recombinant retrovirus vector plasmid DNA, or (b) viral infection of cells by recombinant retrovirus carrying vector construct RNA by using the method of co-cultivating the cells with irradiated retroviral vector producer cells, or (c) by direct infection of cells by retroviral vector particles.

A preferred method of direct infection of primary chimp fibroblasts by retroviral vector particles is described below.

The chimp dermal fibroblasts were grown out from a 5 mm skin punch biopsy removed from the chimp while under anesthesia. The skin punch was transported in RPMI/10% Fetal Bovine Serum at ambient temperature. The punch was incubated in 0.5% trypsin/0.02% EDTA solution for 30 minutes at 37° C. and then cut into eight to twelve small chunks which were transferred to a 6 cm Tissue Culture Grade dish. After the tissue fragments were allowed to adhere to the plate, 1 ml of DMEM/20% FBS was added followed by 1 ml of media each subsequent day for 5 days. Fresh media was added every 5 days from then on until the fibroblasts covered approximately 50% of the dish or the fibroblasts around the individual chunks were crowding each other. The fibroblasts were removed using trypsin/EDTA and scraping, and transferred to a 10 cm dish. Once the 10 cm dish was confluent, cells were split 1:5 on a regular basis. The cells were then infected by adding 1 ml of retroviral vector, KT-1 or β-gal vector, from the CA line, containing supernatant in the presence of polybrene (2 $\mu$g/ml). Once the cells were confluent, the plate was split 1:3 to be either grown under selection or to be stained for β-gal expression. Selection was carried out in the presence of the cytocidal antibiotic, G418. Vector transduced cells are evaluated for gene expression (HIVenv) approximately 7 days following vector infection by Western blot. HIV env expression can be readily detected at levels known to elicit T cell responses in mice. The procedure is also applicable to human and macaque primary cells.

The results presented in Table I illustrate the infection of human and primate cells by recombinant β-gal retroviral vector constructs. The results illustrate expression of the β-galactosidase marker enzyme which can be visualized by histochemical staining method, i.e., resulting in the development of cells which carry a blue color (blue cells).

TABLE I

EXTRA CORPOREAL INFECTION OF PRIMATE CELLS WITH RETROVIRAL VECTOR CONSTRUCTS

| CELLS | INFECTION/ CONDITION | VECTOR CONSTRUCT (AMOUNT) | RE- SULTS* |
|---|---|---|---|
| Human PBL | | | |
| PBL | | | |
| PBL | Electroporate/250V | cmvβgal(90 $\mu$g) | +, − |
| PBL + PHA | ELectroporate/250V | cmvβgal(90 $\mu$g) | ++, + |
| | | cmvβgal(20 $\mu$g) | +/− |
| PBL + PHA + IL2 | Electroporate/250V | cmvβgal(90 $\mu$G) | +, + |
| | | cmvβgal(50 $\mu$g) | +, +/− |

TABLE I-continued

EXTRA CORPOREAL INFECTION OF PRIMATE CELLS
WITH RETROVIRAL VECTOR CONSTRUCTS

| CELLS | INFECTION/ CONDITION | VECTOR CONSTRUCT (AMOUNT) | RE-SULTS* |
|---|---|---|---|
| PBL#1 + PLB#2 (MLR) | Electroporate/250V | cmvβgal(90 μg) | ++, +/− |
| PBL#1 + PLB#2 (MLR) Human Fibroblast | Co-cultivation with Irradiated Producer | MLV/Neoβgal ($10^2$–$10^4$ pfu/ml) | ++, +++ |
| AF-2 | CaPO$_4$/polybrene Retroviral infection | cmvβgal(10 μg) MLVβgal ($10^3$ pfu) | 20–40% +++ |
| Vandenberg | CaPO$_4$/polybrene Retroviral infection | cmvβgal(10 μg) MLVβgal ($10^3$ pfu) | 10–15% +++ |
| Detroit 551 Chimpanzee Fibroblast | CaPO$_4$/polybrene Retroviral infection | cmvβgal(10 μg) MLVβgal ($10^3$ pfu) | 5% +++ |
| X80 | Retroviral infection | MLVβgal | ++ |

*Results of two experiments (separated by ", "); a +/− indicates 20–99 blue cells; a + indicated 100–499 blue cells; a ++ indicates 500–1499 blue cells; +++ indicates greater than 1500 blue cells, out of a total of 2–3 × $10^6$ total cells in the assay; % indicates that 5 to 40 percent of cells in the assay were infected as judged by the presence of blue cells after staining.

This type of approach allows for infection, monitoring of expression and expansion of the antigen presenting cell population prior to injection, and return of vector-expressing cells to the respective patient. Other types of cells can also be explanted, vector introduced, and the cells returned to the patient. Only a moderate number of infected cells ($10^5$–$10^7$) is necessary to elicit strong immune responses in mice. It is probable that the dose to elicit an immune response is roughly the same per individual animal or patient with very little dependence on body size.

Within one alternative method, cells are infected ex vivo as described above, and either inactivated by irradiation (see FIG. 4E) or killed by fixation, such as by formalin. Formalin fixation of cells treated with a vector expressing HIV env after treatment with the vector carrying the HIV env gene induces a strong CTL response.

Within another alternative method, stimulator cell membrane fragments which contain both the antigen of interest and the appropriate MHC molecule as a complex are employed. Cells are infected with vector, genes expressed, cells disrupted and the membranes purified by centrifugation or affinity columns specific for the MHC-antigen complex. This process provides greater quality control from a manufacturing and stability standpoint.

Within yet another alternative method, an immune response is stimulated in tissue culture, instead of in the patient, and the immune cells are returned to the patient. The following example demonstrates the ability of this type of approach to induce immune CTL in tissue culture.

D. In Vitro Induction Of Immune Response To Retroviral Vector-encoded Antigens Experiments were conducted to evaluate the ability of retroviral vector encoded antigens to induce an in vitro immune response in human peripheral blood leukocytes. PBL were prepared from donor #99 blood by leukopheresis and Ficoll-Hypaque density gradient sedimentation, and were stored frozen until use in liquid nitrogen in RPMI medium containing 20% FBS and 10% dimethylsulfoxide. To prepare EBV-transformed cell lines, freshly thawed PBL from donor #99 were depleted of T lymphocytes using OKT3 antibody and complement (or cyclosporin treatment), and 1 ml of EBV-containing culture supernatant from the B95 EBV-transformed lymphoblastoid cell line was added for each 5×$10^6$ T-depleted PBL in a total volume of 5 ml RPMI medium containing 2% human A-minus serum. The EBV-infected cells were distributed into 96 well round bottom tissue culture microtitre plates (200 μl per well) and placed in tissue culture at 37° C. in 95% air/5% CO$_2$ until visible cell pellets were observed in the bottom of the wells, after which time, the cells were removed from the wells, expanded in tissue culture dishes and flasks and periodically passaged. To prepare EBV-HIVenv stimulator cells for in vitro immunization, $10^7$ EBV-transformed PBL were treated in 10 ml RPMI medium with $10^4$ cfu/ml of tissue culture supernatant (or purified virus) from a producer cell line productively-infected with the KT-1 HIVenv retroviral vector. This vector also contains the neomycin drug resistance gene which confers resistance to G418 (a neomycin analogue). After overnight incubation at 37° C. in tissue culture the infected EBV-transformed cells were collected by centrifugation and resuspended in 1 ml of RPMI medium containing 10% FBS. EBV-transformed HIVenv expressing cells were selected for neomycin-resistance by adding 600 μg/ml of G418 to the medium and distributing 100 μl into each well of a 96 well round bottom microtitre plate. The plates were placed in tissue culture at 37° C. until visible cell pellets were observed, at which time, the cells were removed, expanded, and periodically passaged in tissue culture. HIVenv expression was verified by Western blot analysis using monoclonal or goat antibodies to HIV envelope proteins to identify gp160 and gp120 on nitrocellulose blots of SDS-PAGE gels. Alternatively, HIVenv expression was verified by assaying for the ability of EBV-transformed HIVenv-expressing cells to induce SupT1 cells to form multicellular syncytia, i.e., a property of SupT1 cells induced by some HIV envelope proteins. Finally, the donor #99 EBV-transformed HIV-env-expressing lymphoblastoid stimulator cells were irradiated at 10,000 R to inhibit cell replication. To prepare in vitro immunized human effector PBL, $10^7$ freshly-thawed donor #99 cells were mixed with $10^6$ EBV-transformed HIV env-expressing stimulator cells in RPMI 1640 containing 5% heat inactivated A-minus human serum with pyruvate and non-essential amino acids and the cell mixture was incubated at 37° C. for 7 days in tissue culture at a final density of 1–5×$10^6$ cells per ml. After 7 days, the in vitro-immunized effector cells were restimulated (in the same manner as described above), for an additional 5 to 7 days using a second addition of irradiated stimulator cells. To prepare target cells for the CTL assays, irradiated EBV-transformed HIV env stimulator cells were incubated for 1 hour with $^{51}$Cr, as described previously in Example 2A. The $^{51}$Cr release killing assay was also performed as described previously (Example 2A, above) but using donor #99 effector and target cells.

Figure 4O:
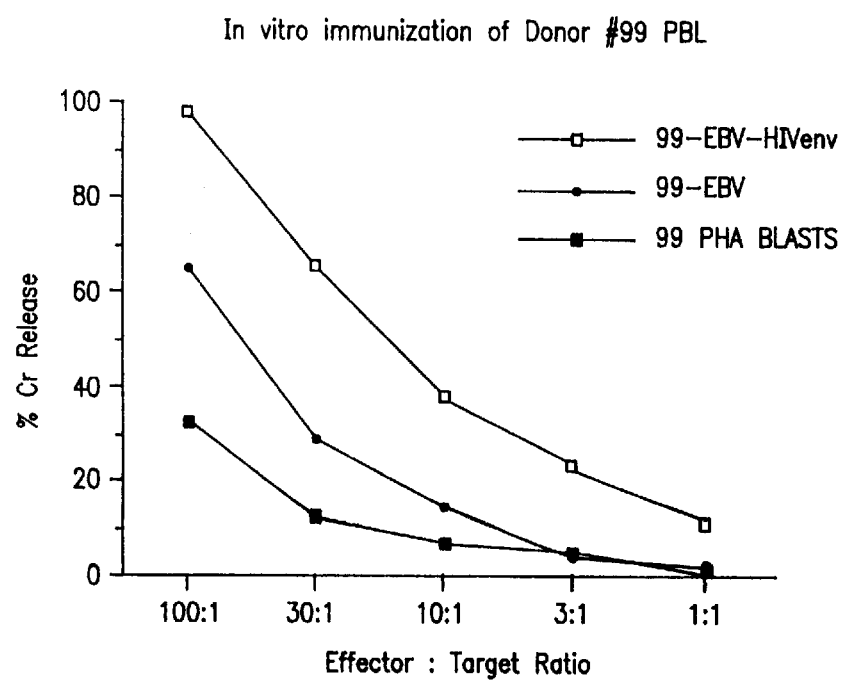

The results presented in FIG. 4O illustrate in vitro immunization of human donor #99 PBL to kill autologus EBV-transformed lymphoblastoid target cells expressing HIV envelope proteins (99-EBV-HIVenv) encoded by the KT1 retroviral vector. The results also show killing of autologous EBV-transformed cells (99-EBV) resulting from a natural immunity to EBV (i.e., prior EBV exposure as evidenced by the presence of antibody to EBV in the serum from donor #99). In vitro immunized donor #99 effector cells also showed a low level of killing of normal autologous PHA-stimulated lymphocytes (PHA blasts) at the 100:1 effector to target cell ratio, perhaps attributable to reactivation of latent EBV in these cells during in vitro culture.

This approach also allows the use of cells that do not express human MHC molecules or express decreased levels of MHC (e.g., human cell mutants, tumor cells, mouse cells). Individual MHC class I or class II genes are infected into MHC-cells to give expression of the individual corresponding MHC protein, in a particular cell line. The following example demonstrates the ability of this type of approach to induce expression of MHC proteins in a particular cell line which are functionally-active in presenting antigen to immune CTL.

E. Infection of Cells with both MHC and Antigen

Recombinant infectious retrovirus carrying murine H-2 genes are reported to induce expression and presentation of H-2 antigens so that cells infected with the retrovirus serve as target cells for lysis by allogeneic immune murine CTL (Weis, J. H. et al., *Molec. Cell Biol.* 5:1379–1384, 1985). In this case the H-2 antigen and its peptidic antigenic fragments are synthesized by the target cell and become associated with homologous "self" MHC molecules that are the natural biosynthetic product of the target cell.

Figure 4P:
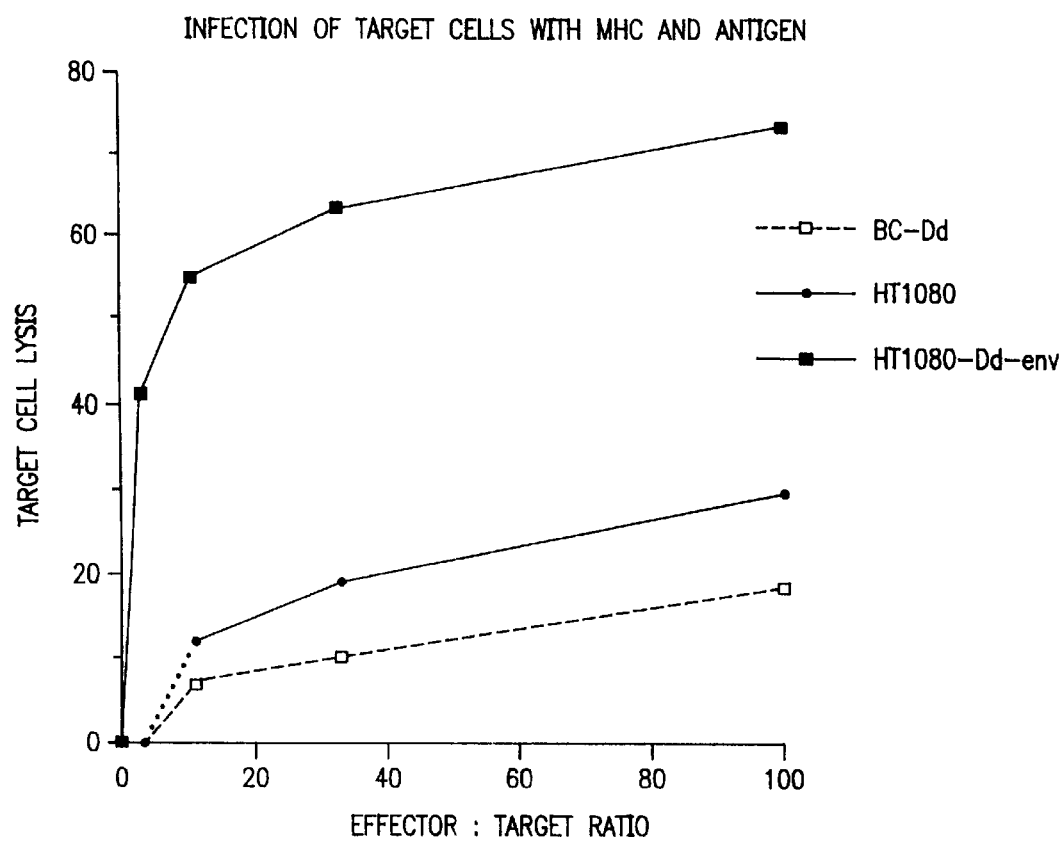
Figures 1, 4Q:
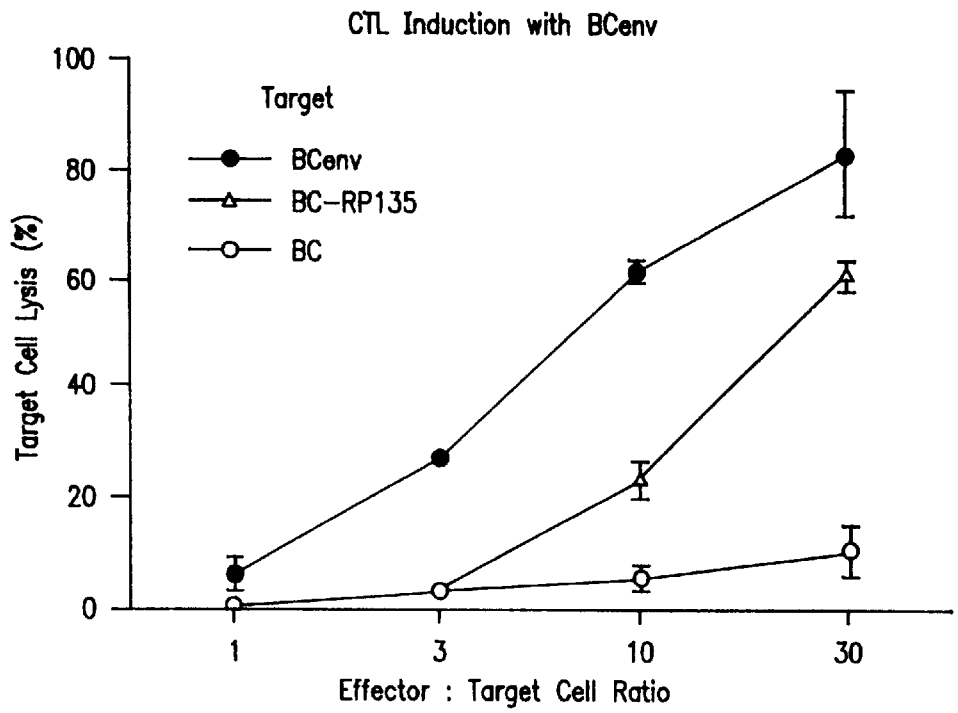
Figures 2, 4Q:
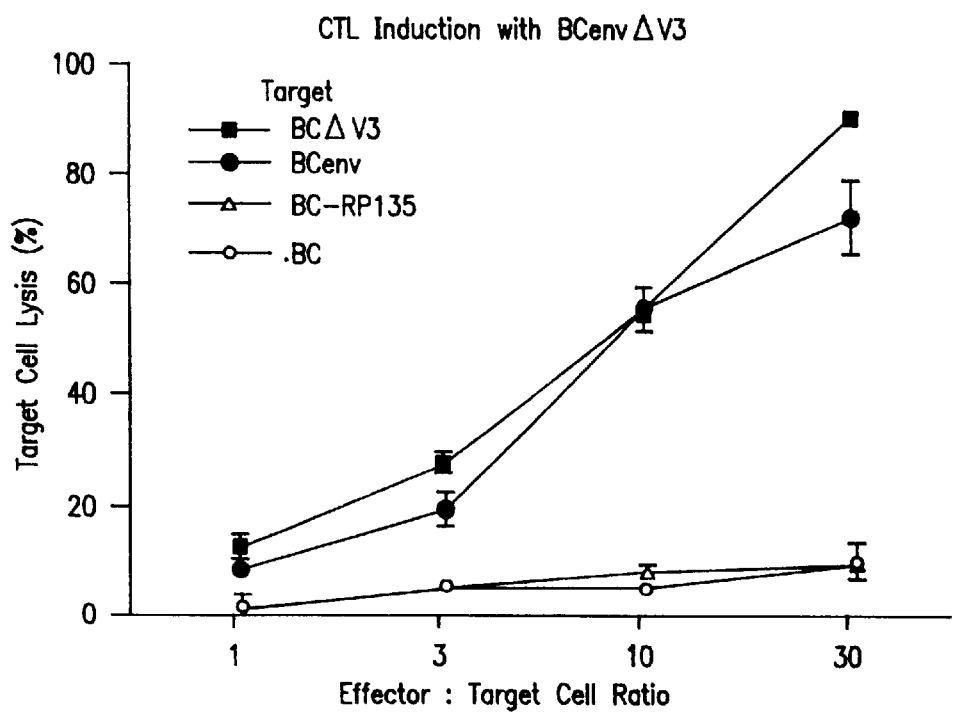
Figures 1, 4R:
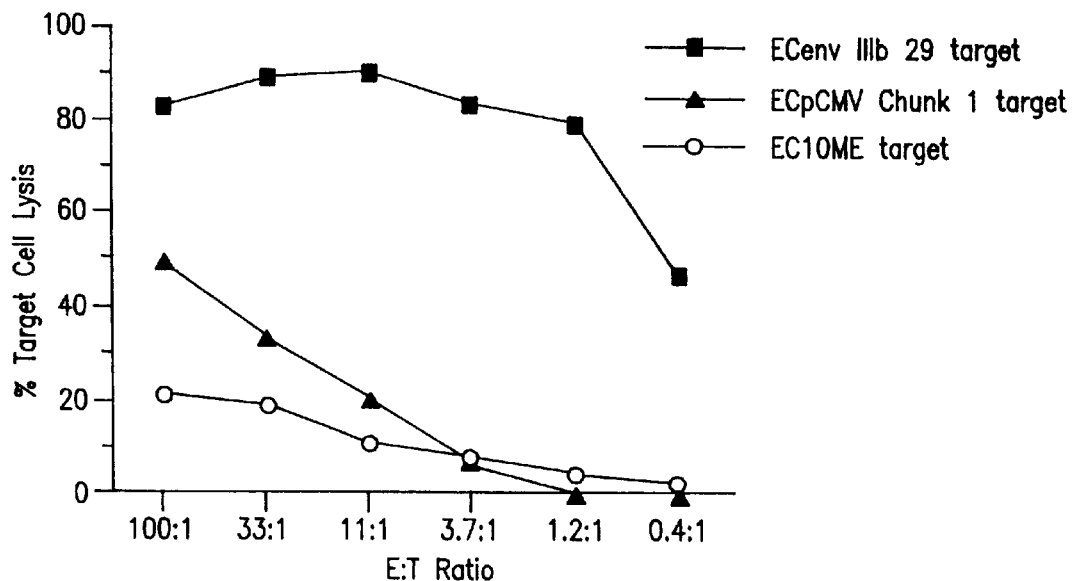
Figures 2, 4R:
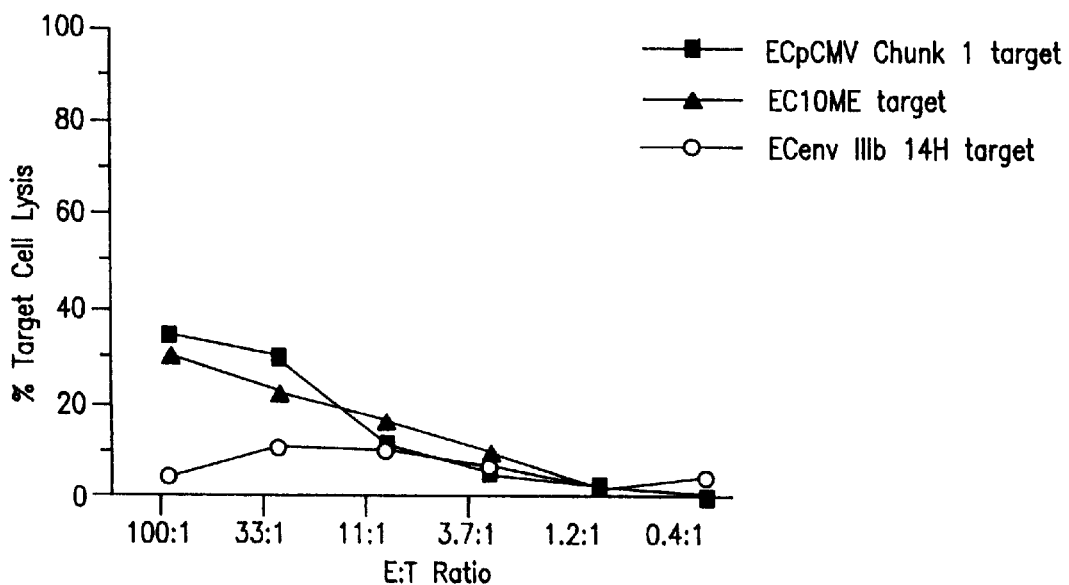
Figure 4S:
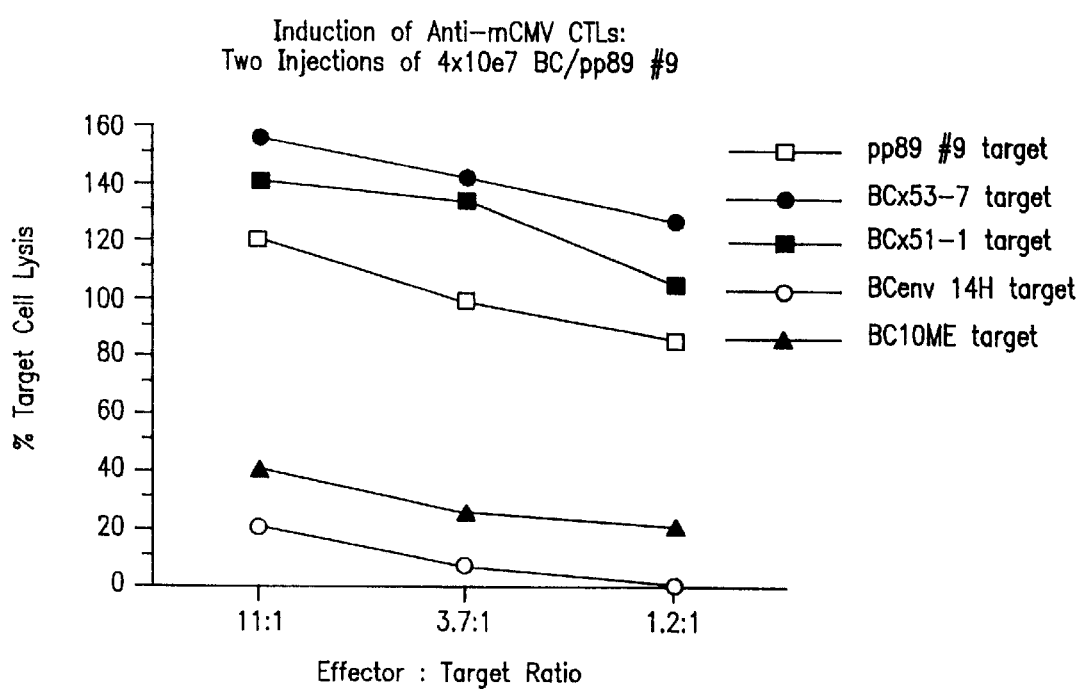

It was reasoned that it may be possible to have antigens presented by MHC molecules that are not the natural biosynthetic product of the cell when (a) the MHC gene is introduced into cells in a manner that permits proper expression of the gene and synthesis, folding, and processing of its protein product so that it is functionally active in the cell, and (b) the antigen gene is also introduced in a manner that would allow gene expression with synthesis of the antigen protein and appropriate association of its peptide antigenic fragments with the MHC molecules. To evaluate infection of cells with both antigen and MHC genes, and simultaneous expression of both gene products, experiments were conducted using murine H2-Dd as the MHC gene, HIVenv as the antigen, human HT1080 cells as the target cells, and murine HIVenv immune CTL as the effector cells. In this case the human cell must properly express the murine H2-Dd protein and the HIV envelope protein; the HIVenv peptide antigen fragment must become associated with functional murine H2-Dd proteins; and, finally the H2-Dd peptidic HIVenv-H2-Dd complex in the human call must properly present the antigen in the complex to HIVenv-immune murine CTL for the human target cell to be killed. The results presented in FIG. 4P illustrate that HT1080 cells transfected with murine H2-Dd and subsequently infected with retroviral vector carrying the KT-1 HIVenv vector construct (HT1080+Dd+env) present antigen and are killed by CTL that were induced in mice by immunization with murine BC10 env-29 cells, as described above (see Example 2A). These HIVenv-immune CTL kill in an antigen-specific manner, i.e., there was no lysis of control HT1080 cells or BC cells expressing only H-2Dd (BC-Dd) and not HIVenv.

In a similar manner, tumor cells may be infected with an MHC gene and a tumor antigen in order to promote either the induction of immune CTL or the killing of the tumor cells by immune CTL. In this manner autologous (i.e., from the patient), allogeneic (i.e., from another human donor), or xenogeneic (i.e., from an animal) CTL may be used to promote killing of human tumor cells by infecting the tumor cell with both an appropriate MHC molecule and a tumor antigen.

A bank of cell lines capable of displaying antigens in the context of different MHC classes may also be generated by infecting cells with an MHC gene (or fragment thereof) or with both an MHC gene and an antigen gene (or fragment thereof). A small number of these (10–20) will cover (i.e., have a match with) the majority of the human population. For example, HLA A2 is present in about 30–60% of individuals. In the case of non-human cells, those can be derived from transgenic animals (such as mice) which express human MHC molecules generally or in specific tissues due to the presence of a transgene in the strain of animals (see, e.g., Chamberlin et al., *Proc. Natl. Acad. Sci. USA* 85:7690–7694, 1988). These cell lines may be useful for mapping the peptidic antigenic fragments in tumor cell antigens or infectious agents which represent the major immunodominant epitopes of the protein for CTL or antibody induction.

In any of the above situations, the presentation or response to the presentation can be enhanced by also infecting into the cells genes of other proteins involved in the immune interactions which are missing or underrepresented (e.g., $\beta$ microglobulin, LFA3, CD3, ICAM-I and others). $\beta$ microglobulin is a nonvariant, necessary subunit of the class I MHC, CD3 is involved in the MHC interaction, and LFA3 and ICAM-I molecules enhance the interaction of cells of the immune system (see, e.g., Altmann et al., *Nature* 338:512, 1989) leading to stronger responses to the same level of immune stimulation.

In the case of transgenic mice expressing human MHC, the stimulation could also be performed in the mouse using somatic transgenic mouse cells expressing a foreign antigen, the gene for which was introduced by a viral vector or other means, as stimulators. The mouse CTL thus generated would have T-cell receptors expressing in the context of the human MHC, and could be used for passive cellular immunization or treatment (i.e., infused into patients) of patients.

As a further alternative, one can use cells from a patient and boost expression of "self" MHC class I genes by introducing the matched MHC gene by vector transfer or other means including the use of genes encoding proteins (e.g., interferons) which stimulate MHC expression or the use of regulatory elements which control expression of MHC gene expression. Such a boost in MHC I expression causes more efficient presentation of foreign antigens, whether they are present already in the patient's cells (e.g., tumor cells) or subsequently added using viral vectors encoding foreign antigens. This, in turn, leads to a more potent immune response when even cells with reduced MHC I expression (such as some virally infected cells or some tumor types) are efficiently eliminated. Within certain aspects of the present invention, one can infect susceptible target cells with a combination or permutation of nucleic acid sequences encoding (a) individual Class I or Class II MHC protein, or combinations thereof; (b) specific antigens or modified forms thereof capable of stimulating an immune response; (c) both MHC and antigen(s); and (d) other proteins involved in the immune interactions which are missing or underrepresented, as discussed above. The respective steps of infection may be performed in vivo or ex vivo. The immune CTL induction may be performed either ex vivo or in vivo and the killing of the specific cell types may be effected ex vivo or in vivo.

A different form of administration is the implantation of producer lines making retroviral vector particles. These may be immunologically unmatched classical producer cell lines or the patients own cells, which have been explanted, treated and returned (see VI Alternative Viral Vector Packaging Techniques, below). Both types of implants ($10^5$–$10^6$ cells/kg body weight) would have a limited life span in the patient, but would lead to the retroviral vector infecting large numbers ($10^7$–$10^{10}$) of cells in their vicinity in the body.

In any case, the success of the HIV immune stimulating treatment can be assayed by removing a small amount of blood and measuring the CTL response using as targets the individual's own cells infected with vector leading to env expression.

When it is desired to stimulate an MHC class I or class II restricted immune response to pathogens, including pathogenic viruses other than HIV, suitable forms of envelope or other antigens associated with such retroviruses which will stimulate an immune response can be ascertained by those skilled in the art. In general, there will be combinations of epitopes which cause induction of various parts of the immune system (e.g., $T_H$-, $T_C$-, B-cells). In addition, some epitopes may be pathogenic or hypervariable but immunodominant. The present invention allows a "mix-and-match" selection of combinations of desirable epitopes and exclusion of undesirable epitopes. For example, in HIV, a number of hypervariable loops which carry immunodominant B- and T-cell epitopes can be strung together in the gene sequence carried by the vector so that the resultant immunostimulation is appropriate for the preponderance of HIV strains found clinically. The following example illustrates procedures using retroviral vectors for identifying and mapping CTL-modified forms thereof.

F. Vectors Ex-pressing HIV Antigenic Eitopes and Modified Forms Thereof for Mapping the Immune Response The results presented above in Example 2 (above) illustrate that mice immunized with retroviral vector-encoded HIVenv develop significant class I MHC-restricted CTL responses that are specific for HIVenv. Further, the results presented in Example 2 illustrate that HIVenvIIIB induced CTL which exhibit lytic activity on target cells coated with synthetic peptides derived from the gp120 hypervariable region of both HIV-IIIB and HIV-MN variants. To further map the regions within the HIV envelope gene encoding peptidic antigen fragments reactive in inducing and stimulating CTL, and in mediating lysis of targets by immune CTL, experiments were conducted with the "Δloop" and "Chunk I" recombinant retroviral vector constructs described in Example 1F, above, The "Δloop" vector is an HIV-IIIB env-encoding vector construct which has a deletion of the gp120 hypervariable loop in the V3 domain of the envelope gene so that a truncated protein may be produced containing only the non-loop ("loopless") portions of HIVenv.

To map peptidic antigenic epitopes within the HIV envelope protein reactive with CTL, experiments were conducted in which retrovirus carrying the "Δloop" vector construct was used to infect BC cells and thereby create cells expressing envelope proteins having the truncated form of "loopless" envelope, i.e., lacking the gp120 hypervariable loop (BCenvΔV3 cells). These "loopless" HIVenv cells were tested for their ability to induce HIVenv-immune CTL in mice. The results presented in FIG. 4A include control assays, in panel A, and experimental assays in panel B. The results illustrate that CTL are induced in mice by "loopless" BCenvΔV3 cells and these CTL kill both BCenvΔV3 cells (panel 1B, FIG. 4Q) and BCenvΔV3 target cells expressing a full-length envelope protein. Specificity of the CTL was illustrated by their failure to lyse BC cells (i.e., not expressing HIVenv) or BC cells coated with the RP135 synthetic "loop"peptide (BC-RP135), i.e., lacking in the BCenvΔV3 cells used to induce the CTL. The results of control assays presented in FIG. 4Q, panel A, illustrate that BC cells coated with RP135 peptide (BC-RP135) effectively-presented antigen to BCenv-"loop"-immune CTL (i.e., BCenv-immune CTL) and were killed by these effector cells in a specific manner, i.e., the BCenv-immune CTL did not kill BC cells (the negative control) but did kill BCenv target cells (the positive control). Thus, retrovirus-carrying recombinant vector constructs can be used to identify and map regions of the HIV envelope protein that induce CTL and confer lysability upon target cells.

To further map the peptidic antigenic regions within the HIV envelope, experiments were conducted in which the "Chunk 1" vector construct was used to infect BC cells and thereby create cells expressing a "loopless" envelope protein which also lacks peptide sequences in regions adjacent to the gp120 loop. The results presented in panel A of FIG. 4R illustrate that target cells expressing "Chunk 1" (i.e., BCpCMV Chunk1 target) are lysed in a specific manner by HIVenv-immune CTL, i.e., these CTL do not lyse BC10ME cells (the negative control) but do lyse BC cells expressing HIVenv (BCenvIIIB target). The results presented in panel B of FIG. 4R also illustrate that BCpCMV Chunk 1 target cells and BC cells expressing HIVenv (BCenv IIIB 14H target) are lysed but not BC10ME cells (BE10ME target).

G. Cells treated with vectors expressing MCMV antigenic epitope can elicit CTL responses and act as targets to measure these responses.

Antigens other than those from HIV will also elicit responses in mice stimulated with syngeneic cells treated with vectors as described above. The plasmid 62/3 (FIG. 1C) encodes the pp89 immediate early gene of MCMV (Del Val et al., *J. Virol.* 62:3965, 1988) and will express the pp89 on infection by calcium phosphate precipitate into BC10ME cells. A clone (pp89 #9) was selected that permanently expressed the pp89 protein.

Retroviral vector genomes which express pp89 were constructed as follows. From plasmid 62/3, a 980 base pair PCR fragment from the Xba I site to a site beyond the termination codon and upstream of the ATAAA sequence was made. At the 3' end of this fragment is a novel Cla I site. A three part ligation was performed in which the RI-Xba I fragment containing the 5' half of the pp89 gene was joined to this PCR fragment at the Xba I and Cla I sites and inserted into the SK+ vector at the RI and Cla I sites. The reconstituted pp89 gene was then inserted into the KT-1 backbone. The pp89 fragment contained blunted RI (by Klenow fill-in) and normal Cla I termini. The KT-1 backbone had blunted Xho I (by Klenow fill-in) and normal Cla I termini. The $SV_2$neo cassette was then introduced into the Cla I site in both orientations, to give the vectors 53-7 and 51-1 (FIG. 1C).

Infectious helper recombinant retroviral vector was generated by transient transfection of the line 293 2-3 with the vector genome and the VSV G encoding plasmid as in Example 9C(iii). This was used to infect BC10ME cells which showed expression by immunof luorescence and Western blot analyses.

Balb/c mice were injected twice with $4 \times 10^7$ pp89 #9 cells and the spleen cells tested for effector activity against various targets: (a) itself; (b) BC cells infected with vectors 53-7 or 51-1; (c) BC env cells; and (d) parent BC10ME cells (FIG. 4S). Specific killing was observed only on the pp89 expressing cells and not on the parent line or the line expressing an irrelevant antigen (HIV env).

An alternative approach to creating a desired immune response is to deliver an antigen-specific T-cell receptor gene to an appropriate cell, such as a T-cell. It is also possible to molecularly graft the genetic message for antigen recognition sites of immunoglobulin molecules into the corresponding sites in the genes of the related T-cell receptor subunits α and β. Such altered protein molecules will not be MHC restricted, and will be able to perform as $T_H$- and $T_C$-cells specific for the antigen defined by the original immunoglobulin. Another tactic is to transfer genes for effector molecules in NK into NK cells to confer additional non-MHC limited killing capability on these cells. In addition, specific immunoglobulin genes could similarly be useful when delivered to B-cells to cause the large-scale in vivo production of a particular antibody molecule in a patient.

II. Blocking Agents

Many infectious diseases, cancers, autoimmune diseases, and other diseases involve the interaction of viral particles with cells, cells with cells, or cells with factors. In viral infections, viruses commonly enter cells via receptors on the surface of susceptible cells. In cancers, cells may respond inappropriately or not at all to signals from other cells or factors. In autoimmune disease, there is inappropriate recognition of "self" markers. Within the present invention, such interactions may be blocked by producing, in vivo, an analogue to ither of the partners in an interaction.

This blocking action may occur intracellularly, n the cell membrane, or extracellularly. The blocking action of a viral or, in particular, a retroviral vector carrying a gene for a blocking agent, can be mediated either from inside a susceptible cell or by secreting a version of the blocking protein to locally block the pathogenic interaction.

In the case of HIV, the two agents of interaction are the gp 120/gp 41 envelope protein and the CD4 receptor molecule. Thus, an appropriate blocker would be a vector construct expressing either an HIV env analogue that blocks HIV entry without causing pathogenic effects, or a CD4 receptor analogue. The CD4 analogue would be secreted and would function to protect neighboring cells, while the gp 120/gp 41 is secreted or produced only intracellularly so as to protect only the vector-containing cell. It may be advantageous to add human immunoglobulin heavy chains or other components to CD4 in order to enhance stability or complement lysis. Delivery of a retroviral vector encoding such a hybrid-soluble CD4 to a host results in a continuous supply of a stable hybrid molecule.

Figure 5:
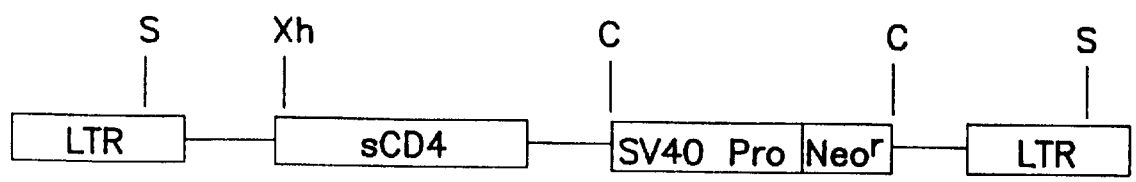
FIG. 5 depicts a vector designed to express sCD4.

Vector particles leading to expression of HIV env may also be constructed as described above. It will be evident to one skilled in the art which portions are capable of blocking virus adsorption without overt pathogenic side effects (Willey et al., *J. Virol.* 62:139, 1988; Fisher et al., *Science* 233:655, 1986). The following example describes the construction of a CD4 vector from which infectious vector particles were made (FIG. 5).

EXAMPLE 3 sCD4 Vector

1. A 1.7 kb Eco R1—Hind III DNA fragment from pMV7.T4 (Maddon et al., *Cell* 47:333, 1986) was bluntend ligated to the Hinc II site of Sk⁺.

2. A universal translation termination sequence containing an Xba I site was inserted into the Nhe I site of the CD4 fragment.

3. The 1.7 kb Xho I—Cla I fragment was excised and cloned into the Xho I—Cla I site of PAFVXM. These vector plasmids can be used to generate infectious vector particles, as described in Example 1.

Such infectious blocking vectors, when put into human T-cell lines in culture, can inhibit the spread of HIV infections. Preparation, concentration and storage of infectious retroviral vector preparations is as for the immunostimulant. Route of administration would also be the same, with doses about tenfold higher. Another route which may be used is the aspiration of bone marrow, infection with retroviral vector and return of this infected marrow (Gruber et al., *Science* 230:1057, 1985) to the patient. Since the marrow replication will amplify the vector expression through cell replication, doses in the range of the immunostimulant can be used ($10^5$–$10^6$/kg body weight).

In any case, the efficacy of the treatment can be assayed by measuring the usual indicators of disease progression, including antibody level, viral antigen production, infectious HIV levels, or levels of nonspecific infections.

III. Expression of Palliatives

Techniques similar to those described above can be used to produce recombinant retroviruses with vector constructs which direct the expression of an agent (or "palliative") which is capable of inhibiting a function of a pathogenic agent or gene. Within the present invention, "capable of inhibiting a function" means that the palliative either directly inhibits the function or indirectly does so, for example, by converting an agent present in the cells from one which would not normally inhibit a function of the pathogenic agent to one which does. Examples of such functions for viral diseases include adsorption, replication, gene expression, assembly, and exit of the virus from infected cells. Examples of such functions for a cancerous cell or cancer-promoting growth factor include viability, cell replication, altered susceptibility to external signals (e.g., contact inhibition), and lack of production or production of mutated forms of anti-oncogene proteins.

(i) Inhibitor Palliatives

In one aspect of the present invention, the recombinant retrovirus carries a vector construct which directs the expression of a gene which can interfere with a function of a pathogenic agent, for instance in viral or malignant diseases. Such expression may either be essentially continuous or in response to the presence in the cell of another agent associated either with the pathogenic condition or with a specific cell type (an "identifying agent"). In addition, vector delivery may be controlled by targeting vector entry specifically to the desired cell type (for instance, a virally infected or malignant cell) as discussed below.

A preferred method of administration is leukophoresis, in which about 20% of an individual's PBLs are removed at any one time and manipulated in vitro. Thus, approximately $2 \times 10^9$ cells may be treated and replaced. Since the current maximum titres are around $10^6$/ml, this requires 2 to 20 liters of starting viral supernatant. Repeat treatments also would be performed. Alternatively, bone marrow may be treated and allowed to amplify the effect as described above.

In addition, packaging cell lines producing a vector may be directly injected into a subject, allowing continuous production of recombinant virions. Examples of suitable cell types include monocytes, neutrophils, or their progenitors, since these cells are present in the peripheral blood but can also leave the circulatory system to allow virus production in extravascular tissue (particularly the central nervous system) where virion production may be therapeutically required. Such a cell line would ultimately be rejected as foreign by the host immune system. To ensure the eventual destruction of these foreign cells from the host (even an immunosuppressed host) the cell line may be engineered to express the gene for a conditionally lethal protein, such as HSVTK. Thus, administration of the drug Acyclovir (ACV) (a drug which is specifically toxic for cells expressing HSVTK) eliminates these cells after sufficient vector has been produced in vivo. Such a packaging cell line could be a continuous cell line or could be made directly from host cells.

Figure 10:
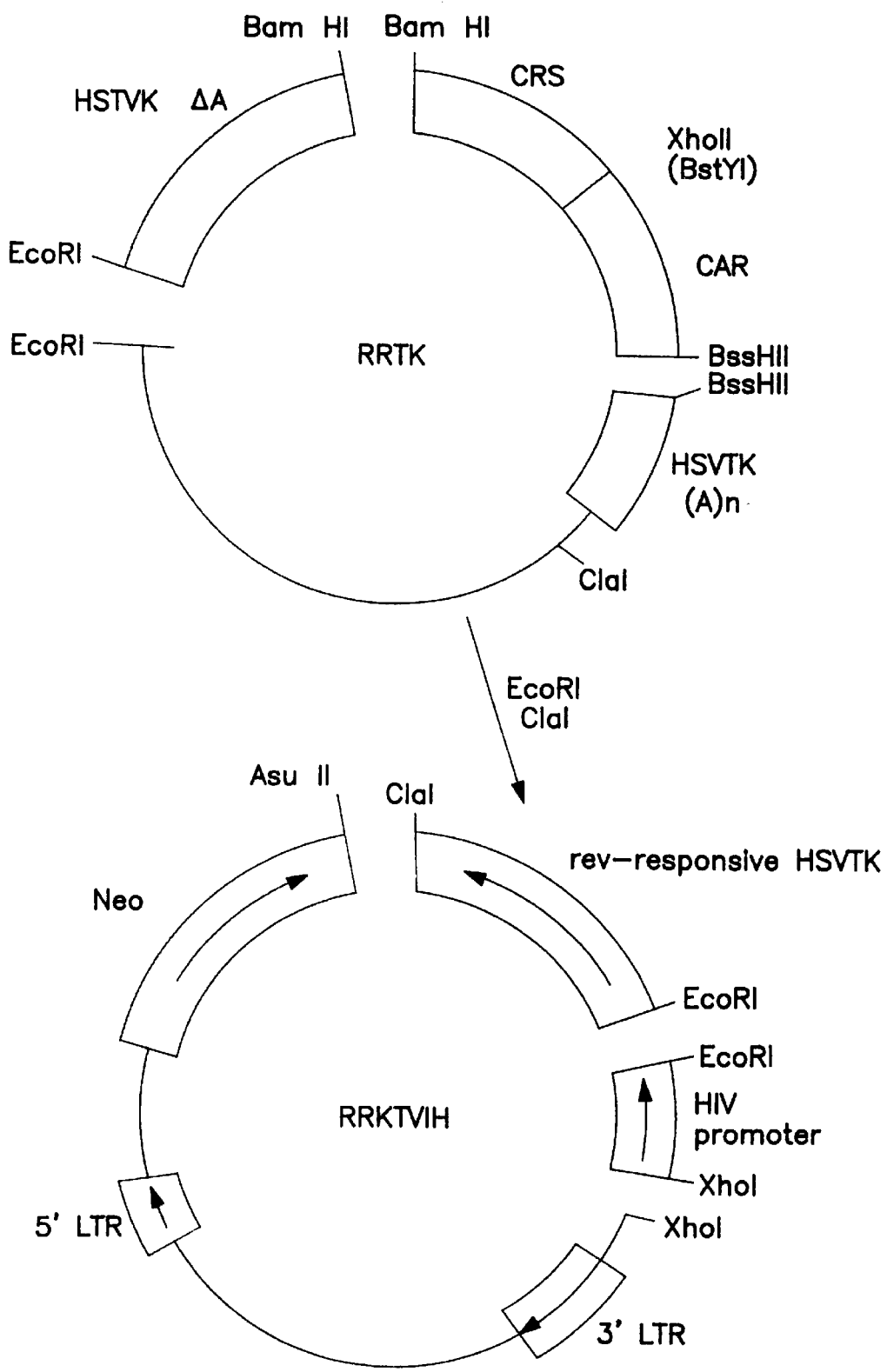
FIG. 10 illustrates the construction of the plasmid carrying the vector RRKTVIH.

In one embodiment, retroviral viruses which express RNA complementary to key pathogenic gene transcripts (for example, a viral gene product or an activated cellular oncogene) can be used to inhibit translation of that transcript into protein, such as the inhibition of translation of the HIV tat protein. Since expression of this protein is essential for viral replication, cells containing the vector would be resistant to HIV replication. To test this, the vector atat (FIG. 10) has been constructed, packaged as recombinant virions and introduced into human T-cells and monocyte cell lines in the absence of replication-competent helper virus.

In a second embodiment, where the pathogenic agent is a single-stranded virus having a packaging signal, RNA complementary to the viral packaging signal (e.g., an HIV packaging signal when the palliative is directed against HIV) is expressed, so that the association of these molecules with the viral packaging signal will, in the case of retroviruses, inhibit stem loop formation or tRNA primer binding required for proper encapsidation or replication of the retroviral RNA genome.

In a third embodiment, a retroviral vector may be introduced which expresses a palliative capable of selectively inhibiting the expression of a pathogenic gene, or a palliative capable of inhibiting the activity of a protein produced by the pathogenic agent. In the case of HIV, one example is a mutant tat protein which lacks the ability to transactivate expression from the HIV LTR and interferes (in a trans-dominant manner) with the normal functioning of tat protein. Such a mutant has been identified for HTLV II tat protein ("XII Leu$^5$" mutant; see Wachsman et al., *Science* 235:674, 1987). A mutant transrepressor tat should inhibit replication much as has been shown for an analogous mutant repressor in HSV-1 (Friedmann et al., *Nature* 335:452, 1988).

Such a transcriptional repressor protein may be selected for in tissue culture using any viral-specific transcriptional promoter whose expression is stimulated by a virus-specific transactivating protein (as described above). In the specific case of HIV, a cell line expressing HIV tat protein and the HSVTK gene driven by the HIV promoter will die in the presence of ACV. However, if a series of mutated tat genes are introduced to the system, a mutant with the appropriate properties (i.e., represses transcription from the HIV promoter in the presence of wild-type tat) will grow and be selected. The mutant gene can then be reisolated from these cells. A cell line containing multiple copies of the conditionally lethal vector/tat system may be used to assure that surviving cell clones are not caused by endogenous mutations in these genes. A battery of randomly mutacanized tap genes are then introduced into these cells using a "rescuable" retroviral vector (i.e., one that expresses the mutant tat protein and contains a bacterial origin of replication and drug resistance marker for growth and selection in bacteria). This allows a large number of random mutations to be evaluated and permits facile subsequent molecular cloning of the desired mutant cell line. This procedure may be used to identify and utilize mutations in a variety of viral transcriptional activator/viral promoter systems for potential antiviral therapies.

In a fourth embodiment, the recombinant retrovirus carries a vector construct that directs the expression of a gene product capable of activating an otherwise inactive precursor into an active inhibitor of the pathogenic agent. For example, the HSVTK gene product may be used to more effectively metabolize potentially antiviral nucleoside analogues, such as AZT or ddC. The HSVTK gene may be expressed under the control of a constitutive macrophage or T-cell-specific promoter and introduced into these cell types. AZT (and other nucleoside antivirals) must be metabolized by cellular mechanisms to the nucleotide triphosphate form in order to specifically inhibit retroviral reverse transcriptase and thus HIV replication (Furmam et al., *Proc. Natl. Acad. Sci. USA* 83:8333–8337, 1986). Constitutive expression of HSVTK (a nucleoside and nucleoside kinase with very broad substrate specificity) results in more effective metabolism of these drugs to their biologically active nuclestide triphosphate form. AZT or ddC therapy will thereby be more effective, allowing lower doses, less generalized toxicity, and higher potency against productive infection. Additional nucleoside analogues whose nucleotide triphosphate forms show selectivity for retroviral reverse transcriptase but, as a result of the substrate specificity of cellular nucleoside and nucleotide kinases are not phosphorylated, will be made more efficacious. A description of a representative method is set forth in Example 4.

EXAMPLE 4

Vectors Designed to Potentiate the Antiviral Effect of AZT and Analogues

A. All of the following retroviral vectors are based on the "N2" vector (see Keller et al., *Nature* 318:149–154, 1985). Consequently, 5' and 3' Eco R1LTR fragments (2.8 and 1.0 kb, respectively) were initially subcloned into plasmids containing polylinkers (into SK$^+$ to give pN2R5[+/−]; into pUC31 to give p31N2R5[+/−] and p31N2R3[+/−]) to facilitate vector construction. pUC31 is a modification of pUC19 carrying additional restriction sites (Xho I, Bgl II, BssH II, and Nco I) between the Eco R1 and Sac I sites of the polylinker. In one case, a 1.2 kb Cla I/Eco R1 5' LTR fragment was sabcloned into the same sites of an SK$^+$ vector to give pN2CR5. In another case, the 5' LTR containing a 6 bp deletion of the splice donor sequence was subcloned as a 1.8 kb Eco R1 fragment into pUC31 (p31N25delta[+]). The coding region and transcriptional termination signals of HSV-1 thymidine kinase gene were isolated as a 1.8 kb Bgl II/Pvu II fragment from plasmid 322TK (3.5 kb Bam HI fragment of HSVTK cloned into Bam HI of pBR322) and cloned into Bgl II/Sma I-digested pUC31 (pUCTK). For constructs which require deletion of the terminator signals, pUCTK was digested with Sma I and Bam HI. The remaining coding sequences and sticky-end Bam HI overhang were reconstituted with a double-stranded oligonucleotide made from the following oligomers:

5' GAG AGA TGG GGG AGG CTA ACT GAG 3'
and 5' GAT CCT CAG TTA GCC TCC CCC ATC TCT C 3' forming the construct pTK delta A.

For diagnostic purposes, the oligos were designed to destroy the Sma I site while keeping its Ava I site without changing the translated protein.

The 0.6 kb HIV promoter sequences were cloned as a Dra I/Hind III fragment from pCV-1 (see Arya et al., *Science* 229:69–73, 1985) into Hinc II/Hind III-cut SK$^+$ (SKE).

Figure 6:
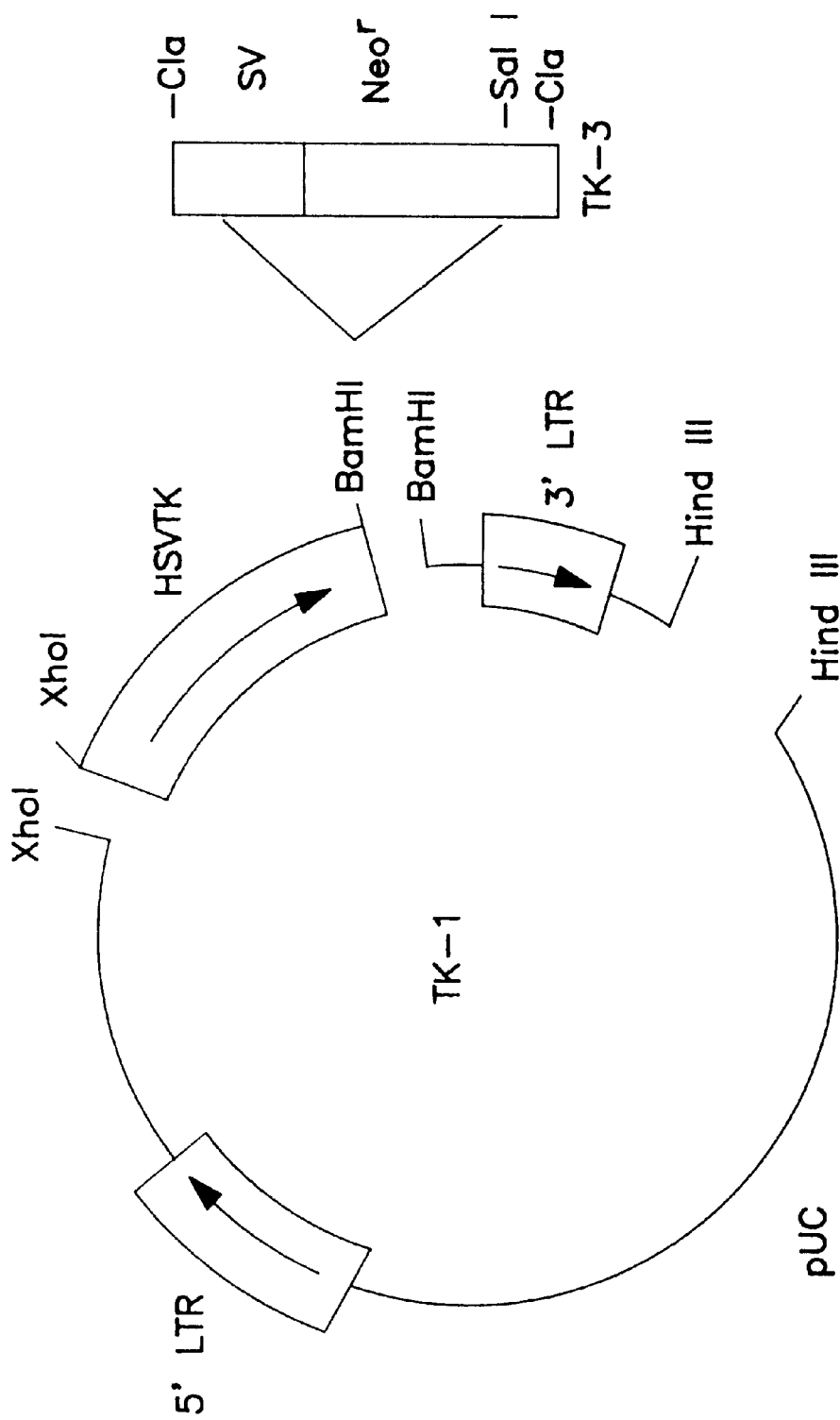
FIG. 6 illustrates the construction of the plasmids carrying the vectors TK1 (without SV-Neo) and TK3 (plus SV-Neo).

B. Construction of TK-1 and TK-3 retroviral vectors (see FIG. 6).

1. The 5 kb Xho I/Hind III 5' LTR and plasmid sequences were isolated from p31N2R5(+).

2. HSVTK coding sequences lacking transcriptional termination sequences were isolated as a 1.2 kb Xho I/Bam HI fragment from pTKdeltaA.

3. 3' LTR sequences were isolated as a 1.0 kb Ban HI/Hind III fragment from pN2R3(−).

4. The fragments from steps 1–3 were mixed, ligated, transformed into bacteria, and individual clones identified by restriction enzyme analysis (TX-1).

5. TX-3 was constructed by linearizing TY-1 with Bam HI, filling in the 5' overhang and blunt-end ligating a 5'-filled Cla I fragment containing the bacterial lac UV5 promoter, SV40 early promoter, plus Tn5 Neo$^r$ gene. Kanamycin-resistant clones were isolated and individual clones were screened for the proper orientation by restriction enzyme analysis.

These constructs were used to generate infectious recombinant vector particles in conjunction with a packaging cell line, such as PA317, as described above.

Administration of these retroviral vectors to human T-cell and macrophage/monocyte cell lines can increase their resistance to HIV in the presence of AZT and ddC compared to the same cells without retroviral vector treatment. Treatment with AZT would be at lower than normal levels to avoid toxic side effects, but still efficiently inhibit the spread of HIV. The course of treatment would be as described for the blocker.

Preparation, concentration and storage of the retroviral vector preparations would be as described above. Treatment would be as previously described but ex corpore treatment of patients' cells would aim for uninfected potentially susceptible T-cells or monocytes. One preferred method of targeting the susceptible cell is with vectors which carry HIV env or hybrid env (see Section VIII Cell Line Specific Retroviruses, below) to direct absorption of vector particles to CD4$^+$ cells. Normal adults have about $5 \times 10^9$ T4 calls in their total blood and about the same number of monocytes.

A fifth embodiment for producing inhibitor palliatives involves the delivery and expression of defective interfering viral structural proteins, which inhibit viral assembly. Vectors would code for defective gag, pol, env or other viral particle proteins or peptides, and these would inhibit in a dominant fashion the assembly of viral particles. This occurs because the interaction of normal subunits of the viral particle is disturbed by interaction with the defective subunits.

A sixth such embodiment involves the expression of inhibiting peptides or proteins specific for viral protease. Viral protease cleaves the viral gag and gag/pol proteins into a number of smaller peptides. Failure of this cleavage in all cases leads to complete inhibition of production of infectious retroviral particles. The HIV protease is known to be an aspartyl protease, and these are known to be inhibited by peptides made from amino acids from protein or analogues. Vectors to inhibit HIV will express one or multiple fused copies of such peptide inhibitors.

A seventh embodiment involves the delivery of suppressor genes which, when deleted, mutated or not expressed in a cell type, lead to tumorigenesis in that cell type. Reintroduction of the deleted gene by means of a viral vector leads to regression of the tumor phenotype in these cells. Examples of such cancers are retinoblastoma and Wilms Tumor. Since malignancy can be considered to be an inhibition of cellular terminal differentiation compared with cell growth, the retroviral delivery and expression of gene products which lead to differentiation of a tumor should also, in general, lead to regression.

In an eighth embodiment, the retroviral construct (with or without the expression of a palliative) provides a therapeutic effect by inserting itself into a virus, oncogene, or pathogenic gene, thereby inhibiting a function required for pathogenesis. This embodiment requires the direction of retroviral integration to a specific site in the genome by homologous recombination, integrase modification, or other methods (described below).

In a ninth embodiment, the retroviral vector provides a therapeutic effect by encoding a ribozyme (an RNA enzyme) (Haseloff and Gerlach, *Nature* 334:585, 1989) which will cleave and hence inactivate RNA molecules corresponding to a pathogenic function. Since ribozymes function by recognizing a specific sequence in the target RNA and this sequence is normally 12 to 17 bp, this allows specific recognition of a particular RNA species such as a RNA or a retroviral genome. Additional specificity may be achieved in some cases by making this a conditional toxic palliative (see below).

One way of increasing the effectiveness of inhibitory palliatives is to express viral inhibitory genes in conjunction with the expression of genes which increase the probability of infection of the resistant cell by the virus in question. The result is a nonproductive "dead-end" event which would compete for productive infection events. In the specific case of HIV, vectors may be delivered which inhibit HIV replication (by expressing anti-sense tat, etc., as described above) and also overexpress proteins required for infection, such as CD4. In this way, a relatively small number of vector-infected HIV-resistant cells act as a "sink" or "magnet" for multiple nonproductive fusion events with free virus or virally infected cells.

(ii) Conditional Toxic Palliatives

Another approach for inhibiting a pathogenic agent is to express a palliative which is toxic for the cell expressing the pathogenic condition. In this case, expression of the palliative from the proviral vector should be limited by the presence of an entity associated with the pathogenic agent, such as an intracellular signal identifying the pathogenic state in order to avoid destruction of nonpathogenic cells. This cell-type specificity may also be conferred at the level of infection by targeting recombinant retrovirus carrying the vector to cells having or being susceptible to the pathogenic condition.

In one embodiment of this method, a recombinant retrovirus (preferably, but not necessarily, a recombinant MLV retrovirus) carries a vector construct containing a cytotoxic gene (such as ricin) expressed from an event-specific promoter, such as a cell cycle-dependent promoter (e.g., human cellular thymidine kinase or transferrin receptor promoters), which will be transcriptionally active only in rapidly proliferating cells, such as tumors. In this manner, rapidly replicating cells, which contain factors capable of activating transcription from these promoters, are preferentially destroyed by the cytotoxic agent produced by the proviral construct.

In a second embodiment, the gene producing the cytotoxic agent is under control of a tissue-specific promoter, where the tissue specificity corresponds to the origin of the tumor. Since the viral vector preferentially integrates into the genome of replicating cells (for example, normal liver cells are not replicating, while those of a hepatocarcinoma are), these two levels of specificity (viral integration/replication and tissue-specific transcriptional regulation) lead to preferential killing of tumor cells. Additionally, event-sdecific and tissue-specific promoter elements may be artificially combined such that the cytotoxic gene product is expressed only in cell types satisfying both criteria (e.g., in the example above, combined promoter elements are functional only in rapidly dividing liver cells). Transcriptional control elements may also be amplified to increase the stringency of cell-type specificity.

These transcriptional promoter/enhancer elements need not necessarily be present as an internal promoter (lying between the viral LTRs) but may be added to or replace the transcriptional control elements in the viral LTRs which are themselves transcriptional promoters, such that conditionsdecific transcriptional expression will occur directly from the modified viral LTR. In this case, either the condition for maximal expression will need to be mimicked in retroviral packaging cell lines (e.g., by altering growth conditions, supplying necessary transregulators of expression or using the appropriate cell line as a parent for a packaging line), or the LTR modification is limited to the 3' LTR U3 region, to obtain maximal recombinant viral titres. In the latter case, after one round of infection/integration, the 3' LTR U3 is now also the 5' LTR U3, giving the desired tissue-specific expression.

In a third embodiment, the proviral vector construct is similarly activated but expresses a protein which is not itself cytotoxic, and which processes within the target cells a compound or a drug with little or no cytotoxicity into one which is cytotoxic (a "conditionally lethal" gene product). Specifically, the proviral vector construct carries the herpes simplex virus thymidine kinase ("HSVTK") gene downstream and under the transcriptional control of an HIV promoter (which is known to be transcriptionally silent except when activated by HIV tat protein). Expression of the tat gene product in human cells infected with HIV and carrying the proviral vector construct causes increased production of HSVTX. The cells (either in vitro or in vivo) are then exposed to a drug such as acyclovir or its analogues (FIAU, FIAC, DHPG). These drugs are known to be phosphorylated by HSVTK (but not by cellular thymidine kinase) to their corresponding active nucleotide triphosphate forms (see, for example, Schaeffer et al., *Nature* 272:583, 1978). Acyclovir and FIAU triphosphates inhibit cellular polymerases in general, leading to the specific destruction of cells expressing HSVTK in transgenic mice (see Borrelli et al., *Proc. Natl. Acad. Sci. USA* 85:7572, 1988). Those cells containing the recombinant vector and expressing HIV tat protein are selectively killed by the presence of a specific dose of these drugs. In addition, an extra level of specificity is achieved by including in the vector the HIV rev protein, responsive CRS/CAR sequences. In the presence of the CRS sequence gene expression is suppressed, except in the presence of the CAR sequences and the rev protein. Example 5 provides an illustration of this technique.

EXAMPLE 5

Vector to Conditionally Potentiate the Toxic Action of ACV or Its Analogues

Construction of Vectors

Figure 7:
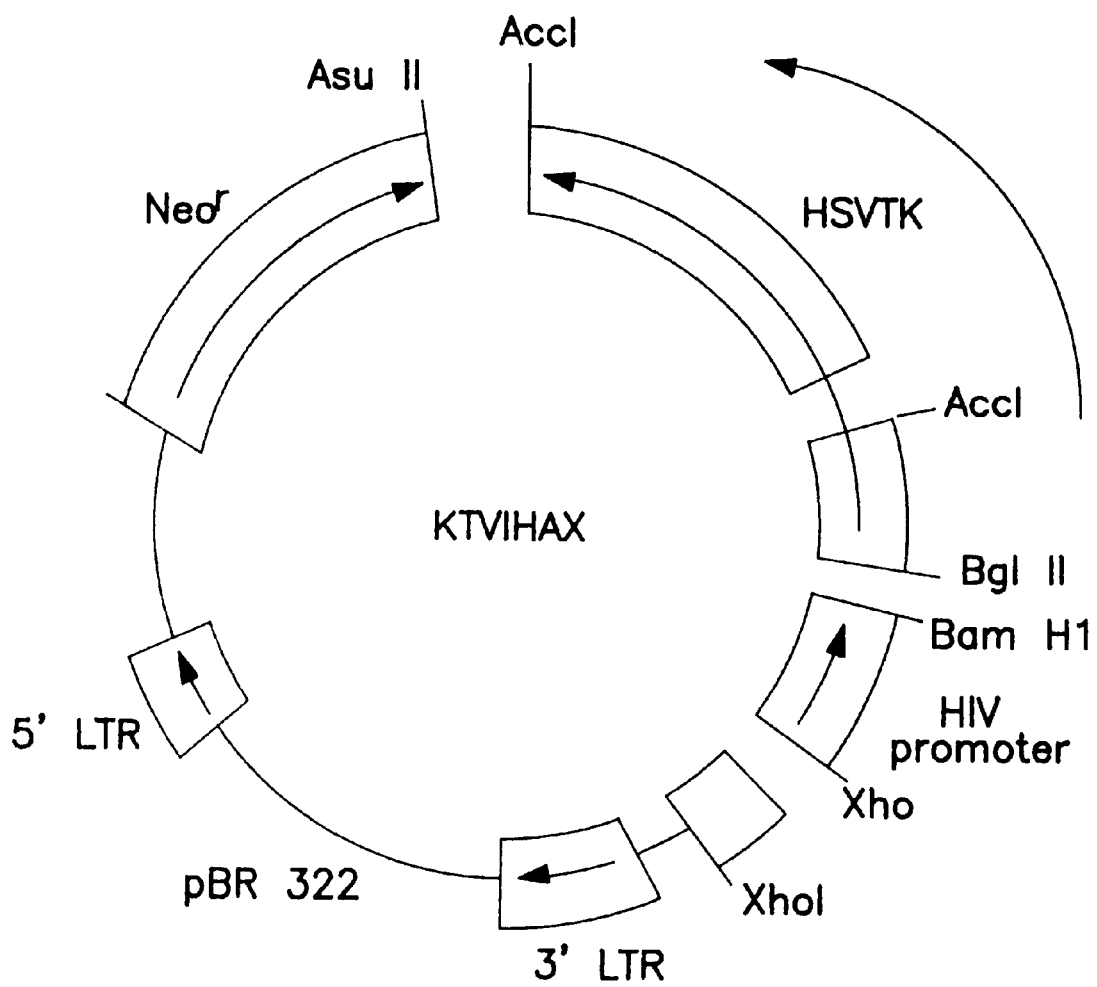
FIG. 7 illustrates the construction of the plasmid carrying the vector KTVIHAX.

A. Construction of DKTVIHAX (see FIG. 7).
1. The 9.2 kb Asu II/Xho I fragment was isolated from vector pN2 DNA.
2. The 0.6 kb Xho I/Bam HI promoter fragment was isolated from plasmid pSKHL.
3. The 0.3 kb Bgl II/Acc I and 1.5 kb Acc I/Acc I fragment were purified from PUCTK.
4. The fragments from 1, 2, and 3 were ligated, transformed into bacteria, and appropriate Amp$^r$ clones of the given structure identified by restriction enzyme analysis.

Figure 8:
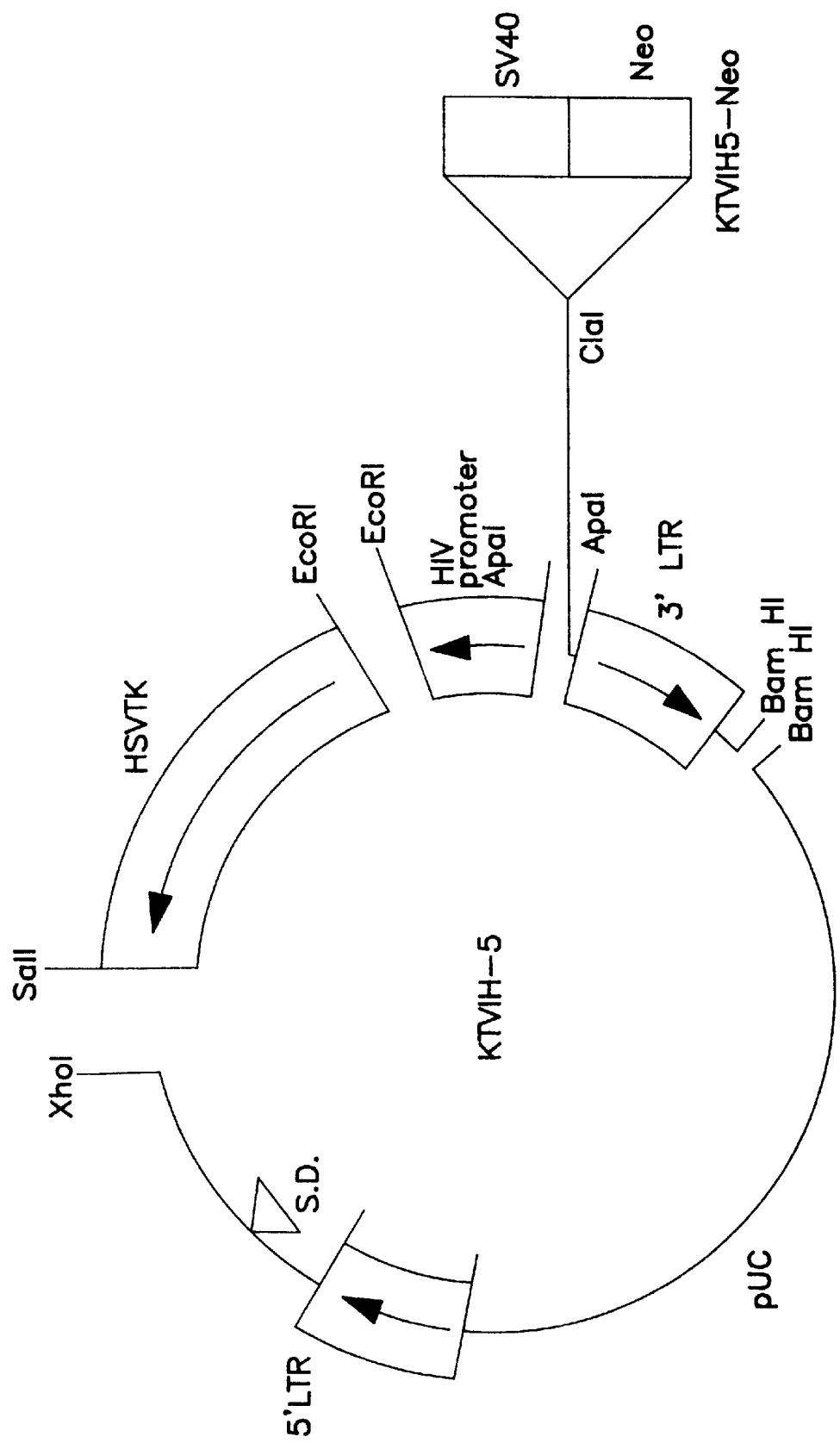
FIG. 8 illustrates the construction of the plasmids carrying the vectors KTVIH5 (without SV-Neo) and KTVIH Neo (with SV-Neo).

B. Construction of pKTVIH-5 and pKTVIH5 Neo retroviral vectors (see FIG. 8).
1. The 4.5 kb 5' LTR and vector fragment was isolated as an Xho I/Bam HI fragment from vector p31N25delta(+).
2. The 1.0 kb 3' LTR was isolated as an Apa I/Bam HI fragment from pN2R3(+) fragment.
3. The 0.6 kb HIV promoter element was isolated from pSKHL as an Apa I/Eco R1 fragment.
4. The HSVTK coding sequence and transcriptional termination sequences were isolated as 1.8 kb Eco RI/Sal I fragment from pUCTK.
5. The fragments from 1–4 were combined, ligated, transformed into bacteria, and clones of the given structure were identified by restriction enzyme analysis (pKTVIH-5).
6. Plasmid pKTVIH5 Neo was constructed by linearizing pKTVIH5 with Cla I; mixing with a 1.8 kb Cla I fragment containing the bacterial lac UV5 promoter, SV40 early promoter, and Tn5 Neo$^r$ marker, ligating, transforming bacteria and selecting for kanamycin resistance. Clones with the insert in the indicated orientation were identified by restriction analysis.

Figure 9A:
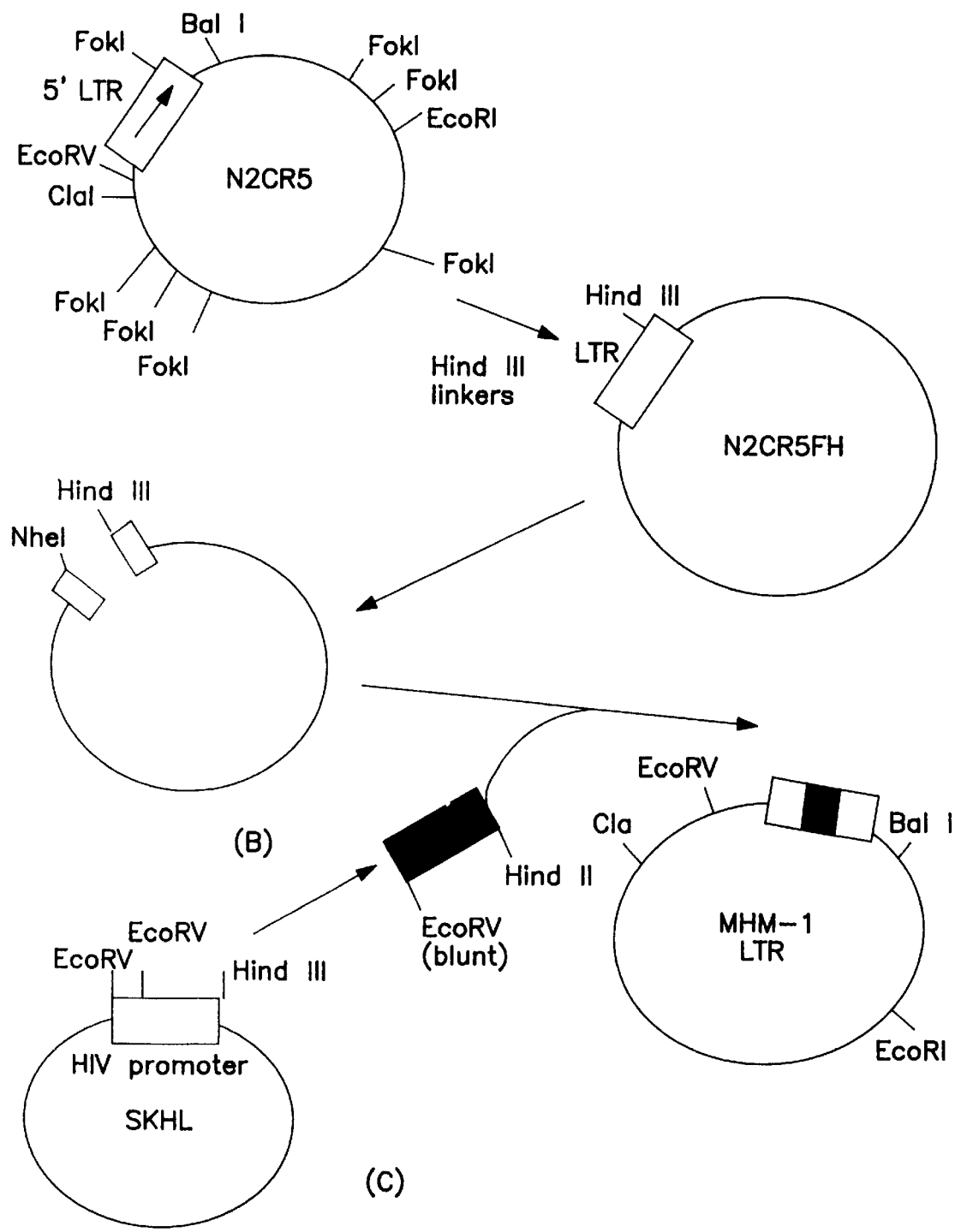
FIG. 9 illustrates construction of the plasmid carrying the vector MHMTK-Neo.
Figure 9B:
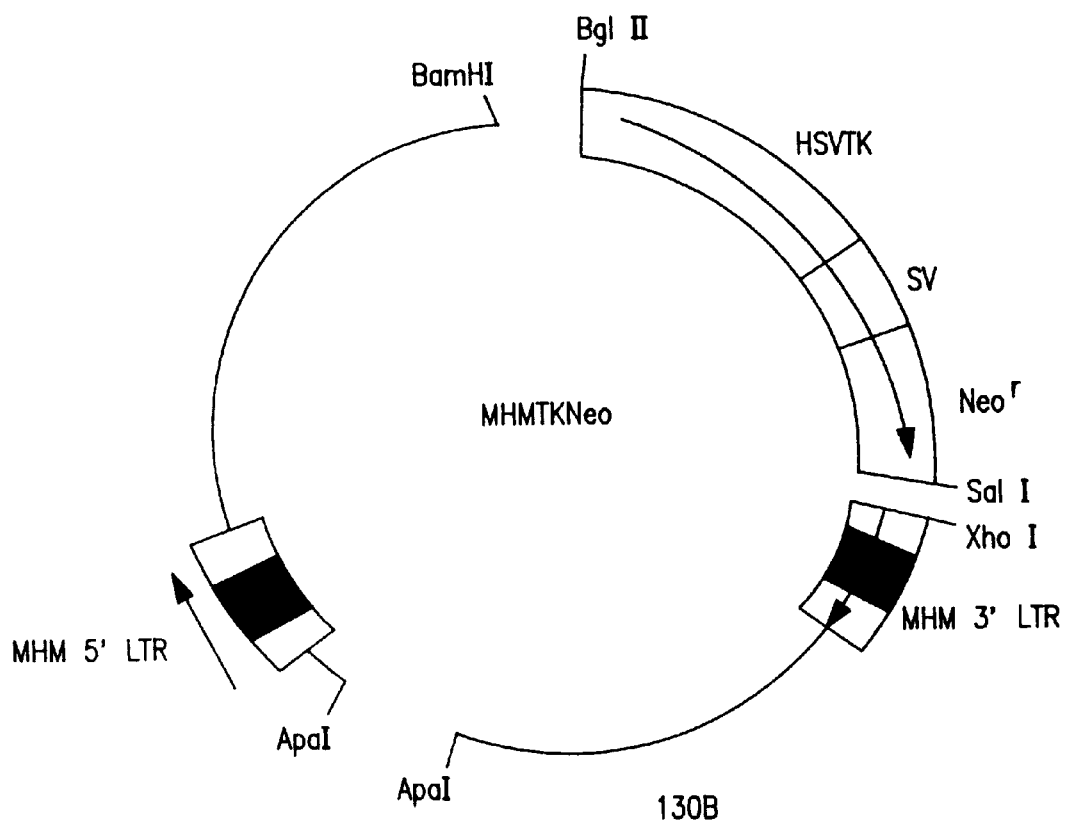

C. Construction of MHMTK Neo retroviral vector (see FIG. 9).
1. Construction of intermediate plasmid MHM-1 LTR.
   a) Plasmid pN2CR5 was linearized by partial digestion with Fok I, the 5' overhang filled in with deoxynucleotide triphosphates using Klenow DNA polymerase, and Hind III linkers inserted. After transformation into bacteria, a clone with a Hind III linker inserted in the MLV LTR Fok I site was identified by restriction enzyme analysis (pN2CR5FH).
   b) Plasmid pN2CR5FH was linearized with Nhe I, the 5' overhang filled in with Klenow polymerase digested with Hind III, and the 4.3 kb fragment with promoterless MLV sequences isolated.
   c) 0.5 kb Eco RV/Hind III HIV promoter sequences were isolated from pSKHL.
   d) b and c were mixed, ligated, used to transform bacteria, and the structure of MHM-1 was confirmed by restriction enzyme analysis.
2. The 0.7 kb Eco RV/Bal I fragment isolated from MHM-1 was subcloned into the Eco RV site of plasmid I30B (a modified IBI30 plasmid containing additional Bgl II, Bst II, Neo I and Nde I sites in the polylinker). After transformation into bacteria, clones with the appropriate orientation were identified by restriction enzyme analysis (pMHMB).
3. Plasmid pMHMB was digested with Apa I and Xho I and gel purified.
4. MHM-1 was digested with Apa I/Bam HI and the 1.8 kb MHMLTR/leader sequence gel purified.
5. The 2.8 kb Bgl II/Sal I fragment containing the HSVTK coding region upstream of the SV40 early promoter driving Neo$^r$ taken from pTK-3 (see FIG. 3).
6. 3–5 were mixed, ligated, used to transform bacteria, and appropriate clones were identified by restriction enzyme analysis.

This vector and similar vectors which contain inducible elements in their LTR's result in an added safety feature. Briefly, since the LTR is inactive in the absence of HIV, insertional downstream activation of undesirable host genes (such as proto-oncogenes) does not occur. However, tat expression in the packaging cell line allows facile manipulation of the virion in tissue culture.

D. Construction of RRKTVTH retroviral vector (see FIG. 10)
1. The 9.2 kb Asu II/Xho I fragment was isolated from vector pN2 DNA.
2. The 0.6 kb Xho I/Eco R1 HIV promoter fragment was isolated from plasmid pSKHL.
3. The HIV rev responsive HSVTK (RRTK) was constructed in the following manner:
   a) The HSVTK gene was subcloned as a 1.8 kb HinC II/Pvu II fragment into the Eco RV site of vector SK$^+$ (pSTK[−]).

b) The 1.8 kb Kpn I/Hind III fragment which contains the CRS/CAR elements from HIV env was repaired and blunt-end ligated into the Sma I site of vector 130B (pCRS/CAR[+/−]). I30B is a modified IBI30 plasmid containing the same additional restriction sites as for pUC31 with an Nde I site instead of the IBI30 Xho I site.
c) The 3.6 kb BssH II/Eco R1 fragment containing vector and HSVTK polyadenylation signals was isolated from pSTK(−),
d) The 1.8 kb Bam HI/BssH II CRS/CAR fragment was isolated from pCRS/CAR(−).
e) The 1.2 Eco R1/Bam HI coding sequence fragment was isolated from pTKdeltaA.
f) C, D and E were ligated and appropriate recombinants screened by restriction enzyme analysis.
4. Rev-responsive HSVTK was isolated as a 3.6 kb Eco R1/Cla I fragment.
5. 1, 2 and 4 were ligated and appropriate recombinants identified by restriction enzyme analysis.

Figure 11:
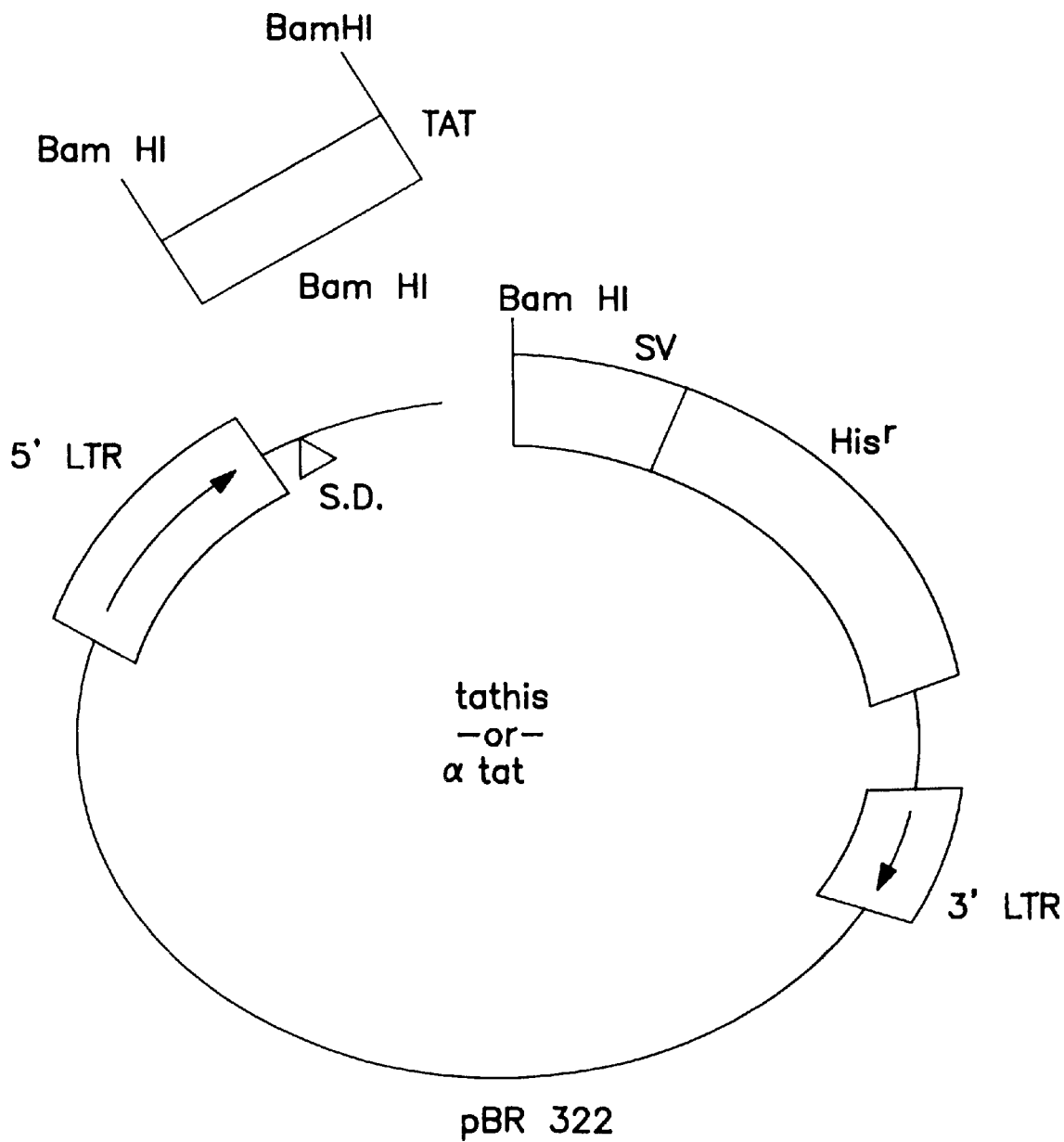
FIG. 11 illustrates the construction of the plasmids carrying the tat-his (tat in sense direction) or αtat (tat in antisense direction) vectors.

E. Construction of tat and anti-tat expression vectors (see FIG. 11).

These vectors are used as pseudo-HIV to test-activate tat-dependent HSVTX vectors.

1. The His$^r$ expression vector pBamHis was linearized with Bam HI and treated with calf intestinal phosphatase.
2. The Sac I site of pCV-1 was mutagenized to a Bam HI site and the 350 bp Bam HI coding sequence of HIV tat was isolated.
3. The fragments purified in steps 1 and 2 were mixed, ligated, used to transform bacteria, and clones with tat in both orientations (expressing tat or the "anti-sense" tat) were identified by restriction enzyme analysis.

These constructs were used to generate infectious recombinant vector particles in conjunction with a packaging cell line such as PA317, as described above. These vectors are genetically stable and result in predictable proviral structure as judged by Southern blot analysis of restriction-enzyme-digested genomic DNA from individual clones of infected cells (39/40 clones tested had proviruses of the expected size).

The biological properties of these retroviral vectors are described hereinafter. The HIV tat gene ("tathis" vector—see FIG. 11) was transfected into mouse PA317 cells. Five individual histidinol-resistant subclones were obtained (TH 1–5) which express HIV tat. These cells are thus an experimental model for HIV infection. The vectors KTVIHAX, KTVIH5NEO, and MHMTKNEO, were subsequently introduced by infection into these tatexpressing cell lines as well as their parent cell line lacking tat. Cell viability was then determined in various concentrations of the HSVTK-specific cytotoxic drug, acyclovir (ACV). The data are reported here as LD50 (the drug concentration at which 50% toxicity is observed). The parental cell line containing the vector but lacking tat (non-HIV-infected model) showed no detectable toxicity by ACV at the concentrations tested (see FIG. 12). These cells thus require 100 uM ACV or greater for cytotoxicity. This is true also for these cells lacking the vectors. Thus the vectors alone, ACV alone, or even the vector +ACV (solid boxes) is not cytotoxic. However, cell lines which express HIV tat (the experimental representation of an HIV infection) are effectively killed by ACV. This is true to varying degrees for all three vectors tested. These data indicate that HIV-infected cells will be killed in the presence of ACV and "potentiator" vectors.

In an analogous experiment, vectors KTVIHAX and KTVIH5 Neo were introduced by infection into human T-cell and monocyte cell lines Sup T1, HL60 and U937 cells. Subsequently, these cells were infected with tat his or ftat vectors, selected in histidinol, and cell viability determined at various concentrations of the ACV analog, FIAU. The $LD_{50}$ reported in Table 2 (below) indicate that a vector dependent increase in FIAU toxicity occurs in the absence of HIV tat but is increased an additional ten- to twentyfold when tat is present. This indicates that although there is a baseline HSVTK expression in all but HL60 cells, expression is even greater in the presence of HIV tat.

TABLE 2

HIV tat inducibility of FIAU cytotoxicity in human monocyte and T-cell lines infected with conditionally lethal recombinant retroviral vectors

| Cell Type | Vectors | tat | LD50FIAU ($\mu$M) |
|---|---|---|---|
| HL60 | — | − | 50 |
| ("monocyte") | — | + | 50 |
| | KTVIHAX | − | 50 |
| | KTVIHAX | + | <0.2 |
| | KTVIH5Neo | − | 50 |
| | KTVIH5Neo | + | <0.2 |
| U937 | — | − | 10 |
| ("monocyte") | KTVIHAX | − | 0.5 |
| | KTVIHAX | + | 0.05 |
| | KTVIH5Neo | − | 0.5 |
| | KTVIH5Neo | + | 0.05 |
| Sup T1 | — | − | 10 |
| ("T-cell") | — | + | 5 |
| | KTVIHAX | − | 0.5 |
| | KTVIHAX | + | 0.05 |
| | KTVIH5Neo | − | 0.5 |
| | KTVIH5Neo | + | 0.05 |
| H9 | — | − | 10 |
| ("T-cell") | KTVIHAX | − | 2 |
| | KTVIHAX | + | 0.2 |
| | KTVIH5Neo | − | 1 |
| | KTVIH5Neo | + | 0.05 |

Similarly, HIV infection of human T-cell line H9 +/− FIAU show a fivefold preferential inhibition (through cell killing) of HIV infection. Cultures were first treated with vector, then challenged with HIV for 4 days. Viral supernatants were then titred using the HIV assay, as described in Section IV.

In the case of HIV-infected cells, expression of the conditionally lethal HSVTK gene may be made even more HIV-specific by including cis-acting elements in the transcript ("CRS/CAR"), which require an additional HIV gene product, rev, for optimal activity (Rosen et al., Proc. Natl. Acad. Sci. USA 85:2071, 1988). Such a tat- and rev-responsive vector (RRKTVIH) has been constructed (see FIG. 10) and amphotrophic virus has been generated. More generally, cis elements present in mRNAs have been shown in some cases to regulate mRNA stability or translatability. Sequences of this type (i.e., post-transcriptional regulation of gene expression) may be used for event- or tissue-specific regulation of vector gene expression. In addition, multimerization of these sequences (i.e., rev-responsive "CRS/CAR" or tat-responsive "TAR" elements for HIV) could result in even greater specificity. It should be noted that this kind of conditional activation of an inactive precursor into an active product in cells may also be achieved using other viral vectors with a shorter term effect, e.g., adenovirus vectors. Such vectors are capable of efficiently entering cells and expressing proteins encoded by the vector over a period of time from a couple of days to a month or so. This period of time should be sufficient to allow killing of cells which are infected by both HIV and the recombinant virus, leading to HIV dependent activation of expression of a gene carried by the recombinant virus. This gene expression would then allow conversion of an inactive precursor into an active (e.g., lethal) product.

Production, concentration and storage of vector preparations is as previously described. Administration is by direct in vivo administration as before or by ex corpore treatment of PBL and/or bone marrow. Doses will be at approximately the same levels as for Example 4. Targeting of viral vector infection will not be through the CD4 receptor, but may be accomplished through producing vector particles which will infect cells using the HIV env protein (gp120) as a receptor. Such HIV-tropic viruses may be produced from an MLV-based packaging cell line constructed from cells which have naturally high levels of CD4 protein in their cell membrane (for example, Sup T1 cells) or from any cell type "engineered" to express the protein. The resultant virions, which form by budding from the cell membrane itself, contain the CD4 protein in their membrane. Since membranes containing CD4 are known to fuse with membranes carrying HIV env, these virions should fuse with cells containing HIV env and result in the specific infection of HIV-infected cells which have gp120 on their surface. Such a packaging cell line may require the presence of an MLV env protein to allow proper virion assembly and budding to result in infectious virions. If so, an MLV env which does not infect human cells (such as ecotropic env) would be used such that viral entry will occur only through the CD4/HIV env interaction and not through the MLV env cell receptor, which would presumably not depend upon the presence of HIV-env for infection. Alternatively, the requirement for MLV env may be satisfied by a hybrid envelope where the amino-terminal binding domain has been replaced by the amino-terminal HIV-env binding domain of CD4. This inversion of the normal virus-receptor interaction can be used for all types of viruses whose corresponding cellular receptor has been identified.

In a similar manner to the preceding embodiment, the retroviral vector construct can carry a gene for phosphorylation, phosphoribosylation, ribosylation, or other metabolism of a purine- or pyrimidine-based drug. This gene may have no equivalent in mammalian cells and might come from organisms such as a virus, bacterium, fungus, or protozoan. An example of this would be the *E. coli* guanine phosphoribosyl transferase gene product, which is lethal in the presence of thioxanthine (see Besnard et al., *Mol. Cell. Biol.* 7:4139–4141, 1987). Conditionally lethal gene products of this type have potential application to many presently known purine- or pyrimidine-based anticancer drugs, which often require intracellular ribosylation or phosphorylation in order to become effective cytotoxic agents. The conditionally lethal gene product could also metabolize a nontoxic drug, which is not a purine or pyrimidine analogue, to a cytotoxic form (see Searle et al., *Brit. J. Cancer* 53:377–384, 1986).

Mammalian viruses in general tend to have "immediate early" genes which are necessary for subsequent transcriptional activation from other viral promoter elements. Gene products of this nature are excellent candidates for intracellular signals (or "identifying agents") of viral infection. Thus, conditionally lethal genes from transcriptional promoter elements responsive to these viral "immediate early" gene products could specifically kill cells infected with any particular virus. Additionally, since the human α and β interferon promoter elements are transcriptionally activated in response to infection by a wide variety of nonrelated viruses, the introduction of vectors expressing a conditionally lethal gene product like HSVTK, for example, from these viral-responsive elements (VRE) could result in the destruction of cells infected with a variety of different viruses.

In a fourth embodiment, the recombinant retrovirus carries a gene specifying a product which is not in itself toxic, but when processed or modified by a protein, such as a protease specific to a viral or other pathogen, is converted into a toxic form. For example, the recombinant retrovirus could carry a gene encoding a proprotein for ricin A chain, which becomes toxic upon processing by the HIV protease. More specifically, a synthetic inactive proprotein form of the toxic ricin or diphtheria A chains could be cleaved to the active form by arranging for the HIV virally encoded protease to recognize and cleave off an appropriate "pro" element.

In a fifth embodiment, the retroviral construct may express a "reporting product" on the surface of the target cells in response to the presence of an identifying agent in the cells (such as HIV tat protein). This surface protein can be recognized by a cytotoxic agent, such as antibodies for the reporting protein or by cytotoxic T-cells. In a similar manner, such a system can be used as a detection system (see below) to simply identify those cells having a particular gene which expresses an identifying protein, such as the HIV tat gene.

Similarly, in a sixth embodiment, a surface protein could be expressed which would itself be therapeutically beneficial. In the particular case of HIV, expression of the human CD4 protein specifically in HIV-infected cells may be beneficial in two ways:

1. Binding of CD4 to HIV env intracellularly could inhibit the formation of viable viral particles much as soluble CD4 has been shown to do for free virus, but without the problem of systematic clearance and possible immunogenicity, since the protein will remain membrane bound and is structurally identical to endogenous CD4 (to which the patient should be immunologically tolerant).

2. Since the CD4/HIV env complex has been implicated as a cause of cell death, additional expression of CD4 (in the presence of excess HIV-env present in HIV-infected cells) leads to more rapid cell death and thus inhibits viral dissemination. This may be particularly applicable to monocytes and macrophages, which act as a reservoir for virus production as a result of their relative refractility to HIV-induced cytotoxicity (which, in turn, is apparently due to the relative lack of CD4 on their cell surfaces).

EXAMPLE 6

Construction of p4TVIHAX retroviral vector (see FIG. 13)

1. The 9.4 kb Asu II/Xho I fragment was isolated from pN2.

2. The 0.6 kb Xho I/Eco R1 HIV promoter fragment was isolated from pSKHL.

3. The 1.4 kb coding region for human CD4 was isolated as an Eco R1/Bst Yl (Xho II) fragment from the expression vector, pMV7T4.

4. The (A)n signal of HSVTK was isolated as a 0.3 kb Apa I/Sma I fragment, 3' repaired with T4 polymerase and dNTP's and cloned into the Sma I site of pUC31. After transforming bacteria, clones were screened for orientation by restriction enzyme analysis (p31[A]n[+/−]). The 0.3 kb (A)n signal was then isolated as a 0.3 kb Bgl II/Acc I fragment.

5. 1–4 clones were mixed, ligated, used to transform bacteria and clones were identified by restriction enzyme analysis.

Recombinant amphotrophic retroviruses have been produced and introduced into human monocyte and T-cell lines lacking or containing the HIV tat expression vector, tathis. Syncytia assays with HIV env-expressing mouse fibroblasts show that monocyte cell lines HL60 and U937 themselves lack sufficient CD4 to fuse with these cells. However, HL60 and U937 cells containing vector 4TVIHAX can fuse with the reporter cells (HIV-env expressing cells) when HIV tat is present, but not in its absence. These data indicate that CD4 expression is inducible and biologically active (as judged by syncytia formation). Experiments with the vector in human T-cell line, H9, indicated exceptionally high toxicity due to HIV infection and a correspondingly low HIV titre (more than 200-fold lower than the HIV titre produced in H9 cells lacking the vector).

In a seventh embodiment, the retroviral vector codes for a ribozyme which will cleave and inactivate RNA molecules essential for viability of the vector infected cell. By making ribozyme production dependent on an intracellular signal corresponding to the pathogenic state, such as HIV tat, toxicity is specific to the pathogenic state.

IV. Immune Down-Regulation

As briefly described above, the present invention provides recombinant retroviruses which carry a vector construct capable of suppressing one or more elements of the immune system in target cells infected with the retrovirus.

Specific down-regulation of inappropriate or unwanted immune responses, such as in chronic hepatitis or in transplants of heterologous tissue such as bone marrow, can be engineered using immune-suppressive viral gene products which suppress surface expression of transplantation (MHC) antigen. Group C adenoviruses Ad2 and Ad5 possess a 19 kd glycoprotein (gp 19) encoded in the E3 region of the virus. This gp 19 molecule binds to class I MHC molecules in the endoplasmic reticulum of cells and prevents terminal glycosylation and translocation of class I MHC to the call surface. For example, prior to bone marrow transplantation, donor bone marrow cells may be inf ected with gp 19-encoding vector constructs which upon expression of the gp 19 inhibit the surface expression of MHC class I transplantation antigens. These donor cells may be transplanted with low risk of graft rejection and may require a minimal immunosuppressive regimen for the transplant patient. This may allow an acceptable donor-recipient chimeric state to exist with fewer complications. Similar treatments may be used to treat the range of so-called autoimmune diseases, including lupus erythromiatis, multiple sclerosis, rheumatoid arthritis or chronic hepatitis B infection.

An alternative method involves the use of anti-sense message, ribozyme, or other specific gene expression inhibitor specific for T-cell clones which are autoreactive in nature. These block the expression of the T-cell receptor of particular unwanted clones responsible for an autoimmune response. The anti-sense, ribozyme, or other gene may be introduced using the viral vector delivery system.

V. Expression of Markers

The above-described technique of expressing a palliative in a cell, in response to some identifying agent, can also be modified to enable detection of a particular gene in a cell which expresses an identifying protein (for example, a gene carried by a particular virus), and hence enable detection of cells carrying that virus. In addition, this technique enables the detection of viruses (such as HIV) in a clinical sample of cells carrying an identifying protein associated with the virus.

This modification can be accomplished by providing a genome coding for a product, the presence of which can be readily identified (the "marker product"), and carrying a promoter, which responds to the presence of the identifying protein in indicator cells, by switching expression of the reporting product between expressing and nonexpressing states. For example, HIV, when it infects suitable indicator cells, makes tat and rev. The indicator cells can thus be provided with a genome (such as by infection with an appropriate recombinant retro-virus) which codes for a marker gene, such as the alkaline phosphatase gene, β-galactosidase gene or the luciferase gene, and a promoter, such as the HIV promoter, which controls expression of the marker gene. When the indicator cells are exposed to a clinical sample to be tested, and the sample contains HIV, the indicator cells become infected with HIV, resulting in tat and/or rev expression (an identifying protein) therein. The HIV expression controls in the indicator cells would then respond to tat and/or rev proteins by switching expression of genes encoding β-galactosidase, luciferase, or alkaline phosphatase (marker products) from normally "off" to "on." In the case of β-galactosidase or alkaline phosphatase, exposing the cells to substrate analogues results in a color or fluorescence change if the sample is positive for HIV. In the case of luciferase, exposing the sample to luciferin will result in luminescence if the sample is positive for HIV. For intracellular enzymes such as β-galactosidase, the viral titre can be measured directly by counting colored or fluorescent cells, or by making cell extracts and performing a suitable assay. For the membrane bond form of alkaline phosphatase, virus titre can also be measured by performing enzyme assays on the cell surface using a fluorescent substrate. For secreted enzymes, such as an engineered form of alkaline phosphatase, small samples of culture supernatant are assayed for activity, allowing continuous monitoring of a single culture over time. Thus, different forms of this marker system can be used for different purposes. These include counting active virus or sensitively and simply measuring viral spread in a culture and the inhibition of this spread by various drugs.

Further specificity can be incorporated into the preceding system by testing for the presence of the virus either with or without neutralizing antibodies to that virus. For example, in one portion of the clinical sample being tested, neutralizing antibodies to HIV may be present; whereas in another portion there would be no neutralizing antibodies. If the tests were negative in the system where there were antibodies and positive where there were no antibodies, this would assist in confirming the presence of HIV.

Within an analogous system for an in vitro assay, the presence of a particular gene, such as a viral gene, may be determined in a cell sample. In this case, the cells of the sample are infected with a suitable retroviral vector which carries the reporter gene linked to the expression controls of the virus of interest. The reporter gene, after entering the sample cells, will express its reporting product (such as β-galactosidase or luciferase) only if the host cell expresses the appropriate viral proteins.

These assays are more rapid and sensitive, since the reporter gene can express a greater amount of reporting product than identifying agent present, which results in an amplification effect. Example 7 describes a representative technique for detecting a gene which expresses an identifying protein.

EXAMPLE 7

HIV-Specific Marker System or Assay

A. Constructs

Reporter constructs under the control of the HIV expression system are shown in FIG. 14 (a recombinant retroviral vector) and in FIG. 15 (a simple plasmid used by transfection). The pieces of these preferred vector and plasmid reporters were derived as follows:

The retroviral backbone was derived from the construct pAFVXM (Krieger et al., *Cell* 38:384, 1984), which had been linearized using Xho I and Cla I. SV$_2$neo was obtained from the plasmid pKoneo (Hanahan, unpubl.) by isolation of the 1.8 kb Cla I fragment.

The HIV LTR was isolated as a 0.7 kb Hind III fragment from the plasmid pCl5CAT (Arya et al., *Science* 229:69, 1985). Beta-gal was obtained from the plasmid pSP65 β-gal (Cepko, pers. comm.) as a Hind III-Sma I fragment. A secreted form of human placental alkaline phosphatase was produced by introduction of a universal terminator sequence after amino-acid 489 of the cell surface form of alkaline phosphatase (as described by Berger et al., *Gene* 66:1, 1988). The secreted alkaline phosphatase gene was isolated as a 1.8 kb Hind III to Kpn I fragment. The CRS-C-R sequences from HIV env were obtained by isolating the 2.1 kb Kpn I to Bam HI fragment from HTLVIIIB/BH1OR3 (Fisher et al., *Science* 233:655, 1986). This fragment was inserted into pUC31 linearized by Bam HI, and Kpn I pUC31 is pUC19 (Yanisch-Perron et al., *Gene* 33:103, 1985) with extra Xho I, Bgl II, Bssh II and Nco I sites between the Eco R1 and Kpn I sites of pUC19. The Bam HI site of the resulting construct was converted to a Nco I site to allow resection of the CRS-CAR sequences by Nco I digestion. The SV40 t intron was obtained from pSVOL (de Wet et al., *Mol. Cell. Biol.* 7:725, 1987) as a 0.8 kb Nco I to Bam HI fragment.

B. Indicator Cells and Retroviral Vectors

Human T-cell (H-9, CEM and Sup T1) and monocyte (U-937) cell lines were obtained from ATCC, and maintained in RPM1 1640 medium supplemented with 10% fetal bovine serum and 1% penicillin/streptomycin.

The nonretroviral vectors were introduced into cell lines by electroporation using a Bio-Rad Gene Pulser. The cell lines were selected in G-418 (1 mg/ml) for 2–3 weeks to obtain stable G-418$_R$ cell lines, and then dilution cloned to obtain clonal cell lines.

The pAF vectors were transfected into the PA317 packaging cell line as a calcium phosphate precipitate (Wigler et al., *Cell* 16:777, 1979). The virus-producing PA317 cells were co-cultivated with human monocyte cell lines for 24 hours in the presence of polybrene, after which the suspension calls were removed and selected in G-418 and subcloned as above.

C. Assay

Stable cell lines were infected with HIV (HTLV III$_B$) and the cells (β-gal) or media (alkaline phosphatase) assayed on a daily basis for 6 days post-infection.

β-Galactosidase Assay

Infected cells could be assayed by either: (i) In situ histochemical staining as described by MacGregor et al. *Somatic Cell and Mol. Genetics* 13:253, 1987); or (ii) by using cell extracts in a solution enzymatic assay with ONPG as a substrate (Norton and Coffin, *Mol. Cel. Biol.* 5:281, 1985).

Soluble Alkaline Phos-hatase Assay

Medium was removed from infected cells, microfuged for 10 seconds, and then heated to 68° C. for 10 minutes to destroy endogenous phosphatases. The medium was then microfuged for 2 minutes and an aliquot (10–50 µl) removed for assay. 100 µl of buffer (1 M diethanolamine, pH 9.8; 0.5 Mm MgCl$_2$; 10 mM L-homoarginine) was added and then 20 µl of 120 mM p-nitrophenylphosphate (in buffers) was added. The A$_{405}$ of the reaction mixture was monitored using an automatic plate reader.

FIGS. 16 and 17 depict typical results of a time course of infection of Sup T1 cells using the alkaline phosphatase assay in the presence of varying concentrations of antiviral drugs. The "+" and "−" on day 6 indicate the presence or absence of syncytia.

The present invention provides a number of other techniques (described below) which can be used with the retroviral vector systems employed above, so as to enhance their performance. Alternatively, these techniques may be used with other gene-delivery systems.

VI. Packaging Cell Selection

This aspect of the present invention is based, in part, upon the discovery of the major causes of low recombinant virus titres from packaging cell lines (PCL), and of techniques to correct those causes. Basically, at least five factors may be postulated as causes for low recombinant virus titres:

1. the limited availability of viral packaging proteins;
2. the limited availability of retroviral vector RNA genomes;
3. the limited availability of cell membrane for budding of the recombinant retroviruses;
4. the limited intrinsic packaging efficiency of the retroviral vector genome; and
5. the density of the receptor specific for the envelope of a given retrovirus.

As noted above, the limited availability of viral packaging proteins is the initial limiting factor in recombinant retrovirus production from packaging cells. When the level of packaging protein in the packaging cells is increased, titre increases to about $10^5$ infectious units/milliliter, following which increasing packaging protein level has no further effect on titres. However, titres can be further augmented by also increasing the level of retroviral vector genome available for packaging. Thus, as described herein, it is advantageous to select producer cells that manufacture the maximum levels of packaging proteins and retroviral vector genomes. It has been discovered that the methods of identifying, and thus selecting, packaging cells and producer cells, described earlier under the section entitled "Background of the Invention," tend to lead to selection of many producer cells which produce low titres for the reasons described below.

The present invention takes advantage of the previously disadvantageous fact that the protein expression level of a gene downstream from the 5' LTR or other promoter, and spaced therefrom by an intervening gene, is substantially less than if the intervening gene were absent. In the present invention, the selectable gene is placed downstream from a gene of the packaging genome or the gene of interest carried by the vector construct, but is still transcribed under the control of the viral 5' LTR or other promoter without any splice donor or splice acceptor sites. This accomplishes two things. First, since the packaging genes or genes of interest are now upstream with no intervening gene between themselves and the promoter, their corresponding proteins (packaging protein or protein of interest) will be expressed at a higher level (five- to twentyfold) than the selectable protein. Second, the selectable protein will be expressed on average at a lower level, with the distribution of level of expression shifting toward lower levels. In the case of the phleor protein, this shift in distribution is illustrated by the broken curve indicated in FIG. 18. However, the selection level for resistance to phleomycin remains the same, so that only the top-end expressing cells survive. The levels of the packaging protein or of the protein of interest will still be proportional, only in this case, a higher level of selectable protein corresponds to a much higher level of packaging protein or protein of interest.

Preferably, the foregoing procedure is performed using a plasmid carrying one of the proviral gag/pol or env packaging genes, along with a first selectable gene. These cells are then screened for the cells producing the highest levels of protein by reaction with an antibody against env (or possibly gag/pol), a second fluorescent antibody, and then sorted on a fluorescence-activated cell sorter (FACS). Alternatively, other tests for protein level may be used. Subsequently, the procedure and screening are repeated using those selected cells, and the other of the gag/pol or env packaging genes. In this step, a second selectable gene (different from the first) would be required downstream from the packaging gene and the cells producing the largest amount of the second viral protein selected. The procedure and screening are then repeated using the surviving cells, with a plasmid carrying the proviral vector construct bearing the gene of interest and a third selectable gene, different from the first or second selectable gene. As a result of this procedure, cells producing high titres of the desired recombinant retrovirus will be selected, and these can be cultured as required to supply recombinant retrovirus. In addition, gag and pol can be independently introduced and selected.

Example 8 describes the construction of gag/pol and env plasmids designed to use these procedures.

EXAMPLE 8

Plasmids Designed to Make High Levels of Packaging Proteins (FIG. 19)

1. The 2.7 kb Xba I fragment from pPAM (Miller et al., *Mol. Cell. Biol.* 5:431, 1985), which contains the amphotrophic env segment, was cloned in pUC18 at the Xba I site, then removed with Hind III and Sma I. This fragment was cloned into the vector pRSV neo (Gorman et al., *Mol. Cell. Biol.* 2:1044, 1982; Southern et al., *J. Mol. Appl. Genet.* 1:327, 1982) cut with Hind III and Pvu II, to give pRSV env. A 0.7 kb Bam HI to BstE II fragment from the plasmid pUT507 (Mulsant et al., *Somat. Cell. Mol. Genet.* 14:243, 1988) with the BstE II end filled in carries the phleo resistance coding sequence. The 4.2 kb Bam HI to Xho I fragment, the contiguous 1.6 kb Xho I to Xba I (Xba I filled in) from RSVenv, and the phleo fragment were ligated to give pRSVenv-phleo.

2. A fragment from the Pst I site at nucleotide 563 of MLV (*RNA Tumor Viruses*, Vol. II, Cold Spring Harbor, 1985) to the Sca I site at 5870 was derived from pMLV-K (Miller et al., 1985, op. cit.) and cloned in the Pst I to Bam HI (Ban HI filled-in) fragment from p4aA8 (Jolly et al., *Proc. Natl. Acad. Sci. USA* 80:477, 1983) that has the SV40 promoter, the pBR322 ampicillin resistance and origin of replication and the SV40 poly A site. This gives pSVgp. pSVgpDHFR was made using the following fragments: the 3.6 kb Hind III to Sal I fragment from pSVgp containing the SV40 promoter plus MLV gag and some pol sequences; the 2.1 kb Sal I to Sca I fragment from pMLV-K with the rest of the pol gene, the 3.2 kb Xba I (Xba I filled-in) to Pst I fragment from pF400 with the DHFR gene plus poly A site, pBR322 origin and half the ampicillin resistance gene; the 0.7 kb Pst I to Hind III fragment from pBR322 with the other half of the ampicillin resistance gene. This gives pSVgp-DHFR. All these constructs are shown in FIG. 19. These plasmids can be transfected into 3T3 cells or other cells and high levels of gag, pol or env obtained.

An additional method for accomplishing selection is to use a gene selection in one round and its antisense in a subsequent round. For example, gag/pol may be introduced into an HPRT-deficient cell with the HPRT gene and selected for the presence of this gene using that media which requires HPRT for the salvage of purines. In the next round, the antisense to HPRT could be delivered downstream to env and the cell selected in 6 thioguanine for the HPRT-deficient phenotype. Large amounts of antisense HPRT would be required in order to inactivate the HPRT gene transcripts, assuming no reversion occurred. A further method of accomplishing selection is described below. Co-transfection of a 10x stoichiometric excess of the expression vector over the separate selectable marker ensures high copy number of expression vector in drug resistant cell clones. In most of the examples noted herein, the gag/pol and envelope expression vectors were introduced independently (i.e., separate transfections) so that the two structural genes would not recombine or concatamerize (as transfected integrated DNA tends to do), assuring that the genes are unlinked in the genome. The steady-state level of intracellular MLV gag/pol and env was measured by protein immunoblotting. The relative ease, sensitivity, and reproducibility of immunoblotting allowed rapid, quantitative analysis of a large number of cell clones necessary to identify over-expressors of the MLV structural proteins (gag/pol in particular) (see Example 9).

In addition to the gag/pol expressing constructs which begin at nucleotide 563 of MoMLV, several others can be constructed which contain upstream lead sequences. It has been observed by Prats et al. (*RNA Tumor Viruses Meeting*, Cold Spring Harbor, N.Y., 1988) that a glycosylated form of the gag protein initiates at nucleotide 357 and a translation enhancer maps in the region between nucleotides 200–270. Therefore, gag/pol expressing constructs may be made beginning at the Bal I site (nucleotide 212) or Eag I site (nucleotide 346) to include these upstream elements and enhance vector production.

Envelope Substitutions

The ability to express gag/pol and env function separately allows for manipulation of these functions independently. A cell line that expresses ample amounts of gag/pol can be used, for example, to address questions of titre with regard to env. One factor resulting in low titres is the density of appropriate receptor molecules on the target cell or tissue. A second factor is the affinity of the receptor for the viral envelope protein. Given that env expression is from a separate unit, a variety of envelope genes (requiring different receptor proteins), such as xenotropic, polytropic, or amphotrophic envs from a variety of sources, can be tested for highest titres on a specific target tissue.

Envelope proteins from one retrovirus can often substitute, to varying degrees, for that of another retrovirus. For instance, the envelope of murine virus 4070A, HTLV I, GALV, and BLV can each substitute for that of MOMLV, albeit with a lower efficiency (Cone and Mulligan, *Proc. Natl. Acad. Sci. USA* 81:6349–53, 1984; Wilson et al., *J. Virol.* 63, 2374–78, 1989; Ban et al., *J. Gen. Virol.* 70:1987–93, 1989). To increase the number of cell types that could be infected with MLV-based vectors, PCLs were generated which individually express either amphotropic, xenotropic, or polytropic envelopes. Vector produced from any of these PCLs can be used to infect any cell which contains the corresponding distinct receptor (Rein and Schultz, *Virology* 136:144–52, 1984). Some cell types may, for instance, lack the amphotropic receptor and thus be resistant to infection with amphotropic vector, but express the xenotropic receptor and therefore be infectable by xenotropic vector. One report suggests that xenotropic vector, in the presence of replication-complement xenotropic virus, may more effectively infect human hematopoietic progenitor cells (Eglitis et al., Biochem. *Bioiphys. Res. Comm.* 151:201–206, 1988). Xenotropic vector, in the presence of replication-competent xenotropic virus, also infects cells from other species which are not easily infectable by amphotropic virus such as bovine, porcine, and equine (Delouis et al., Biochem. Biophys Res. Comm. 169:80–14, 1990). The xenotropic PCLs will therefore be useful for veterinary purposes in these species.

As a specific example, all of the amphotropic PCLs described herein (canine and human fibroblasts) were infectable by xenotropic vector but were resistant to infection by amphotropic vector, presumably due to the phenomenon of "viral interference" (cf. A. Rein, *Virology* 120:251–57, 1982). The xenotropic PCL therefore allows the facile infection of these amphotropic PCLs, which in turn produces 10–100× higher titre than PCLs whose vector has been introduced by other means (Miller et al., *Somat. Cell Mol. Genet.* 12:175–83, 1986). In principle, a PCL expressing any viral envelope which can function with the MLV vector and packaging system and whose corresponding cellular receptor is found in a given PCL, is useful for allowing vector infection of that PCL.

Vector produced from the polytropic PCL described herein has a more restricted host range on human cells than vector produced from either amphotropic or xenotropic PCLs (see data below). The polytropic PCL may therefore be particularly useful for targeting vector to a specific human cell type. The reduced homology between both xenotropic and polytropic envelopes with the MOMLV gag/pol and with the vector makes these PCLs even less likely to generate replication-competent retrovirus by homologous recombination than amphotropic PCLs. Examples of the use of these methods are set forth below (see Example 9).

Furthermore, envelopes from nonmurine retrovirus sources can be used for pseudotyping a vector. The exact rules for pseudotyping (i.e., which envelope proteins will interact with the nascent vector particle at the cytoplasmic side of the cell membrane to give a viable viral particle (Tato, *Virology* 88:71, 1978) and which will not (Vana, *Nature* 336:36, 1988), are not well characterized. However, since a piece of cell membrane buds off to form the viral envelope, molecules normally in the membrane are carried along on the viral envelope. Thus, a number of different potential ligands can be put on the surface of viral vectors by manipulating the cell line making gag and pol in which the vectors are produced or choosing various types of cell lines with particular surface markers. One type of surface marker that can be expressed in helper cells and that can give a useful vector-cell interaction is the receptor for another potentially pathogenic virus. The pathogenic virus displays on the infected cell surface its virally specific protein (e.g., env) that normally interacts with the cell surface marker or receptor to give viral infection. This reverses the specificity of the infection of the vector with respect to the potentially pathogenic virus by using the same viral protein-receptor interaction, but with the receptors on the vector and the viral protein on the cell.

It may be desirable to include a gene which encodes for an irrelevant envelope protein which does not lead to infection of target cells by the vector so produced, but does facilitate the formation of infectious viral particles. For example, one could use human Sup T1 cells as a helper line.

This human T-cell line expresses CD4 molecules at high levels on its surface. Conversion of this into a helper line can be achieved by expressing gag/pol with appropriate expression vectors and also, if necessary, the Moloney ecotropic env gene product as an irrelevant (for human cells) envelope protein (the Moloney ecotropic env only leads to infection of mouse cells). Vectors produced from such a helper line would have CD4 molecules on their surfaces and are capable of infecting only cells which express HIV env, such as HIV-infected cells.

In addition, hybrid envelopes (as described below) can be used in this system as well, to tailor the tropism (and effectively increase titres) of a retroviral vector. A cell line that expresses ample amounts of a given envelope gene can be employed to address questions of titre with regard to gag and pol.

Cell Lines

The most common packaging cell lines used for MOMLV vector systems (psi2, PA12, PA317) are derived from murine cell lines. There are several reasons why a murine cell line is not the most suitable for production of human therapeutic vectors:

1. They are known to contain endogenous retroviruses.
2. They contain nonretroviral or defective retroviral sequences that are known to package efficiently.
3. There may be deleterious effects caused by the presence of murine cell membrane components.

Several non-murine cell lines are potential packaging lines. These include Vero cells which are used in Europe to prepare polio vaccine, WI38 which are used in the U.S. in vaccine production, CHO cells which are used in the U.S. for TPA preparation, D17 or other dog cells that may have no endogenous viruses, and those described in Example 9.

The most important safety concern for the production of retroviral vectors is the inherent propensity of retroviral PCLs to generate replication-competent retrovirus after introduction of a vector (Munchau et al., *Virolocy* 176:262–65, 1990). This can occur in at least two ways: 1) homologous recombination can occur between the therapeutic proviral DNA and the DNA encoding the MOMLV structural genes ("gag/pol" and "env") present in the PCL (discussed below under "Generation of PCLS"); and 2) generation of replication-competent virus by homologous recombination of the proviral DNA with the very large number of defective endogenous proviruses found in murine cells (Steffen and Weinberg, *Cell* 15:1003–10, 1978); Canaani and Aaronson, *Proc. Natl. Acad. Sci. USA* 76:1677–81, 1979; Stoye and Coffin, *J. Virol.* 61:2659–69 1987). In addition, even murine cell lines lacking vector can produce virus spontaneously or after induction, (e.g., xenotropic virus which can replicate in human cells, Aaronson and Dunn, *J. Virol.* 13:181–85, 1974; Stephenson and Aaronson, *Proc. Natl. Acad. Sci., USA* 71:4925–29, 1974; Aaronson and Stephenson, *Biochem. Biovhys. Acta* 458:323–54, 1976). Another safety concern with the utilization of murine cells for the production of murine retroviral vectors is the observation that some of the many endogenous proviral genes (retrovirus-like genes) in the murine genome are expressed, recognized by the retroviral structural gene products of murine PCLs, and delivered and expressed in target cells with an efficiency at least comparable to that of the desired vector (Scolnick et al.,*J. Virol.* 29:964–72, 1979; Scadden et al., *J. Virol.* 64:424–27, 1990). These observations strongly suggest that murine cell lines are an unsafe choice for the production of murine retroviral vectors for human therapeutics. To circumvent the inherent safety problems associated with murine cells, PCLs have been generated exclusively from non-murine cell lines (e.g., canine and human cell lines) which are known to lack genomic sequences homologous to that of MoMLV by hybridization analysis (Martin et al., *Proc. Natl. Acad. Sci. USA* 78:4892–96, 1981). Those skilled in the art will recognize that the packaging cells described herein will have a low, but inherent capability of packaging random RNA molecules. Such RNA moleculse will not be permanently transmitted to the pseudo-infected target cell.

In addition to issues of safety, the choice of host cell line for the PCL is of importance because many of the physical (such as stability) and biological properties (such as titre) of retroviral particles are dictated by the properties of the host cell. For instance, the host cell must efficiently express (transcribe) the vector RNA genome, prime the vector for first strand synthesis with a cellular tRNA, tolerate and covalently modify the MLV structural proteins (proteolysis, glycosylation, myristylation, and phosphorylation), and the maturing virion buds from the cell membrane, carrying many of the membrane components with it.

EXAMPLE 9

Packaging Cell Selection

A. MLV structural gene expression vectors

To decrease the possibility of replication-competent virus being generated by genetic interactions between the MLV proviral vector DNA and the structural genes of the PCL, separate expression vectors, each lacking the viral LTR, were generated to express the gag/pol and env genes independently. To further decrease the possibility of homologous recombination with MLV vectors and the resultant generation of replication-complement virus, minimal sequences other than the protein coding sequences were used. In order to express high levels of the MLV structural proteins in the host cells, strong transcriptional promoters (CMV early and Ad5 major late promoters) were utilized. An example of the construction of a MoMLV gag/pol expression vector (pSCV10, see FIG. 19B.1) follows:

1. The 0.7 Kb HinCII/XmaIII fragment encompassing the human cytomegalovirus (CMV) early transcriptional promoter (Boshart et al., *Cell* 41:521–30, 1985) was isolated.

2. A 5.3 Kb PstI(partial)/ScaI fragment from the MoMLV proviral plasmid, MLV-K (Miller et al., *Mol. Cell Biol.* 5:531, 1985) encompassing the entire gag/pol coding region was isolated.

3. A 0.35 Kb DraI fragment from SV40 DNA (residues 2717–2363) encompassing the SV40 late transcriptional termination signal was isolated.

4. Using linkers and other standard recombinant DNA techniques, the CMV promotor-MoMLV gag/pol-SV40 termination signal was ligated into the bluescript vector SK+.

An example of the construction of an MLV amphotropic envelope expression vector (pCMVvenvAmDra, see FIG. 19B.2) follows:

1. A 2.7 Kb XbaI/NheI fragment containing the coding sequence of amphotropic envelope from the 4070A proviral clone (Chattopadhyay et al., *J. Virol.* 39:777–91, 1981) was isolated.

2. Using linkers and other standard DNA techniques, the CMV early promoter and SV40 late termination signal described for the gag/pol expression above (pSCV10) were ligated in the order CMV promoter-envelope-termination signal.

A second example of the construction of an MLV amphotropic envelope expression vector (PCMVenvAmNhe, see FIG. 19B.3) follows:

1. A 2.7 Kb XbaI/NheI fragment containing the coding sequence of amphotropic envelope from the 4070A proviral clone described above was isolated.

2. Using linkers and other standard recombinant DNA techniques, the CMV early promoter described for the gag/pol expression above (pSCV10) was ligated in the plasmid pUC18 in the order CWV promoter-envelope (no added transcriptional termination signal).

A third example of the construction of an MLV amphotropic envelope expression vector (pMLPenvAmSph, see FIG. 19B.4) follows.

1. A 0.9 Kb EcoRI/HindIII fragment containing the Adenovirus 5 left end, major late transcriptional promoter, and tripartite leader sequence was isolated.

2. A 0.85 Kb EcoRI/BamHI fragment containing the SV40 small t intron and transcriptional termination signal from clone pJD204 (De Wit et al., *Mol. Cell. Biol.* 7:725–37, 1987) was isolated.

3. A 3 Kb SphI/SmaI fragment containing the coding sequence of amphotropic envelope from the 4070A proviral clone described above was isolated.

4. Using linkers and other standard recombinant DNA techniques, the MLP, amphotropic envelope and the SV40 termination signal were ligated in plasmid pBR322 in the order MLP-envelope-SV40.

An example of the construction of an MLV xenotropic envelope expression vector (pCMMVxeno, see FIG. 19B.5) follows.

1. A 2.2 Kb NaeI/NheI fragment containing the coding region of the xenotropic envelope obtained from clone NZB9-1 (O'Neill et al., *J. Virol.* 53:100–106, 1985) was isolated.

2. Using linkers and other standard recombinant DNA techniques, the CMV early promoter and SV40 late termination signal described for the gag/pol expression above (pSCV10) were ligated in the order CMV promoter-envelope-termination signal.

An example of the construction of an MLV polytropic envelope expression vector (pCMVMCF, see FIG. 19B.6) follows.

1. A 2 Kb BamHI/NheI fragment containing the coding region of the polytropic envelope obtained from clone MCF-247W (Holland et al., *J. Virol.* 53:152–57, 1985) was isolated.

2. Using linkers and other standard recombinant DNA techniques, the CMV early promoter and SV40 late termination signal described for the gag/pol expression above (pSCV10) were ligated in the order CKV promoter-envelope-termination signal.

An example of the construction of an MLV ampho env Neo+ retroviral vector (pLARNL, FIG. 19B.7) follows.

1. The vector pLRNL vector (Li et al., *Virology* 171:331–41, 1989) was digested with BamHI.

2. A 2.7 Kb XbaI fragment containing the envelope protein coding region of retrovirus 4070A (Chattopadhyay et al., *J. Virol.* 39:777–91, 1981) was isolated.

3. Fragments from procedures 1 and 2 above were ligated.

B. Host Cell Selection

Host cell lines were screened for their ability to efficiently (high titre) rescue a drug resistance retroviral vector (A alpha N2) using replication competent retrovirus to produce the gag/pol and env structural genes ("MA" virus). Titre was measured from confluent 25 monolayers 16 h after a medium change by adding filtered supernatants (0.45 um filters) to $5 \times 10^4$ NIH 3T3 TK− cells on a 6 cm tissue culture plate in the presence of 4 ug/ml polybrene followed by selection in G418.

Data from the screening process is shown in FIG. 19C. Among the non-murine cell lines which demonstrate the ability to package MoMLV-based vector with high titre are the cell lines CF2, D17, 293, and HT1080. These cell lines were used herein as examples, although any other cells may be tested by such means.

C. Generation of Packaaina Cell (i) gag/pol intermediate

As examples of the generation of gag/pol intermediates for PCL production, D17, 293, and HT1080 were co-transfected with 1 ug of the methotrexate resistance vector, pFR400 (Graham and van der Eb, *Virlocry* 52:456–67, 1973), and 10 ug of the MoMLV gag/pol expression vector, pSCV10 (above) by calcium phosphate coprecipitation (D17 and HT1080, see Graham and van der Eb, *Virology* 52:456–67, 1973), or lipofection (293, see Feigner et al., *Proc. Natl. Acad. Sci., USA* 84:7413–17, 1987). After selection for transfected cells in the presence of the drugs dipyrimidol and methotrexate, individual drug resistant cell colonies were expanded and analyzed for MoMLV gag/pol expression by extracellular reverse transcriptase (RT) activity (modified from Goff et al., *J. Virol.* 38:239–48, 1981) and intracellular $P30^{gag}$ by western blot using anti p30 antibodies (goat antiserum #77S000087 from the National Cancer Institute). This method identified individual cell clones in each cell type which expressed 10–50× higher levels of both proteins compared with that of the PCL, PA317 (FIG. 19D and Table 3).

TABLE 3

PROPERTIES OF MoMLV GAG/POL-EXPRESSING CELLS

| CELL NAME | RT ACTIVITY (CPM) | $p30^{gag}$ EXPRESSION | LARNL TITRE (CFU/ML) |
|---|---|---|---|
| 3T3 | 800 | – | N.D. |
| PA317 | 1350 | +/– | $1.2 \times 10^3$ |
| D17 | 800 | – | N.D. |
| D17 4-15 | 5000 | +++++ | $1.2 \times 10^4$ |
| D17 9020 | 2000 | +++ | $6.0 \times 10^3$ |
| D17 9-9 | 2200 | ++ | $1.0 \times 10^3$ |
| D17 9-16 | 6100 | +++++ | $1.5 \times 10^4$ |
| D17 8-7 | 4000 | – | N.D. |
| HT1080 | 900 | – | N.D. |
| HTSCV21 | 16400 | +++++ | $8.2 \times 10^3$ |
| HTSCV25 | 7900 | +++ | $2.8 \times 10^3$ |
| HTSCV42 | 11600 | ++ | $8.0 \times 10^2$ |
| HTSCV26 | 4000 | – | <10 |
| 293 | 600 | – | N.D. |
| 293 2-3 | 6500 | +++++ | $7 \times 10^4$ |
| 293 5-2 | 7600 | +++++ | N.D. |

The biological activity of these proteins was tested by introducing a retroviral vector, LARNL (see FIG. 19B) which expresses both the amphotropic envelope and a Neo+ marker which confers resistance to the drug, G418. In every case, co-expression of gag/pol in the cell line and env from the vector allowed efficient packaging of the vector as determined by cell-free transfer of G418 resistance to 3T3 cells (titre). Titre was measured from confluent monolayers 16 h after a medium change by adding filtered supernatants (0.45 um filters) to $5 \times 10^4$ NIH353 TK+ cells on a 6 cm tissue culture plate in the presence of 4 ug/ml polybrene followed by selection in G418. Significantly, the vector titres from the cell lines correlated with the levels of $p30^{gag}$ (Table 3). Since the level of env should be the same in each clone and is comparable to the level found in PA317 (data not shown), this indicates thai titre was limited by the lower levels of gag/pol in these cells (including PA317). The titre correlated more closely with the levels of $p30^{gag}$ than with the levels of RT.

(ii) Conversion of gag/pol lines into amphotropic packaging lines

As examples of the generation of amphotropic PCLs, the gag/pol over-expressors for 293 (termed 2–3) and D17 (termed 4–15) were co-transfected by the same techniques described above except that 1 ug of the phleomycin resistance vector, pUT507 (Mulsant et al., *Somat. Cell Mol. Genet.* 14:243–52, 1988), and 10 ug of the amphotropic envelope expression vectors, pMLPenvAmSph (for 2–3) or pCMVenvAmNhe (for 4–15) were used. After selection for transfected cells in the presence of phleomycin, individual drug resistant cell colonies were expanded and analyzed for intracellular $gp80^{env}$ expression by western blot using anti gp70 (goat antiserum #79S000771 from N.C.I.). Several clones were identified which expressed relatively high levels of both gag/pol and ampho env (PCLs, see FIG. 19 for representative data).

In another example of the generation of an ampho PCL, CF2 cells were electroporated (cf. Chu et al., *Nucl. Acids Res.* 15:1311–26, 1987) with 2 ug of the phleomycin resistance marker, pUT507, 10 ug of pSCV10 (above), and 10 ug of pCMVenvAmNhe (above). After selection for transfected cells in the presence of phleomycin, individual drug resistant cell colonies were expanded and analyzed for intracellular expression of MLV $p30^{gag}$ and $gp80^{env}$ proteins by western blot using specific antisera. A clone was identified which expressed relatively high levels of both gag/pol and ampho env (FIG. 19E).

(iii) Performance of amphotropic packaging cell lines.

A number of these ampho PCLs were tested for their capacity to package retroviral vectors by measuring titre after the introduction of retroviral vectors (Table 4). The measurements were performed using uncloned PCLS, so that the average performance of the lines was calculated.

TABLE 4

VECTOR TITRE AND HELPER VIRUS GENERATION IN AMPHOTROPIC PCLs

| | VECTOR TITRE[a] | | | (+/–HELPER VIRUS[b]) |
|---|---|---|---|---|
| CELL TYPE | β-Gal | KT-1 | N2 | |
| PA317 | $3.5 \times 10^2$ | (N.D.) | $1.0 \times 10^4$ (N.D.) | $3.0 \times 10^5 (+)^c$ |
| CA | $5.0 \times 10^4$ | (N.D.) | $3.0 \times 10^5 (-)^d$ | $2.0 \times 10^4 (-)^d$ |
| 2A | $4.0 \times 10^4$ | (N.D.) | $2.0 \times 10^5 (-)^e$ | N.D. |
| DA | N.D. | | N.D. | $2.0 \times 10^5 (-)^d$ |

[a]cfu/ml
[b]judged by marker rescue assay with MA virus as positive control
[c]after 20 days in culture
[d]after 60 days in culture
[e]after 90 days in culture Highest titres are obtained when retroviral vectors were introduced into PCLs by infection (Miller et al., *Somat. Cell Mol. Genet.* 12:175–83, 1986). However, although amphotropic MLV vectors are known to infect these host cell types, the PCLs are blocked for infection by ampho vector since they express ampho env ("viral interference"). To overcome this problem, vectors containing other viral envelopes (such as xenotropic env or VSV G protein, which bind to cell receptors other than the ampho receptor) were generated in the following manner. Ten ug of the vector DNA of interest was co-transfected with 10 ug of DNA which expresses either xeno env (pCMVxeno, above) or a VSV G protein expression vector, MLP G, onto a cell line which expresses high levels of MoMLV gag/pol such as 2–3 cell (see above). The resultant vector containing xenotropic env or VSV G protein, respectively, was produced transiently in the co-transfected cells and after 2 days cell free supernatants were added to the potential PCLs, and vector-infected cells were identified by selection in G418. Both types of vector efficiently infected the ampho-blocked cells and after G418 selection call free supernatants were collected from the confluent monolayers and titred on NIH 3T3 TK⁻ cells as described above. The cell clones with the highest titre were chosen as PCLs and referred to as DA (D17 ampho), 2A (293 ampho), and CA (CF2 ampho), respectively. In no case was helper virus detected in the currently described PCLs, even when a retroviral vector (N2) which has a high probability of generating helper virus (Armentano et al., *J. Virol.* 62:1647–50, 1987) was introduced into the PCLs and the cells passaged for as long as 2 months (3 months for vector KT-3). On the other hand, the same vector introduced into the PA317 cell line generated helper virus within 3 weeks of continual passaging.

(iv) Conversion of gag/pol lines into xenotropic packaging cell lines.

As examples of the generation of xenotropic PCLS, the gag/pol over-expressors for D17 (4–15) and HT1080 (SCV21) were co-transfected by the same techniques described above except that 1 ug of either the phleomycin resistance vector, pUT507 (for SCV21), or the hygromycin B resistance marker, pY3 (for 4–15, see Blochlinger and Diggelmann, *Mol. Cell Biol.* 4:2929–31, 1984), and 10 ug of the xenotropic envelope expression vector, pCMVxeno (above) was used. After selection for transfected cells in the presence of phleomycin or hygromycin, respectively, individual drug resistant cell colonies were expanded and analyzed for intracellular expression of MLV p30$^{gag}$ and gp75$^{env}$ proteins by western blot using specific antisera. Clones were identified which expressed relatively high levels of both gag/pol and xeno env (FIG. 19F).

(v) Performance of xenotropic packaging cell lines.

A number of these potential xeno PCLs were tested for their capacity to package retroviral vectors by measuring titre after the introduction of retroviral vectors (Table 5).

TABLE 5

VECTOR TITRE ON XENOTROPIC PCLs

| CELL CLONE | | KT-1 TITRE (CFU/ML) ON HT1080 CELLS |
|---|---|---|
| HT1080 | SCV21 | $1.0 \times 10^5$ |
| | XF1 | $1.0 \times 10^5$ |
| | XF7 | $1.0 \times 10^5$ |
| | XF12 (HX) | $4.5 \times 10^5$ |
| D17 | 4-15 | |
| | X6 | $9.0 \times 10^4$ |
| | X10 (DX) | $1.3 \times 10^5$ |
| | X23 | $8.0 \times 10^4$ |

As described above, vector containing VSV G protein was produced transiently in 2–3 cells. After 2 days, cell free supernatants were added to the xeno PCLs and after G418 selection cell free supernatants were collected from the confluent monolayers and titred as described above except that HT1080 cells, which are infectable by xeno vector, was used instead of NIH 3T3 TK⁻ cells which are resistant to xeno vector. The cell clones with the highest titre were chosen as PCLs and referred to as DX (D17 xeno) and HX (HT1080 xeno), respectively.

The propensity of the PCLs described above to generate helper virus was tested even more stringently by co-cultivating ampho and xeno PCLs containing the vector, N2. Since ampho vector can infect the xeno PCLs and vice versa, this allows continuous cross-infection events, each of which increases the probability of generating helper virus. As an example, 2A cells containing N2 were co-cultivated with HX cells containing N2. After 23 days, the cultures were still free of ampho and xeno viruses as judged by a vector rescue assay on 293 or Mus dunni cells, both of which can detect ampho and xeno viruses (Table 6).

TABLE 6

HIGH STRINGENCY ANALYSIS FOR PCL TENDENCY TO GENERATE HELPER VIRUS

| TEST MATERIAL | HELPER VIRUS ASSAY |
|---|---|
| AMPHOTROPIC VIRUS | + |
| XENOTROPIC VIRUS | + |
| PA317 + N2 (21d) | + |
| 2A + HX + N2 (23d) | − |

(vi) Conversion of gag/pol lines into polytropic packaging cell lines.

As an example of the generation of a polytropic PCL, the gag/pol over-expressor for HT1080 (SCV21) was co-transfected by the same techniques described above, except that 1 ug of the phleomycin resistance vector, pUT507, and 10 ug of the polytropic envelope expression vector, pCMVMCF (above) was used. After selection for transfected cells in the presence of phleomycin, individual drug resistant cell colonies were expanded and analyzed for intracellular expression of MLV gp70$^{env}$ protein by western blot using specific antiserum. Clones were identified which expressed relatively high levels of both gag/pol (not shown) and polytropic env (FIG. 19G).

(vii) Performance of polytropic packaging cell lines.

One of these potential poly PCLs (clone 3) was tested for the capacity to package retroviral vectors by measuring titre after the introduction of retroviral vectors (Table 7).

TABLE 7

HOST-RANGE OF POLYTROPIC VECTOR FROM HP CELLS

| CELL LINE | SPECIES | β-Gal TITRE |
|---|---|---|
| 3T3 | MURINE | $1.0 \times 10^4$ |
| PA317 | MURINE | $1.0 \times 10^4$ |
| Mv-1-Lu | MINK | $5.0 \times 10^3$ |
| FRh1 | MACAQUE | <10 |
| HT1080 | HUMAN | <10 |
| HeLa | HUMAN | <10 |
| WI 38 | HUMAN | <10 |
| DETROIT 557 | HUMAN | <10 |
| SUP TI | HUMAN | <10 |
| CEM | HUMAN | <10 |
| U937 | HUMAN | <10 |
| 293 | HUMAN | $2.0 \times 10^4$ |

This cell clone was chosen as PCL and referred to as HP (HT1080 poly). As described above, vector containing VSV G protein was produced transiently in 2–3 cells and after 26 days, cell free supernatants were added to the polytropic PCL (HP). After G418 selection, cell free supernatants were collected from the confluent monolayers and titred as described above on a variety of cell lines. The infection of human cells was very restricted, with all cell lines tested being negative with the exception of 293 cells.

Although the factors that lead to efficient infection of specific cell types by retroviral vectors are not completely understood, it is clear that because of their relatively high mutation rate, retroviruses may be adapted for markedly improved growth in cell types in which initial growth is poor, simply by continual reinfection and growth of the virus in that cell type (the adapter cell). This can also be achieved using viral vectors that encode some viral functions (e.g., env), and which are passed continuously in cells of a particular type which have been engineered to have the functions necessary to complement those of the vector to give out infectious vector particles (e.g., gag/pol). For example, one can adapt the murine amphotropic virus 4070A to human T-cells or monocytes by continuous growth and reinfection of either primary cell cultures or permanent cell lines such as Sup T1 (T-cells) or U937 (monocvtes). Once maximal growth has been achieved, as measured by reverse transcriptase levels or other assays of virus production, the virus is cloned out by any of a number of standard methods, the clone is checked for activity (i.e., the ability to give the same maximal growth characteristic on transfection into the adapter cell type) and this genome used to make defective helper genomes and/or vectors which in turn, in an appropriately manufactured helper or producer line, will lead to production of viral vector particles which infect and express in the adapter cell type with high efficiency ($10^8$–$10^9$ infectious units/ml).

VII. Alternative Viral Vector Packaging Technicues

Two additional alternative systems can be used to produce recombinant retroviruses carrying the vector construct. Each of these systems takes advantage of the fact that the insect virus, baculovirus, and the mammalian viruses, vaccinia and adenovirus, have been adapted recently to make large amounts of any given protein for which the gene has been cloned. For example, see Smith et al. (*Mol. Cell. Biol.* 3:12, 1983); Piccini et al. (*Meth. Enzymolocy*, 153:545, 1987); and Mansour et al. (*Proc. Natl. Acad. Sci. USA* 82:1359, 1985).

These viral vectors can be used to produce proteins in tissue culture cells by insertion of appropriate genes into the viral vector and, hence, could be adapted to make retroviral vector particles.

Adenovirus vectors are derived from nuclear replicating viruses and can be defective. Genes can be inserted into vectors and used to express proteins in mammalian cells either by in vitro construction (Ballay et al., *EMBO J.* 4:3861, 1985) or by recombination in cells (Thummel et al., *J. Mol. Appl. Genetics* 1:435, 1982).

One preferred method is to construct plasmids using the adenovirus Major Late Promoter (MLP) driving:

(1) gag/pol, (2) env, (3) a modified viral vector construct. A modified viral vector construct is possible because the U3 region of the 5' LTR, which contains the viral vector promoter, can be replaced by other promoter sequences (see, for example, Hartman, *Nucl. Acids Res.* 16:9345, 1988). This portion will be replaced after one round of reverse transcriptase by the U3 from the 3' LTR.

These plasmids can then be used to make adenovirus genomes in vitro (Ballay et al., op. cit.), and these transfected in 293 cells (a human cell line making adenovirus E1A protein), for which the adenoviral vectors are defective, to yield pure stocks of gag/pol, env and retroviral vector carried separately in defective adenovirus vectors. Since the titres of such vectors are typically $10^7$–$10^{11}$/ml, these stocks can be used to infect tissue culture cells simultaneously at high multiplicity. The cells will then be programmed to produce retroviral proteins and retroviral vector genomes at high levels. Since the adenovirus vectors are defective, no large amounts of direct cell lysis will occur and retroviral vectors can be harvested from the cell supernatants.

Other viral vectors such as those derived from unrelated retroviral vectors (e.g., RSV, MMTV or HIV) can be used in the same manner to generate vectors from primary cells. In one embodiment, these adenoviral vectors are used in conjunction with primary cells, giving rise to retroviral vector preparations from primary cells.

In an alternative system (which is more truly extracellular), the following components are used:

1. gag/pol and env proteins made in the baculovirus system in a similar manner as described in Smith et al. (suora) (or in other protein production systems, such as yeast or E. coli);
2. viral vector RNA made in the known T7 or SP6 or other in vitro RNA-generating system (see, for example, Flamant and Sorge, *J. Virol.* 62:1827, 1988);
3. tRNA made as in (2) or purified from yeast or mammalian tissue culture cells;
4. liposomes (with embedded env protein); and
5. cell extract or purified necessary components (when identified) (typically from mouse cells) to provide env processing, and any or other necessary cell-derived functions.

Within this procedure (1), (2) and (3) are mixed, and then env protein, cell extract and pre-liposome mix (lipid in a suitable solvent) added. It may, however, be necessary to earlier embed the env protein in the liposomes prior to adding the resulting liposome-embedded env to the mixture of (1), (2), and (3). The mix is treated (e.g., by sonication, temperature manipulation, or rotary dialysis) to allow encapsidation of the nascent viral particles with lipid plus embedded env protein in a manner similar to that for liposome encapsidation of pharmaceuticals, as described in Gould-Fogerite et al., *Anal. Biochem.* 148:15, 1985). This procedure allows the production of high titres of replication incompetent recombinant retroviruses without contamination with pathogenic retroviruses or replication-competent retroviruses.

VIII. Cell Line-Specific Retroviruses—"Hybrid Envelope"

The host cell range specificity of a retrovirus is determined in part by the env gene products. For example, Coffin, J. (*RNA Tumor Viruses* 2:25–27, Cold Spring Harbor, 1985) notes that the extracellular component of the proteins from murine leukemia virus (MLV) and Rous Sarcoma virus (RSV) are responsible for specific receptor binding. The cytoplasmic domain of envelope proteins, on the other hand, are understood to play a role in virion formation. While pseudotyping (i.e., the encapsidation of viral RNA from one species by viral proteins of another species) does occur at a low frequency, the envelope protein has some specificity for virion formation of a given retrovirus. The present invention recognizes that by creating a hybrid env gene product (i.e., specifically, an env protein having cytoplasmic regions and exogenous binding regions which are not in the same protein molecule in nature) the host range specificity may be changed independently from the cytoplasmic function. Thus, recombinant retroviruses can be produced which will specifically bind to preselected target cells.

In order to make a hybrid protein in which the receptor binding component and the cytoplasmic component are from different retroviruses, a preferred location for recombination is within the membrane-spanning region of the cytoplasmic component. Example 10 describes the construction of a hybrid env gene which expresses a protein with the CD4 binding portion of the HIV envelope protein coupled to the cytoplasmic domain of the MLV envelope protein.

EXAMPLE 10

Hybrid HIV-MLV Envelopes

A hybrid envelope gene is prepared using in vitro mutagenesis (Kunkel, *Proc. Natl. Acad. Sci. USA*

82:488–492, 1985) to introduce a new restriction site at an appropriate point of junction. Alternatively, if the two envelope sequences are on the same plasmid, they can be joined directly at any desired point using in vitro mutagenesis. The end result in either case is a hybrid gene containing the 5' end of the HIV gp 160 and the 3'end of MLV p15E. The hybrid protein expressed by the resulting recombinant gene is illustrated in FIG. 20 and contains the HIV gp120 (CD4 receptor binding protein), the extracellular portion of HIV gp 41 (the gp 120 binding and fusigenic regions), and the cytoplasmic portion of MLV p15E, with the joint occurring at any of several points within the host membrane. A hybrid with a fusion joint at the cytoplasmic surface (joint C in FIG. 20) causes syncytia when expressed in Sup T1 cells. The number of apparent syncytia are approximately one-fifth that of the nonhybrid HIV envelope gene in the same expression vector. Syncytia with the hybrid occurs only when the rev protein is co-expressed in trans. A hybrid with a fusion joint at the extracellular surface (joint A in FIG. 20) gives no syncytia while hybrid B (in the middle of the transmembrane regions) gives approximately five-fold less syncytium on Sup T1 cells than hybrid C.

While Example 10 illustrates one hybrid protein produced from two different retroviruses, the possibilities are not limited to retroviruses or other viruses. For example, the beta-receptor portion of human interleukin-2 may be combined with the envelope protein of MLV. In this case, a recombination would preferably be located in the gp 70 portion of the MLV env gene, leaving an intact p15E protein. Furthermore, the foregoing technique may be used to create a recombinant retrovirus with an envelope protein which recognizes antibody Fc segments. Monoclonal antibodies which recognize only preselected target cells only could then be bound to such a recombinant retrovirus exhibiting such envelope proteins so that the retrovirus would bind to and infect only those preselected target cells.

The approach may also be used to achieve tumor-specific targeting and killing by taking advantage of three levels of retroviral vector specificity; namely, cell entry, gene expression, and choice of protein expressed. Retroviral vectors enter cells and exert their effects at intracellular sites. In this respect their action is quite unique. Using this property, and the three levels of natural retroviral specificity (above), retroviral vectors may be engineered to target and kill tumor cells.

The overall goal of targeting of retrovirus to tumor cells may be accomplished by two major experimental routes; namely, a) selection in tissue culture (or in animals) for retroviruses that grow preferentially in tumor cells; or b) construction of retroviral vectors with tissue (tumor)-specific promoters with improvements being made by in vitro passage, and negative and positive drug-sensitivity selection.

At least four selective protocols may be utilized to select for retrovirus which grow preferentially in tumor cells; namely, 1) “Env Selection by Passage In Vitro,” wherein selection of retrovirus with improved replicative growth ability is accomplished by repeated passage in tumor cells; 2) “Selection with a Drug Resistance Gene,” wherein genetic selection for tumor “specific” retroviruses is based on viral constructs containing a linked drug resistance gene; 3) “Hybrid-Env,” wherein selection (by protocol #1 or #2, above) of retrovirus with tumor-“specificity” is initiated from a construct containing a hybrid envelope gene which is a fusion of a tumor receptor gene (i.e., an anti-tumor antibody H-chain V-region gene fused with env; or, a growth receptor fused with env); in this case selection begins at a favorable starting point, e.g., an env which has some specificity for tumor cells; or 4) “Selection by Passage In Vitro and Counter Selection by Co-cultivation with Normal Cells,” wherein growth in tumor cells is selected-for by repeated passage in mixtures of drug-resistant tumor cells and drug-sensitive normal cells.

With respect to retroviral vector constructs carrying tissue (tumor)-specific promoters, biochemical markers with different levels of tissue-specificity are well known, and genetic control through tissue-specific promoters is understood in some systems. There are a number of genes whose transcriptional promoter elements are relatively active in rapidly growing cells (i.e., transferrin receptor, thymidine kinase, etc.) and others whose promoter/enhancer elements are tissue specific (i.e., HBV enhancer for liver, PSA promoter for prostate). Retroviral vectors and tissue-specific promoters (present either as an internal promoter or within the LTR) which can drive the expression of selectable markers and cell cycle genes (i.e., drug sensitivity, Eco gpt; or HSVTK in TK-cells). Expression of these genes can be selected for in media containing mycophenolic acid or HAT, respectively. In this manner, tumor cells containing integrated provirus which actively expresses the drug resistance gene will survive. Selection in this system may involve selection for both tissue-specific promoters and viral LTRs. Alternatively, specific expression in tumor cells, and not in normal cells, can be counter-selected by periodically passaging virus onto normal cells, and selecting against virus that express Eco gpt or HSVtk (drug sensitivity) in those cells (by thioxanthine or acyclovir). Infected cells containing integrated provirus which express Eco gpt or tk phenotype will die and thus virus in that cell type will be selected against.

IX. Site-Specific Integration

Targeting a retroviral vector to a predetermined locus on a chromosome increases the benefits of gene-delivery systems. A measure of safety is gained by direct integration to a “safe” spot on a chromosome, i.e., one that is proven to have no deleterious effects from the insertion of a vector. Another potential benefit is the ability to direct a gene to an “open” region of a chromosome, where its expression would be maximized. Two techniques for integrating retroviruses at specific sites are described below.

(i) Homologous Recombination

One technique for integrating an exogenous gene of a vector construct of a recombinant retrovirus into a specific site in a target cell’s DNA employs homologous recombination. Plasmids containing sequences of DNA of greater than about 300 bp that are homologous to genomic sequences have been shown to interact (either by replacement or insertion) with those genomic sequences at a rate that is greater than $10^3$-fold over a specific interaction in the absence of such homology (see Thomas and Capecchi, *Cell* 51:503–12, 1987; and Doetscheman et al., *Nature* 330:576–78, 1987). It has been shown that an insertion event, or alternatively, a replacement event, may be driven by the specific design of the vector.

In order to employ homologous recombination in site-specific retroviral integration, a vector construct should be modified such that (a) homologous sequences (to the target cell’s genome) are incorporated into the construct at an appropriate location; and (b) the normal mechanism of integration does not interfere with the targeting occurring due to homologous sequences. A preferred approach in this regard is to add homologous sequences (greater than about 300 bp) in the 3' LTR, downstream from the U3 inverted repeat. In this approach, the construct is initially made with a region of homology inserted in the 3' LTR at the Nhe 1 site in U3. Reverse transcription in the host cell will result in a duplication of the region of homology in the 5' LTR within 31 bp of the end of the inverted repeat (IR). Integration into the host genome will occur in the presence or absence of the normal integration mechanism. The gene in the vector may be expressed, whether from the LTR or from an internal promoter. This approach has the effect of placing a region of homology near a potential free end of the double-stranded retrovirus vector genome. Free ends are known to increase the frequency of homologous recombination by a factor of approximately ten. In this approach, it may be necessary to defeat the normal mechanism of integration, or to at least modify it to slow down the process, allowing time for homologous DNAs to line up. Whether this latter modification is required in a particular case can be readily ascertained by one skilled in the art.

(ii) Integrase Modification

Another technique for integrating a vector construct into specific, preselected sites of a target cell's genome involves integrase modification.

The retrovirus pol gene product is generally processed into four parts: (i) a protease which processes the viral gag and pol products; (ii) the reverse transcriptase; and (iii) RNase H, which degrades RNA of an RNA/DNA duplex; and (iv) the endonuclease or "integrase."

The general integrase structure has been analyzed by Johnson et al. (*Proc. Natl. Acad. Sci. USA* 83:7648–7652, 1986). It has been proposed that this protein has a zinc binding finger with which it interacts with the host DNA before integrating the retroviral sequences.

In other proteins, such "fingers" allow the protein to bind to DNA at particular sequences. One illustrative example is the steroid receptors. In this case, one can make the estrogen receptor, responding to estrogens, have the effect of a glucocorticoid receptor, responding to glucocorticoids, simply by substituting the glucocorticoid receptor "finger" (i.e., DNA binding segment) in place of the estrogen receptor finger segment in the estrogen receptor gene. In this example, the position in the genome to which the proteins are targeted has been changed. Such directing sequences can also be substituted into the integrase gene in place of the present zinc finger. For instance, the segment coding for the DNA binding region of the human estrogen receptor gene may be substituted in place of the DNA binding region of the integrase in a packaging genome. Initially, specific integration would be tested by means of an in vitro integration system (Brown et al., *Cell* 29:347–356, 1987). To confirm that the specificity would be seen in vivo, this packaging genome is used to make infectious vector particles, and infection of and integration into estrogen-sensitive and estrogen-nonsensitive cells compared in culture.

Through use of this technique, incoming viral vectors may be directed to integrate into preselected sites on the target cell's genome, dictated by the genome-binding properties of site-specific DNA-binding protein segments spliced into the integrase genome. It will be understood by those skilled in the art that the integration site must, in fact, be receptive to the fingers of the modified integrase. For example, most cells are sensitive to glucocorticoids and hence their chromatin has sites for glucocorticoid receptors. Thus, for most cells, a modified integrase having a glucocorti-coid receptor finger would be suitable to integrate the proviral vector construct at those glucocorticoid receptor-binding sites.

X. Production of Recombinant Retroviral Vectors in Transgenic Animals

Two problems previously described with helper line generation of retroviral vectors are: (a) difficulty in generating large quantities of vectors; and (b) the current need to use permanent instead of primary cells to make vectors. These problems can be overcome with producer or packaging lines that are generated in transgenic animals. These animals would carry the packaging genomes and retroviral vector genomes. Current technology does not allow the generation of packaging cell lines and desired vector-producing lines in primary cells due to their limited life span. The current technology is such that extensive characterization is necessary, which eliminates the use of primary cells because of senescence. However, individual lines of transgenic animals can be generated by the methods provided herein which produce the packaging functions, such as gag, pol or env. These lines of animals are then characterized for expression in either the whole animal or targeted tissue through the selective use of housekeeping or tissue-specific promoters to transcribe the packaging functions. The vector to be delivered is also inserted into a line of transgenic animals with a tissue-specific or housekeeping promoter. As discussed above, the vector can be driven off such a promoter substituting for the U3 region of the 5' LTR (FIG. 21). This transgene could be inducible or ubiquitous in its expression. This vector, however, is not packaged. These lines of animals are then mated to the gag/pol/env animal and subsequent progeny produce packaged vector. The progeny, which are essentially identical, are characterized and offer an unlimited source of primary producing cells. Alternatively, primary cells making gag/pol and env and derived from transgenic animals can be infected or transfected in bulk with retrovirus vectors to make a primary cell producer line. Many different transgenic animals or insects could produce these vectors, such as mice, rats, chickens, swine, rabbits, cows, sheep, fish and flies. The vector and packaging genomes would be tailored for species infection specificity and tissue-specific expression through the use of tissue-specific promoters and different envelope proteins. An example of such a procedure is illustrated in FIG. 22.

Although the following examples of transgenic production of primary packaging lines are described only for mice, these procedures can be extended to other species by those skilled in the art. These transgenic animals may be produced by microinjection or gene transfer techniques. Given the homology to MLV sequences in mice genome, the final preferred animals would not be mice.

EXAMPLE 11

Production of Gag/Pol Proteins Using Housekeeping Promoters for Ubiquitous Expression in Transgenic Animals An example of a well-characterized housekeeping promoter is the HPRT promoter. HPRT is a purine salvage enzyme which expresses in all tissues. (See Patel et al., *Mol. Cell Biol.* 6:393–403, 1986 and Melton et al., *Proc. Natl. Acad. Sci.* 81:2147–2151, 1984). This promoter is inserted in front of various gag/pol fragments (e.g., Bal I/Sca I; Aat II/Sca I; Pst I/Sca I of MOMLV; see *RNA Tumor Viruses 2*, Cold Spring Harbor Laboratory, 1985) that are cloned in Bluescript plasmids (Strategene, Inc.) using recombinant DNA techniques (see Maniatis et al., *Molecular Clonina: A Laboratorv Manual*, Cold Spring Harbor, 1982). The resulting plasmids are purified (Maniatis et al., op. cit.) and the relevant genetic information isolated using Geneclean (Bio 101) or electroelution (see Hogan et al. (eds.), *Manipulatina the Mouse Embryo: A Laboratory Manual*, Cold Spring Harbor, 1986).

These fully characterized DNAs are microinjected in the pronucleus of fertilized mouse ova at a concentration of 2 ug/ml. Live-born mice are screened by tail blot analyses (see Hogan et al., op. cit.). Transgenic-positive animals are characterized for expression levels of gag/pol proteins by immunoprecipitation of radiolabeled primary cells, such as fibroblast (see Harlow et al. (eds.), *Antibodies: A Laboratory Manual*, Cold Spring Harbor, 1988). Animals then bred to homozygosity for establishment of animal lines that produce characterized levels of gag/pol.

EXAMPLE 12

Production of env Proteins/Hybrid Envelope Proteins Using Housekeeping Promoters for Ubiquitous Expression in Transgenic Animals This example utilizes the HPRT promoter for expression of either envelope or hybrid envelope proteins. The envelope proteins can be from any retrovirus that is capable of complementing the relevant gag/pol, in this case that of MLV. Examples are ecotropic MLV, amphotrophic MLV, xenotropic MLV, polytropic MLV, or hybrid envelopes. As above, the envelope gene is cloned behind the HPRT promoter using recombinant DNA techniques (see Maniatis et al., op. cit.). The resulting "minigene" is isolated (see Hogan et al., op. cit.), and expression of envelope protein is determined (Harlow et al., op. cit.). The transgenic envelope animals are bred to homozygosity to establish a well-characterized envelope animal.

EXAMPLE 13

Production of gag/pol-env Animals Using Housekeeping Promoters for Ubiquitous Expression in Transgenic Animals This uses the well-characterized gag/pol animals, as well as the animals for the establishment of a permanent gag/pol/envelope animal line. This involves breeding to homozygosity and the establishment of a well-characterized line. These lines are then used to establish primary mouse embryo lines that can be used for packaging vectors in tissue culture. Furthermore, animals ontaining the retroviral vector are bred into this line.

EXAMPLE 14

Production of Tissue-Specific Expression of gag/pol-env or Hybrid Envelope in Transgenic Animals This example illustrates high level expression of the gag/pol, envelope, or hybrid envelope in specific tissues, such as T-cells. This involves the use of CD2 sequences (see Lang et al., *EMBO J.* 7:1675–1682, 1988) that give position and copy number independence. The 1.5 kb Bam HI/Hind III fragment from the CD2 gene is inserted in front of gag/pol, envelope, or hybrid envelope fragments using recombinant DNA techniques. These genes are inserted into fertilized mouse ova by microinjection. Transgenic animals are characterized as before. Expression in T-cells is established, and animals are bred to homozygosity to establish well-characterized lines of transgenic animals. Gag/pol animals are mated to envelope animals to establish gag/pol-env animals expressing only in T-cells. The T-cells of these animals are then a source for T-cells capable of packaging retroviral vectors. Again, vector animals can be bred into these gag/pol-env animals to establish T-cells expressing the vector.

This technique allows the use of other tissue-specific promoters, such as milk-specific (whey), pancreatic (insulin or elastase), or neuronal (myelin basic protein) promoters. Through the use of promoters, such as milk-specific promoters, recombinant retroviruses may be isolated directly from the biological fluid of the progeny.

EXAMPLE 15

Production of Either Housekeenina or Tissue-Specific Retroviral Vectors in Transgenic Animals The insertion of retroviruses or retroviral vectors into the germ line of transgenic animals results in little or no expression. This effect, described by Jaenisch (see Jahner et al., *Nature* 298:623–628, 1982), is attributed to methylation of 5' retroviral LTR sequences. This technique would overcome the methylation effect by substituting either a housekeeping or tissue-specific promoter to express the retroviral vector/retrovirus. The U3 region of the 5' LTR, which contains the enhancer elements, is replaced with regulatory sequences from housekeeping or tissue-specific promoters (see FIG. 20). The 3' LTR is fully retained, as it contains sequences necessary for polyadenylation of the viral RNA and integration. As the result of unique properties of retroviral replication, the U3 region of the 5' LTR of the integrated provirus is generated by the U3 region of the 3' LTR of the infecting virus. Hence, the 3' is necessary, while the 5' U3 is dispensable. Substitution of the 5' LTR U3 sequences with promoters and insertion into the germ line of transgenic animals results in lines of animals capable of producing retroviral vector transcripts. These animals would then be mated to gag/pol-env animals to generate retroviral-producing animals (see FIG. 22).

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A method for destroying human tumor cells, comprising:
   (a) infecting human tumor cells with a recombinant, replication defective retroviral construct comprising a gene encoding a conditionally lethal gene product operatively linked to a promoter for expression in said infected cells, said conditionally lethal gene product processing within said infected cells a purine-based or pyrimidine-based prodrug from its non-toxic precursor form to its active toxic form; and
   (b) contacting said infected tumor cells with said prodrug, said conditionally lethal gene product processing within said infected cell said prodrug from its non-toxic precursor form to its active toxic form. whereupon said tumor cells are destroyed.

2. The method of claim 1, where in said infecting step, said human tumor cells are infected in vitro.

3. The method of claim 1, where in said infecting step, said human tumor cells are infected ex vivo.

4. The method of claim 1, where in said infecting step, said human tumor cells are infected by direct injection of the recombinant, replication defective retroviral construct in vivo.

5. The method of claim 1, wherein said conditionally lethal gene product is a Herpes Simplex thymidine kinase (HSVTK) or *E. coli* guanine phosphoribosyl transferase.

6. The method of claim 5, wherein said conditionally lethal gene product is a Herpes Simplex thymidine kinase.

7. The method of claim 6, wherein said prodrug is selected from the group consisting of acyclovir, FIAU, FIAC, DHPG, AZT and ddC.

8. The method of claim 7, wherein said prodrug is acyclovir.

9. The method of claim 5, wherein said gene product is *E. coli* guanine phosphoribosyl transferase.

10. The method of claim 9, wherein said prodrug is thioxanthine.

* * * * *